US00RE49973E

(19) United States
(12) Reissued Patent
Miller

(10) Patent Number: US RE49,973 E
(45) Date of Reissued Patent: May 21, 2024

(54) EXPANDABLE INTERVERTEBRAL IMPLANT, SYSTEM, KIT AND METHOD

(71) Applicant: DePuy Synthes Products, Inc., Raynham, MA (US)

(72) Inventor: William Miller, Middleboro, MA (US)

(73) Assignee: DePuy Synthes Products, Inc., Rayham, MA (US)

(21) Appl. No.: 16/441,356

(22) Filed: Jun. 14, 2019

Related U.S. Patent Documents

Reissue of:
(64) Patent No.: 9,717,601
Issued: Aug. 1, 2017
Appl. No.: 13/780,796
Filed: Feb. 28, 2013

(51) Int. Cl.
*A61F 2/44* (2006.01)
*A61F 2/30* (2006.01)
*A61F 2/46* (2006.01)

(52) U.S. Cl.
CPC ..... *A61F 2/4455* (2013.01); *A61F 2/447* (2013.01); *A61F 2/4611* (2013.01); *A61F 2002/3008* (2013.01); *A61F 2002/30156* (2013.01); *A61F 2002/3082* (2013.01)

(58) Field of Classification Search
CPC ..... A61F 2/4455; A61F 2/447; A61F 2/4611
USPC ..... 623/17.15
See application file for complete search history.

(56) References Cited

U.S. PATENT DOCUMENTS 1,802,560 A 4/1931 Kerwin
1,924,695 A 8/1933 Olson
1,965,653 A 7/1934 Kennedy
2,077,804 A 4/1937 Morrison
2,115,250 A 4/1938 Bruson
2,121,193 A 6/1938 Hanicke
2,170,111 A 8/1939 Bruson
(Continued)

FOREIGN PATENT DOCUMENTS

AU 2006279558 A1 2/2007
AU 2005314079 B2 7/2012
(Continued)

OTHER PUBLICATIONS

Alfen et al., "Developments in the area of Endoscopic Spine Surgery", European Musculoskeletal Review 2006, pp. 23-24, ThessysTM, Transforaminal Endoscopic Spine Systems, joi max Medical Solutions.

(Continued)

*Primary Examiner* — Glenn K Dawson
(74) *Attorney, Agent, or Firm* — BakerHostetler

(57) ABSTRACT

An implant includes a first plate and a second plate, a first wedge member and a second wedge member spaced from the first wedge member that couple the first and second plates together. The first and second wedge members configured to translate along the first and second plates from a first contracted configuration into a second separated configuration. The implant includes an actuation member coupled to the first wedge member and the second wedge member. The actuating member defines a flange extending toward the first and second plates. The actuation member configured to move the first and second wedge members from the first contracted configuration into the second separated configuration so that the first and second plates separate from each other.

35 Claims, 14 Drawing Sheets

(56) References Cited

U.S. PATENT DOCUMENTS 2,173,655 A 9/1939 Neracher et al.
2,229,024 A 1/1941 Bruson
2,243,717 A 5/1941 Moreira
2,381,050 A 8/1945 Hardinge
2,388,056 A 10/1945 Hendricks
2,485,531 A 10/1949 William et al.
2,489,870 A 11/1949 Dzus
2,570,465 A 10/1951 Lundholm
2,677,369 A 5/1954 Knowles
2,706,701 A 4/1955 Hans et al.
2,710,277 A 6/1955 Shelanski et al.
2,826,532 A 3/1958 Hosmer
2,900,305 A 8/1959 Siggia
2,977,315 A 3/1961 Scheib et al.
3,091,237 A 5/1963 Skinner
3,112,743 A 12/1963 Cochran et al.
3,115,804 A 12/1963 Johnson
3,228,828 A 1/1966 Romano
3,312,139 A 4/1967 Di Cristina
3,486,505 A 12/1969 Morrison
3,489,143 A 1/1970 Halloran
3,648,294 A 3/1972 Shahrestani
3,698,391 A 10/1972 Mahony
3,717,655 A 2/1973 Godefroi et al.
3,760,802 A 9/1973 Fischer et al.
3,800,788 A 4/1974 White
3,805,775 A 4/1974 Fischer et al.
3,811,449 A 5/1974 Gravlee et al.
3,842,825 A 10/1974 Wagner
3,848,601 A 11/1974 Ma et al.
3,855,638 A 12/1974 Pilliar
3,867,728 A 2/1975 Stubstad et al.
3,875,595 A 4/1975 Froning
3,889,665 A 6/1975 Ling et al.
3,964,480 A 6/1976 Froning
3,986,504 A 10/1976 Avila
4,013,071 A 3/1977 Rosenberg
4,052,988 A 10/1977 Doddi et al.
4,091,806 A 5/1978 Aginsky
4,105,034 A 8/1978 Shalaby et al.
4,130,639 A 12/1978 Shalaby et al.
4,140,678 A 2/1979 Shalaby et al.
4,141,087 A 2/1979 Shalaby et al.
4,175,555 A 11/1979 Herbert
4,205,399 A 6/1980 Jamiolkowski et al.
4,236,512 A 12/1980 Aginsky
4,249,435 A 2/1981 Smith et al.
4,262,665 A 4/1981 Roalstad et al.
4,262,676 A 4/1981 Jamshidi
4,274,163 A 6/1981 Malcom et al.
4,275,717 A 6/1981 Bolesky
4,312,337 A 1/1982 Donohue
4,312,353 A 1/1982 Shahbabian
4,313,434 A 2/1982 Segal
4,341,206 A 7/1982 Perrett et al.
4,349,921 A 9/1982 Kuntz
4,350,151 A 9/1982 Scott
4,351,069 A 9/1982 Ballintyn et al.
4,352,883 A 10/1982 Lim
4,369,790 A 1/1983 McCarthy
4,399,814 A 8/1983 Pratt et al.
4,401,112 A 8/1983 Rezaian
4,401,433 A 8/1983 Luther
4,409,974 A 10/1983 Freedland
4,440,921 A 4/1984 Allcock et al.
4,449,532 A 5/1984 Storz
4,451,256 A 5/1984 Weikl et al.
4,456,005 A 6/1984 Lichty
4,462,394 A 7/1984 Jacobs
4,463,753 A 8/1984 Gustilo
4,466,435 A 8/1984 Murray
4,467,479 A 8/1984 Brody
4,488,543 A 12/1984 Tornier
4,488,549 A 12/1984 Lee et al.
4,494,535 A 1/1985 Haig
4,495,174 A 1/1985 Allcock et al.
4,532,660 A 8/1985 Field
4,537,185 A 8/1985 Stednitz
4,538,612 A 9/1985 Patrick, Jr.
4,542,539 A 9/1985 Rowe et al.
4,545,374 A 10/1985 Jacobson
4,562,598 A 1/1986 Kranz
4,573,448 A 3/1986 Kambin
4,595,006 A 6/1986 Burke et al.
4,601,710 A 7/1986 Moll
4,625,722 A 12/1986 Murray
4,625,725 A 12/1986 Davison et al.
4,627,434 A 12/1986 Murray
4,628,945 A 12/1986 Johnson, Jr.
4,629,450 A 12/1986 Suzuki et al.
4,630,616 A 12/1986 Tretinyak
4,632,101 A 12/1986 Freedland
4,640,271 A 2/1987 Lower
4,641,640 A 2/1987 Griggs
4,645,503 A 2/1987 Lin et al.
4,646,741 A 3/1987 Smith
4,651,717 A 3/1987 Jakubczak
4,653,489 A 3/1987 Tronzo
4,665,906 A 5/1987 Jervis
4,667,663 A 5/1987 Miyata
4,686,973 A 8/1987 Frisch
4,686,984 A 8/1987 Bonnet
4,688,561 A 8/1987 Reese
4,697,584 A 10/1987 Haynes
4,706,670 A 11/1987 Andersen et al.
4,714,469 A 12/1987 Kenna
4,714,478 A 12/1987 Fischer
4,721,103 A 1/1988 Freedland
4,723,544 A 2/1988 Moore et al.
4,743,256 A 5/1988 Brantigan
4,743,257 A 5/1988 Toermaelae et al.
4,759,766 A 7/1988 Buettner-Janz et al.
4,760,843 A 8/1988 Fischer et al.
4,772,287 A 9/1988 Ray et al.
4,790,304 A 12/1988 Rosenberg
4,790,817 A 12/1988 Luther
4,796,612 A 1/1989 Reese
4,802,479 A 2/1989 Haber et al.
4,815,909 A 3/1989 Simons
4,827,917 A 5/1989 Brumfield
4,834,069 A 5/1989 Umeda
4,834,757 A 5/1989 Brantigan
4,838,282 A 6/1989 Strasser et al.
4,858,601 A 8/1989 Glisson
4,862,891 A 9/1989 Smith
4,863,476 A 9/1989 Shepperd
4,870,153 A 9/1989 Matzner et al.
4,871,366 A 10/1989 von Recum et al.
4,873,976 A 10/1989 Schreiber
4,878,915 A 11/1989 Brantigan
4,880,622 A 11/1989 Allcock et al.
4,888,022 A 12/1989 Huebsch
4,888,024 A 12/1989 Powlan
4,889,119 A 12/1989 Jamiolkowski et al.
4,892,550 A 1/1990 Huebsch
4,896,662 A 1/1990 Noble
4,898,186 A 2/1990 Ikada et al.
4,898,577 A 2/1990 Badger et al.
4,903,692 A 2/1990 Reese
4,904,261 A 2/1990 Dove et al.
4,911,718 A 3/1990 Lee et al.
4,917,554 A 4/1990 Bronn
4,932,969 A 6/1990 Frey et al.
4,940,467 A 7/1990 Tronzo
4,941,466 A 7/1990 Romano
4,946,378 A 8/1990 Hirayama et al.
4,959,064 A 9/1990 Engelhardt
4,961,740 A 10/1990 Ray et al.
4,963,144 A 10/1990 Huene
4,966,587 A 10/1990 Baumgart
4,968,317 A 11/1990 Toermaelae et al.
4,969,888 A 11/1990 Scholten et al.
4,978,334 A 12/1990 Toye et al.
4,978,349 A 12/1990 Frigg

(56) References Cited

U.S. PATENT DOCUMENTS 4,981,482 A 1/1991 Ichikawa
4,988,351 A 1/1991 Paulos et al.
4,994,027 A 2/1991 Farrell
4,995,200 A 2/1991 Eberhart
5,002,557 A 3/1991 Hasson
5,006,121 A 4/1991 Hafeli
5,011,484 A 4/1991 Breard
5,013,315 A 5/1991 Barrows
5,013,316 A 5/1991 Goble et al.
5,015,247 A 5/1991 Michelson
5,015,255 A 5/1991 Kuslich
5,019,082 A 5/1991 Frey et al.
5,030,233 A 7/1991 Ducheyne
5,051,189 A 9/1991 Farrah
5,053,035 A 10/1991 McLaren
5,055,104 A 10/1991 Ray
5,059,193 A 10/1991 Kuslich
5,062,849 A 11/1991 Schelhas
5,071,435 A 12/1991 Fuchs et al.
5,071,437 A 12/1991 Steffee
5,080,662 A 1/1992 Paul
5,084,043 A 1/1992 Hertzmann et al.
5,092,891 A 3/1992 Kummer et al.
5,098,241 A 3/1992 Aldridge et al.
5,098,433 A 3/1992 Freedland
5,098,435 A 3/1992 Stednitz et al.
5,102,413 A 4/1992 Poddar
5,108,404 A 4/1992 Scholten et al.
5,114,407 A 5/1992 Burbank
5,116,336 A 5/1992 Frigg
5,120,171 A 6/1992 Lasner
5,122,130 A 6/1992 Keller
5,122,133 A 6/1992 Evans
5,122,141 A 6/1992 Simpson et al.
5,123,926 A 6/1992 Pisharodi
5,133,719 A 7/1992 Winston
5,133,755 A 7/1992 Brekke
5,134,477 A 7/1992 Knauer et al.
5,139,486 A 8/1992 Moss
5,147,366 A 9/1992 Arroyo et al.
5,158,543 A 10/1992 Lazarus
5,163,939 A 11/1992 Winston
5,163,989 A 11/1992 Campbell et al.
5,167,663 A 12/1992 Brumfield
5,167,664 A 12/1992 Hodorek
5,169,400 A 12/1992 Muehling et al.
5,169,402 A 12/1992 Elloy
5,171,278 A 12/1992 Pisharodi
5,171,279 A 12/1992 Mathews
5,171,280 A 12/1992 Baumgartner
5,176,651 A 1/1993 Allgood et al.
5,176,683 A 1/1993 Kimsey et al.
5,176,692 A 1/1993 Wilk et al.
5,176,697 A 1/1993 Hasson et al.
5,178,501 A 1/1993 Carstairs
5,183,052 A 2/1993 Terwilliger
5,183,464 A 2/1993 Dubrul et al.
5,188,118 A 2/1993 Terwilliger
5,192,327 A 3/1993 Brantigan
5,195,506 A 3/1993 Hulfish
5,201,742 A 4/1993 Hasson
5,217,462 A 6/1993 Asnis et al.
5,217,475 A 6/1993 Kuber
5,217,486 A 6/1993 Rice et al.
5,224,952 A 7/1993 Deniega et al.
5,228,441 A 7/1993 Lundquist
5,234,431 A 8/1993 Keller
5,241,972 A 9/1993 Bonati
5,242,410 A 9/1993 Melker
5,242,447 A 9/1993 Borzone
5,242,448 A 9/1993 Pettine et al.
5,242,879 A 9/1993 Abe et al.
5,246,441 A 9/1993 Ross et al.
5,250,049 A 10/1993 Michael
5,250,061 A 10/1993 Michelson
5,257,632 A 11/1993 Turkel et al.
5,263,953 A 11/1993 Bagby
5,269,797 A 12/1993 Bonati et al.
5,280,782 A 1/1994 Wilk
5,285,795 A 2/1994 Ryan et al.
5,286,001 A 2/1994 Rafeld
5,290,243 A 3/1994 Chodorow et al.
5,290,312 A 3/1994 Kojimoto et al.
5,300,074 A 4/1994 Frigg
5,303,718 A 4/1994 Krajicek
5,304,142 A 4/1994 Liebl et al.
5,306,307 A 4/1994 Senter et al.
5,306,308 A 4/1994 Gross et al.
5,306,309 A 4/1994 Wagner et al.
5,306,310 A 4/1994 Siebels
5,308,327 A 5/1994 Heaven et al.
5,308,352 A 5/1994 Koutrouvelis
5,312,410 A 5/1994 Miller et al.
5,312,417 A 5/1994 Wilk
5,314,477 A 5/1994 Marnay
5,320,644 A 6/1994 Baumgartner
5,322,505 A 6/1994 Krause et al.
5,324,261 A 6/1994 Amundson et al.
5,330,429 A 7/1994 Noguchi et al.
5,331,975 A 7/1994 Bonutti
5,334,184 A 8/1994 Bimman
5,334,204 A 8/1994 Clewett et al.
5,342,365 A 8/1994 Waldman
5,342,382 A 8/1994 Brinkerhoff et al.
5,344,252 A 9/1994 Kakimoto
5,361,752 A 11/1994 Moll et al.
5,364,398 A 11/1994 Chapman et al.
5,370,646 A 12/1994 Reese et al.
5,370,647 A 12/1994 Graber et al.
5,370,661 A 12/1994 Branch
5,370,697 A 12/1994 Baumgartner
5,372,660 A 12/1994 Davidson et al.
5,374,267 A 12/1994 Siegal
5,382,248 A 1/1995 Jacobson et al.
5,383,932 A 1/1995 Wilson et al.
5,385,151 A 1/1995 Scarfone et al.
5,387,213 A 2/1995 Breard et al.
5,387,215 A 2/1995 Fisher
5,390,683 A 2/1995 Pisharodi
5,395,317 A 3/1995 Kambin
5,395,371 A 3/1995 Miller et al.
5,397,364 A 3/1995 Kozak et al.
5,401,269 A 3/1995 Buttner-Janz et al.
5,407,430 A 4/1995 Peters
5,410,016 A 4/1995 Hubbell et al.
5,415,661 A 5/1995 Holmes
5,423,816 A 6/1995 Lin
5,423,817 A 6/1995 Lin
5,423,850 A 6/1995 Berger
5,424,773 A 6/1995 Saito
5,425,773 A 6/1995 Boyd et al.
5,431,658 A 7/1995 Moskovich
5,441,538 A 8/1995 Bonutti
5,443,514 A 8/1995 Steffee
5,449,359 A 9/1995 Groiso
5,449,361 A 9/1995 Preissman
5,452,748 A 9/1995 Simmons et al.
5,454,365 A 10/1995 Bonutti
5,454,790 A 10/1995 Dubrul
5,454,815 A 10/1995 Geisser et al.
5,454,827 A 10/1995 Aust et al.
5,456,686 A 10/1995 Klapper et al.
5,458,641 A 10/1995 Ramirez Jimenez
5,458,643 A 10/1995 Oka et al.
5,462,563 A 10/1995 Shearer et al.
5,464,427 A 11/1995 Curtis et al.
5,464,929 A 11/1995 Bezwada et al.
5,468,245 A 11/1995 Vargas, III
5,470,333 A 11/1995 Ray
5,472,426 A 12/1995 Bonati et al.
5,474,539 A 12/1995 Costa et al.
5,480,400 A 1/1996 Berger
5,484,437 A 1/1996 Michelson
5,486,190 A 1/1996 Green

(56) References Cited

U.S. PATENT DOCUMENTS

| | | | |
|---|---|---|---|
| 5,496,318 | A | 3/1996 | Howland et al. |
| 5,498,265 | A | 3/1996 | Asnis et al. |
| 5,501,695 | A | 3/1996 | Anspach et al. |
| 5,505,710 | A | 4/1996 | Dorsey, III |
| 5,507,816 | A | 4/1996 | Bullivant |
| 5,509,923 | A | 4/1996 | Middleman et al. |
| 5,512,037 | A | 4/1996 | Russell et al. |
| 5,514,143 | A | 5/1996 | Bonutti et al. |
| 5,514,153 | A | 5/1996 | Bonutti |
| 5,514,180 | A | 5/1996 | Heggeness et al. |
| 5,520,690 | A | 5/1996 | Errico et al. |
| 5,520,896 | A | 5/1996 | De et al. |
| 5,522,398 | A | 6/1996 | Goldenberg et al. |
| 5,522,790 | A | 6/1996 | Moll et al. |
| 5,522,846 | A | 6/1996 | Bonutti |
| 5,522,895 | A | 6/1996 | Mikos |
| 5,522,899 | A | 6/1996 | Michelson |
| 5,527,312 | A | 6/1996 | Ray |
| 5,527,343 | A | 6/1996 | Bonutti |
| 5,527,624 | A | 6/1996 | Higgins et al. |
| 5,531,856 | A | 7/1996 | Moll et al. |
| 5,534,023 | A | 7/1996 | Henley |
| 5,534,029 | A | 7/1996 | Shima |
| 5,534,030 | A | 7/1996 | Navarro et al. |
| 5,536,127 | A | 7/1996 | Pennig |
| 5,538,009 | A | 7/1996 | Byrne et al. |
| 5,540,688 | A | 7/1996 | Navas |
| 5,540,693 | A | 7/1996 | Fisher |
| 5,540,711 | A | 7/1996 | Kieturakis et al. |
| 5,545,164 | A | 8/1996 | Howland |
| 5,545,222 | A | 8/1996 | Bonutti |
| 5,549,610 | A | 8/1996 | Russell et al. |
| 5,549,679 | A | 8/1996 | Kuslich |
| 5,554,191 | A | 9/1996 | Lahille et al. |
| 5,556,431 | A | 9/1996 | Buttner-Janz |
| 5,558,674 | A | 9/1996 | Heggeness et al. |
| D374,287 | S | 10/1996 | Goble et al. |
| 5,562,736 | A | 10/1996 | Ray et al. |
| 5,562,738 | A | 10/1996 | Boyd et al. |
| 5,564,926 | A | 10/1996 | Braanemark |
| 5,569,248 | A | 10/1996 | Mathews |
| 5,569,251 | A | 10/1996 | Baker et al. |
| 5,569,290 | A | 10/1996 | McAfee |
| 5,569,548 | A | 10/1996 | Koike et al. |
| 5,571,109 | A | 11/1996 | Bertagnoli |
| 5,571,189 | A | 11/1996 | Kuslich |
| 5,571,190 | A | 11/1996 | Ulrich et al. |
| 5,575,790 | A | 11/1996 | Chen et al. |
| 5,591,168 | A | 1/1997 | Judet et al. |
| 5,593,409 | A | 1/1997 | Michelson |
| 5,595,751 | A | 1/1997 | Bezwada et al. |
| 5,597,579 | A | 1/1997 | Bezwada et al. |
| 5,601,556 | A | 2/1997 | Pisharodi |
| 5,601,561 | A | 2/1997 | Terry et al. |
| 5,601,572 | A | 2/1997 | Middleman et al. |
| 5,607,687 | A | 3/1997 | Bezwada et al. |
| 5,609,634 | A | 3/1997 | Voydeville |
| 5,609,635 | A | 3/1997 | Michelson |
| 5,609,636 | A | 3/1997 | Kohrs et al. |
| 5,613,950 | A | 3/1997 | Yoon |
| 5,618,142 | A | 4/1997 | Sonden et al. |
| 5,618,314 | A | 4/1997 | Harwin et al. |
| 5,618,552 | A | 4/1997 | Bezwada et al. |
| 5,620,698 | A | 4/1997 | Bezwada et al. |
| 5,624,447 | A | 4/1997 | Myers |
| 5,626,613 | A | 5/1997 | Schmieding |
| 5,628,751 | A | 5/1997 | Sander et al. |
| 5,628,752 | A | 5/1997 | Asnis et al. |
| 5,632,746 | A | 5/1997 | Middleman et al. |
| 5,639,276 | A | 6/1997 | Weinstock et al. |
| 5,643,320 | A | 7/1997 | Lower et al. |
| 5,645,589 | A | 7/1997 | Li |
| 5,645,596 | A | 7/1997 | Kim et al. |
| 5,645,597 | A | 7/1997 | Krapiva |
| 5,645,599 | A | 7/1997 | Samani |
| 5,645,850 | A | 7/1997 | Bezwada et al. |
| 5,647,857 | A | 7/1997 | Anderson et al. |
| 5,648,088 | A | 7/1997 | Bezwada et al. |
| 5,649,931 | A | 7/1997 | Bryant et al. |
| 5,653,763 | A | 8/1997 | Errico et al. |
| 5,658,335 | A | 8/1997 | Allen |
| 5,662,683 | A | 9/1997 | Kay |
| 5,665,095 | A | 9/1997 | Jacobson et al. |
| 5,665,122 | A | 9/1997 | Kambin |
| 5,667,508 | A | 9/1997 | Errico et al. |
| 5,669,915 | A | 9/1997 | Caspar et al. |
| 5,669,926 | A | 9/1997 | Aust et al. |
| 5,674,294 | A | 10/1997 | Bainville et al. |
| 5,674,295 | A | 10/1997 | Ray et al. |
| 5,674,296 | A | 10/1997 | Bryan et al. |
| 5,676,701 | A | 10/1997 | Yuan et al. |
| 5,679,723 | A | 10/1997 | Cooper et al. |
| 5,681,263 | A | 10/1997 | Flesch |
| 5,683,465 | A | 11/1997 | Shinn et al. |
| 5,693,100 | A | 12/1997 | Pisharodi |
| 5,695,513 | A | 12/1997 | Johnson et al. |
| 5,697,977 | A | 12/1997 | Pisharodi |
| 5,698,213 | A | 12/1997 | Jamiolkowski et al. |
| 5,700,239 | A | 12/1997 | Yoon |
| 5,700,583 | A | 12/1997 | Jamiolkowski et al. |
| 5,702,391 | A | 12/1997 | Lin |
| 5,702,449 | A | 12/1997 | McKay |
| 5,702,450 | A | 12/1997 | Bisserie |
| 5,702,453 | A | 12/1997 | Rabbe et al. |
| 5,702,454 | A | 12/1997 | Baumgartner |
| 5,707,359 | A | 1/1998 | Bufalini |
| 5,713,870 | A | 2/1998 | Yoon |
| 5,713,903 | A | 2/1998 | Sander et al. |
| 5,716,415 | A | 2/1998 | Steffee |
| 5,716,416 | A | 2/1998 | Lin |
| 5,720,753 | A | 2/1998 | Sander et al. |
| 5,725,531 | A | 3/1998 | Shapiro |
| 5,725,541 | A | 3/1998 | Anspach et al. |
| 5,725,588 | A | 3/1998 | Errico et al. |
| 5,728,097 | A | 3/1998 | Mathews |
| 5,728,116 | A | 3/1998 | Rosenman |
| 5,735,853 | A | 4/1998 | Olerud |
| 5,741,253 | A | 4/1998 | Michelson |
| 5,741,282 | A | 4/1998 | Anspach et al. |
| 5,743,881 | A | 4/1998 | Demco |
| 5,743,912 | A | 4/1998 | Lahille et al. |
| 5,743,914 | A | 4/1998 | Skiba |
| 5,749,879 | A | 5/1998 | Middleman et al. |
| 5,749,889 | A | 5/1998 | Bacich et al. |
| 5,752,969 | A | 5/1998 | Cunci et al. |
| 5,755,797 | A | 5/1998 | Baumgartner |
| 5,755,798 | A | 5/1998 | Papavero et al. |
| 5,756,127 | A | 5/1998 | Grisoni et al. |
| 5,762,500 | A | 6/1998 | Lazarof |
| 5,762,629 | A | 6/1998 | Kambin |
| 5,766,252 | A | 6/1998 | Henry et al. |
| 5,772,661 | A | 6/1998 | Michelson |
| 5,772,662 | A | 6/1998 | Chapman et al. |
| 5,772,678 | A | 6/1998 | Thomason et al. |
| 5,776,156 | A | 7/1998 | Shikhman |
| 5,782,800 | A | 7/1998 | Yoon |
| 5,782,832 | A | 7/1998 | Larsen et al. |
| 5,782,865 | A | 7/1998 | Grotz |
| 5,788,703 | A | 8/1998 | Mittelmeier et al. |
| 5,792,044 | A | 8/1998 | Foley et al. |
| 5,797,909 | A | 8/1998 | Michelson |
| 5,800,549 | A | 9/1998 | Bao et al. |
| 5,807,275 | A | 9/1998 | Jamshidi |
| 5,807,327 | A | 9/1998 | Green et al. |
| 5,810,721 | A | 9/1998 | Mueller et al. |
| 5,810,821 | A | 9/1998 | Vandewalle |
| 5,810,866 | A | 9/1998 | Yoon |
| 5,814,084 | A | 9/1998 | Grivas et al. |
| 5,820,628 | A | 10/1998 | Middleman et al. |
| 5,823,979 | A | 10/1998 | Mezo |
| 5,824,084 | A | 10/1998 | Muschler |
| 5,824,093 | A | 10/1998 | Ray et al. |
| 5,824,094 | A | 10/1998 | Serhan et al. |
| 5,827,289 | A | 10/1998 | Reiley et al. |

(56) References Cited

U.S. PATENT DOCUMENTS 5,833,657 A 11/1998 Reinhardt et al.
5,836,948 A 11/1998 Zucherman et al.
5,837,752 A 11/1998 Shastri et al.
5,846,259 A 12/1998 Berthiaume
5,848,986 A 12/1998 Lundquist et al.
5,849,004 A 12/1998 Bramlet
5,851,212 A 12/1998 Zirps et al.
5,851,216 A 12/1998 Allen
5,857,995 A 1/1999 Thomas et al.
5,859,150 A 1/1999 Jamiolkowski et al.
5,860,973 A 1/1999 Michelson
5,860,977 A 1/1999 Zucherman et al.
5,865,846 A 2/1999 Bryan et al.
5,865,848 A 2/1999 Baker
5,871,485 A 2/1999 Rao et al.
5,873,854 A 2/1999 Wolvek
5,876,404 A 3/1999 Zucherman et al.
5,888,220 A 3/1999 Felt et al.
5,888,221 A 3/1999 Gelbard
5,888,223 A 3/1999 Bray, Jr.
5,888,224 A 3/1999 Beckers et al.
5,888,226 A 3/1999 Rogozinski
5,888,227 A 3/1999 Cottle
5,888,228 A 3/1999 Knothe et al.
5,893,850 A 4/1999 Cachia
5,893,889 A 4/1999 Harrington
5,893,890 A 4/1999 Pisharodi
5,895,428 A 4/1999 Berry
5,902,231 A 5/1999 Foley et al.
5,904,690 A 5/1999 Middleman et al.
5,904,696 A 5/1999 Rosenman
5,908,422 A 6/1999 Bresina
5,916,228 A 6/1999 Ripich et al.
5,916,267 A 6/1999 Tienboon
5,919,235 A 7/1999 Husson et al.
5,925,056 A 7/1999 Thomas et al.
5,925,074 A 7/1999 Gingras et al.
5,928,235 A 7/1999 Friedl
5,928,244 A 7/1999 Tovey et al.
5,931,870 A 8/1999 Cuckler et al.
5,935,129 A 8/1999 McDevitt et al.
5,947,999 A 9/1999 Groiso
5,948,000 A 9/1999 Larsen et al.
5,954,722 A 9/1999 Bono
5,954,747 A 9/1999 Clark
5,957,902 A 9/1999 Teves
5,957,924 A 9/1999 Toermaelae et al.
5,961,554 A 10/1999 Janson et al.
5,964,730 A 10/1999 Williams et al.
5,964,761 A 10/1999 Kambin
5,967,783 A 10/1999 Ura
5,967,970 A 10/1999 Cowan et al.
5,968,044 A 10/1999 Nicholson et al.
5,968,098 A 10/1999 Winslow
5,972,015 A 10/1999 Scribner et al.
5,972,385 A 10/1999 Liu et al.
5,976,139 A 11/1999 Bramlet
5,976,146 A 11/1999 Ogawa et al.
5,976,186 A 11/1999 Bao et al.
5,976,187 A 11/1999 Richelsoph
5,980,522 A 11/1999 Koros et al.
5,984,927 A 11/1999 Wenstrom et al.
5,984,966 A 11/1999 Kiema et al.
5,985,307 A 11/1999 Hanson et al.
5,989,255 A 11/1999 Pepper et al.
5,989,291 A 11/1999 Ralph et al.
5,993,459 A 11/1999 Larsen et al.
5,997,510 A 12/1999 Schwemberger
5,997,538 A 12/1999 Asnis et al.
5,997,541 A 12/1999 Schenk
6,001,100 A 12/1999 Sherman et al.
6,001,101 A 12/1999 Augagneur et al.
6,004,327 A 12/1999 Asnis et al.
6,005,161 A 12/1999 Brekke
6,007,519 A 12/1999 Rosselli
6,007,566 A 12/1999 Wenstrom, Jr.
6,007,580 A 12/1999 Lehto et al.
6,010,508 A 1/2000 Bradley
6,010,513 A 1/2000 Toermaelae et al.
6,012,494 A 1/2000 Balazs
6,015,410 A 1/2000 Toermaelae et al.
6,015,436 A 1/2000 Schoenhoeffer
6,019,762 A 2/2000 Cole
6,019,792 A 2/2000 Cauthen
6,019,793 A 2/2000 Perren et al.
6,022,350 A 2/2000 Ganem
6,022,352 A 2/2000 Vandewalle
6,030,162 A 2/2000 Huebner
6,030,364 A 2/2000 Durgin et al.
6,030,401 A 2/2000 Marino
6,033,406 A 3/2000 Mathews
6,033,412 A 3/2000 Losken et al.
6,036,701 A 3/2000 Rosenman
6,039,740 A 3/2000 Olerud
6,039,761 A 3/2000 Li
6,039,763 A 3/2000 Shelokov
6,045,552 A 4/2000 Zucherman et al.
6,045,579 A 4/2000 Hochshuler
6,048,309 A 4/2000 Flom et al.
6,048,342 A 4/2000 Zucherman et al.
6,048,346 A 4/2000 Reiley et al.
6,048,360 A 4/2000 Khosravi et al.
6,049,026 A 4/2000 Muschler
6,053,922 A 4/2000 Krause et al.
6,053,935 A 4/2000 Brenneman et al.
6,056,763 A 5/2000 Parsons
6,063,121 A 5/2000 Xavier et al.
6,066,142 A 5/2000 Serbousek et al.
6,066,154 A 5/2000 Reiley et al.
6,066,175 A 5/2000 Henderson et al.
6,068,630 A 5/2000 Zucherman et al.
6,068,648 A 5/2000 Cole et al.
6,071,982 A 6/2000 Wise et al.
6,073,051 A 6/2000 Sharkey et al.
6,074,390 A 6/2000 Zucherman et al.
6,080,155 A 6/2000 Michelson
6,080,158 A 6/2000 Lin
6,080,193 A 6/2000 Hochschuler et al.
6,083,225 A 7/2000 Winslow et al.
6,083,244 A 7/2000 Lubbers et al.
6,090,112 A 7/2000 Zucherman et al.
6,090,143 A 7/2000 Meriwether et al.
6,096,038 A 8/2000 Michelson
6,096,080 A 8/2000 Nicholson et al.
6,099,531 A 8/2000 Bonutti
6,102,914 A 8/2000 Bulstra et al.
6,102,950 A 8/2000 Vaccaro
6,106,557 A 8/2000 Robioneck et al.
6,110,210 A 8/2000 Norton et al.
6,113,624 A 9/2000 Bezwada et al.
6,113,637 A 9/2000 Gill et al.
6,113,638 A 9/2000 Williams et al.
6,113,640 A 9/2000 Toermaelae et al.
6,117,174 A 9/2000 Nolan
6,119,044 A 9/2000 Kuzma
6,120,508 A 9/2000 Gruenig et al.
6,123,705 A 9/2000 Michelson
6,123,711 A 9/2000 Winters
6,126,660 A 10/2000 Dietz
6,126,661 A 10/2000 Faccioli et al.
6,126,663 A 10/2000 Hair
6,126,686 A 10/2000 Badylak et al.
6,126,689 A 10/2000 Brett
6,127,597 A 10/2000 Beyar et al.
6,129,762 A 10/2000 Li
6,129,763 A 10/2000 Chauvin et al.
6,132,435 A 10/2000 Young
6,136,031 A 10/2000 Middleton
6,139,558 A 10/2000 Wagner
6,139,579 A 10/2000 Steffee et al.
6,146,384 A 11/2000 Lee et al.
6,146,387 A 11/2000 Trott et al.
6,146,420 A 11/2000 McKay
6,146,421 A 11/2000 Gordon et al.

(56) References Cited

U.S. PATENT DOCUMENTS 6,147,135 A 11/2000 Yuan et al.
6,149,652 A 11/2000 Zucherman et al.
6,152,926 A 11/2000 Zucherman et al.
6,156,038 A 12/2000 Zucherman et al.
6,159,179 A 12/2000 Simonson
6,159,211 A 12/2000 Boriani et al.
6,159,244 A 12/2000 Suddaby
6,161,350 A 12/2000 Espinosa
6,162,234 A 12/2000 Freedland et al.
6,162,236 A 12/2000 Osada
6,162,252 A 12/2000 Kuras et al.
6,165,218 A 12/2000 Husson et al.
6,165,486 A 12/2000 Marra et al.
6,168,595 B1 1/2001 Durham et al.
6,168,597 B1 1/2001 Biedermann et al.
6,171,610 B1 1/2001 Vacanti et al.
6,174,337 B1 1/2001 Keenan
6,175,758 B1 1/2001 Kambin
6,176,882 B1 1/2001 Biedermann et al. .. A61F 2/447 623/17.11
6,179,794 B1 1/2001 Burras
6,179,873 B1 1/2001 Zientek
6,183,471 B1 2/2001 Zucherman et al.
6,183,472 B1 2/2001 Lutz
6,183,474 B1 2/2001 Bramlet et al.
6,183,517 B1 2/2001 Suddaby
6,187,043 B1 2/2001 Ledergerber
6,187,048 B1 2/2001 Milner et al.
6,190,387 B1 2/2001 Zucherman et al.
6,190,414 B1 2/2001 Young et al.
6,193,757 B1 2/2001 Foley et al.
6,197,033 B1 3/2001 Haid et al.
6,197,041 B1 3/2001 Shichman et al.
6,197,065 B1 3/2001 Martin et al.
6,197,325 B1 3/2001 MacPhee et al.
6,200,322 B1 3/2001 Branch et al.
6,203,565 B1 3/2001 Bonutti et al.
6,206,826 B1 3/2001 Mathews et al.
6,206,922 B1 3/2001 Zdeblick et al.
D439,980 S 4/2001 Reiley et al.
6,213,957 B1 4/2001 Milliman et al.
6,214,368 B1 4/2001 Lee et al.
6,217,509 B1 4/2001 Foley et al.
6,217,579 B1 4/2001 Koros
6,221,082 B1 4/2001 Marino et al.
6,224,603 B1 5/2001 Marino
6,224,631 B1 5/2001 Kohrs
6,224,894 B1 5/2001 Jamiolkowski et al.
6,228,058 B1 5/2001 Dennis et al.
6,231,606 B1 5/2001 Graf et al.
6,235,030 B1 5/2001 Zucherman et al.
6,235,043 B1 5/2001 Reiley et al.
6,238,397 B1 5/2001 Zucherman et al.
6,238,491 B1 5/2001 Davidson et al.
6,241,733 B1 6/2001 Nicholson et al.
6,241,734 B1 6/2001 Scribner et al.
6,241,769 B1 6/2001 Nicholson et al.
6,245,107 B1 6/2001 Ferree
6,248,108 B1 6/2001 Toermaelae et al.
6,248,110 B1 6/2001 Reiley et al.
6,248,131 B1 6/2001 Felt et al.
6,251,111 B1 6/2001 Barker et al.
6,251,140 B1 6/2001 Marino et al.
6,258,093 B1 7/2001 Edwards et al.
6,261,289 B1 7/2001 Levy
6,264,676 B1 7/2001 Gellman et al.
6,264,695 B1 7/2001 Stoy
6,267,763 B1 7/2001 Castro
6,267,765 B1 7/2001 Taylor et al.
6,267,767 B1 7/2001 Strobel et al.
6,277,149 B1 8/2001 Boyle et al.
6,280,444 B1 8/2001 Zucherman et al.
6,280,456 B1 8/2001 Scribner et al.
6,280,474 B1 8/2001 Cassidy et al.
6,280,475 B1 8/2001 Bao et al.
6,287,313 B1 9/2001 Sasso
6,290,724 B1 9/2001 Marino
6,293,909 B1 9/2001 Chu et al.
6,293,952 B1 9/2001 Brosens et al.
D449,691 S 10/2001 Reiley et al.
6,296,644 B1 10/2001 Saurat et al.
6,296,647 B1 10/2001 Robioneck et al.
6,302,914 B1 10/2001 Michelson
6,306,136 B1 10/2001 Baccelli
6,306,177 B1 10/2001 Felt et al.
D450,676 S 11/2001 Huttner
6,312,443 B1 11/2001 Stone
6,319,254 B1 11/2001 Giet et al.
6,319,272 B1 11/2001 Brenneman et al.
6,331,312 B1 12/2001 Lee et al.
6,332,882 B1 12/2001 Zucherman et al.
6,332,883 B1 12/2001 Zucherman et al.
6,332,894 B1 12/2001 Stalcup et al.
6,332,895 B1 12/2001 Suddaby
6,342,074 B1 1/2002 Simpson
6,346,092 B1 2/2002 Leschinsky
6,348,053 B1 2/2002 Cachia
6,355,043 B1 3/2002 Adam
6,361,537 B1 3/2002 Anderson
6,361,538 B1 3/2002 Fenaroli et al.
6,361,557 B1 3/2002 Gittings et al.
6,364,828 B1 4/2002 Yeung et al.
6,364,897 B1 4/2002 Bonutti
6,368,325 B1 4/2002 McKinley et al.
6,368,350 B1 4/2002 Erickson et al.
6,368,351 B1 4/2002 Glenn
6,371,971 B1 4/2002 Tsugita et al.
6,371,989 B1 4/2002 Chauvin et al.
6,375,681 B1 4/2002 Truscott
6,375,682 B1 4/2002 Fleischmann et al.
6,375,683 B1 4/2002 Crozet et al.
6,379,355 B1 4/2002 Zucherman et al.
6,379,363 B1 4/2002 Herrington et al.
6,387,130 B1 5/2002 Stone
6,398,793 B1 6/2002 McGuire
6,402,750 B1 6/2002 Atkinson et al.
6,409,766 B1 6/2002 Brett
6,409,767 B1 6/2002 Perice et al.
6,413,278 B1 7/2002 Marchosky
6,416,551 B1 7/2002 Keller
6,419,641 B1 7/2002 Mark et al.
6,419,676 B1 7/2002 Zucherman et al.
6,419,677 B2 7/2002 Zucherman et al.
6,419,704 B1 7/2002 Ferree
6,419,705 B1 7/2002 Erickson
6,419,706 B1 7/2002 Graf
6,423,061 B1 7/2002 Bryant
6,423,067 B1 7/2002 Eisermann
6,423,071 B1 7/2002 Lawson
6,423,083 B2 7/2002 Reiley et al.
6,423,089 B1 7/2002 Gingras et al.
6,425,887 B1 7/2002 McGuckin et al.
6,425,919 B1 7/2002 Lambrecht
6,425,920 B1 7/2002 Hamada
6,428,541 B1 8/2002 Boyd et al.
6,428,556 B1 8/2002 Chin
6,436,101 B1 8/2002 Hamada
6,436,140 B1 8/2002 Liu et al.
6,436,143 B1 8/2002 Ross et al.
6,440,138 B1 8/2002 Reiley et al.
6,440,154 B2 8/2002 Gellman et al.
6,440,169 B1 8/2002 Elberg et al.
6,443,989 B1 9/2002 Jackson
6,447,518 B1 9/2002 Krause et al.
6,447,527 B1 9/2002 Thompson et al.
6,447,540 B1 9/2002 Fontaine et al.
6,450,989 B2 9/2002 Dubrul et al.
6,451,019 B1 9/2002 Zucherman et al.
6,451,020 B1 9/2002 Zucherman et al.
6,454,806 B1 9/2002 Cohen et al.
6,454,807 B1 9/2002 Jackson
6,458,134 B1 10/2002 Songer et al.
6,461,359 B1 10/2002 Tribus et al.
6,468,277 B1 10/2002 Justin et al.

(56) References Cited

U.S. PATENT DOCUMENTS

| | | | |
|---|---|---|---|
| 6,468,279 | B1 | 10/2002 | Reo |
| 6,468,309 | B1 | 10/2002 | Lieberman |
| 6,468,310 | B1 | 10/2002 | Ralph et al. |
| 6,471,724 | B2 | 10/2002 | Zdeblick et al. |
| 6,475,226 | B1 | 11/2002 | Belef et al. |
| 6,478,029 | B1 | 11/2002 | Boyd et al. |
| 6,478,796 | B2 | 11/2002 | Zucherman et al. |
| 6,478,805 | B1 | 11/2002 | Marino et al. |
| 6,482,235 | B1 | 11/2002 | Lambrecht et al. |
| 6,485,491 | B1 | 11/2002 | Farris et al. |
| 6,485,518 | B1 | 11/2002 | Cornwall et al. |
| D467,657 | S | 12/2002 | Scribner |
| 6,488,693 | B2 | 12/2002 | Gannoe et al. |
| 6,488,710 | B2 | 12/2002 | Besselink |
| 6,489,309 | B1 | 12/2002 | Singh et al. |
| 6,491,626 | B1 | 12/2002 | Stone et al. |
| 6,491,695 | B1 | 12/2002 | Roggenbuck |
| 6,491,714 | B1 | 12/2002 | Bennett |
| 6,491,724 | B1 | 12/2002 | Ferree |
| 6,494,860 | B2 | 12/2002 | Rocamora et al. |
| 6,494,883 | B1 | 12/2002 | Ferree |
| 6,494,893 | B2 | 12/2002 | Dubrul et al. |
| 6,498,421 | B1 | 12/2002 | Oh et al. |
| 6,500,178 | B2 | 12/2002 | Zucherman et al. |
| 6,500,205 | B1 | 12/2002 | Michelson |
| 6,506,192 | B1 | 1/2003 | Gertzman et al. |
| 6,508,839 | B1 | 1/2003 | Lambrecht et al. |
| 6,511,471 | B2 | 1/2003 | Rosenman et al. |
| 6,511,481 | B2 | 1/2003 | Von et al. |
| 6,512,958 | B1 | 1/2003 | Swoyer et al. |
| D469,871 | S | 2/2003 | Sand |
| 6,514,256 | B2 | 2/2003 | Zucherman et al. |
| 6,517,543 | B1 | 2/2003 | Berrevoets et al. |
| 6,517,580 | B1 | 2/2003 | Ramadan et al. |
| 6,520,907 | B1 | 2/2003 | Foley et al. |
| 6,520,991 | B2 | 2/2003 | Huene |
| D472,323 | S | 3/2003 | Sand |
| 6,527,774 | B2 | 3/2003 | Lieberman |
| 6,527,803 | B1 | 3/2003 | Crozet et al. |
| 6,527,804 | B1 | 3/2003 | Gauchet et al. |
| 6,530,930 | B1 | 3/2003 | Marino et al. |
| 6,533,791 | B1 | 3/2003 | Betz et al. |
| 6,533,797 | B1 | 3/2003 | Stone et al. |
| 6,533,818 | B1 | 3/2003 | Weber et al. |
| 6,540,747 | B1 | 4/2003 | Marino |
| 6,544,265 | B2 | 4/2003 | Lieberman |
| 6,547,793 | B1 | 4/2003 | McGuire |
| 6,547,795 | B2 | 4/2003 | Schneiderman |
| 6,547,823 | B2 | 4/2003 | Scarborough et al. |
| 6,551,319 | B2 | 4/2003 | Lieberman |
| 6,551,322 | B1 | 4/2003 | Lieberman |
| 6,554,831 | B1 | 4/2003 | Rivard et al. |
| 6,554,833 | B2 | 4/2003 | Levy et al. |
| 6,554,852 | B1 | 4/2003 | Oberlander |
| 6,558,389 | B2 | 5/2003 | Clark et al. |
| 6,558,390 | B2 | 5/2003 | Cragg |
| 6,558,424 | B2 | 5/2003 | Thalgott |
| 6,562,046 | B2 | 5/2003 | Sasso |
| 6,562,049 | B1 | 5/2003 | Norlander et al. |
| 6,562,072 | B1 | 5/2003 | Fuss et al. |
| 6,562,074 | B2 | 5/2003 | Gerbec et al. |
| 6,575,919 | B1 | 6/2003 | Reiley et al. |
| 6,575,979 | B1 | 6/2003 | Cragg |
| 6,576,016 | B1 | 6/2003 | Hochshuler et al. |
| 6,579,291 | B1 | 6/2003 | Keith et al. |
| 6,579,293 | B1 | 6/2003 | Chandran |
| 6,579,320 | B1 | 6/2003 | Gauchet et al. |
| 6,579,321 | B1 | 6/2003 | Gordon et al. |
| 6,582,390 | B1 | 6/2003 | Sanderson |
| 6,582,431 | B1 | 6/2003 | Ray |
| 6,582,433 | B2 | 6/2003 | Yun |
| 6,582,437 | B2 | 6/2003 | Dorchak et al. |
| 6,582,441 | B1 | 6/2003 | He et al. |
| 6,582,453 | B1 | 6/2003 | Tran et al. |
| 6,582,466 | B1 | 6/2003 | Gauchet |
| 6,582,467 | B1 | 6/2003 | Teitelbaum et al. |
| 6,582,468 | B1 | 6/2003 | Gauchet |
| 6,585,730 | B1 | 7/2003 | Foerster |
| 6,585,740 | B2 | 7/2003 | Schlapfer et al. |
| 6,589,240 | B2 | 7/2003 | Hinchliffe |
| 6,589,249 | B2 | 7/2003 | Sater et al. |
| 6,592,553 | B2 | 7/2003 | Zhang et al. |
| 6,592,624 | B1 | 7/2003 | Fraser et al. |
| 6,592,625 | B2 | 7/2003 | Cauthen |
| 6,595,998 | B2 | 7/2003 | Johnson et al. |
| 6,596,008 | B1 | 7/2003 | Kambin |
| 6,599,294 | B2 | 7/2003 | Fuss et al. |
| 6,599,297 | B1 | 7/2003 | Carlsson et al. |
| 6,602,293 | B1 | 8/2003 | Biermann et al. |
| 6,607,530 | B1 | 8/2003 | Carl et al. |
| 6,607,544 | B1 | 8/2003 | Boucher et al. |
| 6,607,558 | B2 | 8/2003 | Kuras |
| 6,610,066 | B2 | 8/2003 | Dinger et al. |
| 6,610,091 | B1 | 8/2003 | Reiley |
| 6,610,094 | B2 | 8/2003 | Husson |
| 6,613,050 | B1 | 9/2003 | Wagner et al. |
| 6,613,054 | B2 | 9/2003 | Scribner et al. |
| 6,616,678 | B2 | 9/2003 | Nishtala et al. |
| 6,620,196 | B1 | 9/2003 | Trieu |
| 6,623,505 | B2 | 9/2003 | Scribner et al. |
| 6,626,943 | B2 | 9/2003 | Eberlein et al. |
| 6,626,944 | B1 | 9/2003 | Taylor |
| 6,629,998 | B1 | 10/2003 | Lin |
| 6,632,224 | B2 | 10/2003 | Cachia et al. |
| 6,632,235 | B2 | 10/2003 | Weikel et al. |
| 6,635,059 | B2 | 10/2003 | Randall et al. |
| 6,635,060 | B2 | 10/2003 | Hanson et al. |
| 6,635,362 | B2 | 10/2003 | Zheng |
| RE38,335 | E | 11/2003 | Aust et al. |
| D482,787 | S | 11/2003 | Reiss |
| 6,641,564 | B1 | 11/2003 | Kraus |
| 6,641,582 | B1 | 11/2003 | Hanson et al. |
| 6,641,587 | B2 | 11/2003 | Scribner et al. |
| 6,641,614 | B1 | 11/2003 | Wagner et al. |
| 6,645,213 | B2 | 11/2003 | Sand et al. |
| 6,645,248 | B2 | 11/2003 | Casutt |
| 6,648,890 | B2 | 11/2003 | Culbert et al. |
| 6,648,893 | B2 | 11/2003 | Dudasik |
| 6,648,917 | B2 | 11/2003 | Gerbec et al. |
| 6,652,527 | B2 | 11/2003 | Zucherman et al. |
| 6,652,592 | B1 | 11/2003 | Grooms et al. |
| D483,495 | S | 12/2003 | Sand |
| 6,655,962 | B1 | 12/2003 | Kennard |
| 6,656,178 | B1 | 12/2003 | Veldhuizen et al. |
| 6,656,180 | B2 | 12/2003 | Stahurski |
| 6,660,004 | B2 | 12/2003 | Barker et al. |
| 6,660,037 | B1 | 12/2003 | Husson et al. |
| 6,663,647 | B2 | 12/2003 | Reiley et al. |
| 6,666,890 | B2 | 12/2003 | Michelson |
| 6,666,891 | B2 | 12/2003 | Boehm et al. |
| 6,669,698 | B1 | 12/2003 | Tromanhauser et al. |
| 6,669,729 | B2 | 12/2003 | Chin |
| 6,669,732 | B2 | 12/2003 | Serhan et al. |
| 6,673,074 | B2 | 1/2004 | Shluzas |
| 6,676,663 | B2 | 1/2004 | Higueras et al. |
| 6,676,664 | B1 | 1/2004 | Al-Assir |
| 6,676,665 | B2 | 1/2004 | Foley et al. |
| 6,679,833 | B2 | 1/2004 | Smith et al. |
| 6,679,915 | B1 | 1/2004 | Cauthen |
| 6,682,535 | B2 | 1/2004 | Hoogland |
| 6,682,561 | B2 | 1/2004 | Songer et al. |
| 6,682,562 | B2 | 1/2004 | Viart et al. |
| 6,685,706 | B2 | 2/2004 | Padget et al. |
| 6,685,742 | B1 | 2/2004 | Jackson |
| 6,689,125 | B1 | 2/2004 | Keith et al. |
| 6,689,152 | B2 | 2/2004 | Balceta et al. |
| 6,689,168 | B2 | 2/2004 | Lieberman |
| 6,692,499 | B2 | 2/2004 | Toermaelae et al. |
| 6,692,563 | B2 | 2/2004 | Zimmermann |
| 6,695,842 | B2 | 2/2004 | Zucherman et al. |
| 6,695,851 | B2 | 2/2004 | Zdeblick et al. |
| 6,699,246 | B2 | 3/2004 | Zucherman et al. |
| 6,699,247 | B2 | 3/2004 | Zucherman et al. |
| 6,706,070 | B1 | 3/2004 | Wagner et al. |

(56) References Cited

U.S. PATENT DOCUMENTS

| | | | |
|---|---|---|---|
| 6,709,458 | B2 | 3/2004 | Michelson |
| 6,712,819 | B2 | 3/2004 | Zucherman et al. |
| 6,716,216 | B1 | 4/2004 | Boucher et al. |
| 6,716,247 | B2 | 4/2004 | Michelson |
| 6,716,957 | B2 | 4/2004 | Tunc |
| 6,719,760 | B2 | 4/2004 | Dorchak et al. |
| 6,719,761 | B1 | 4/2004 | Reiley et al. |
| 6,719,773 | B1 | 4/2004 | Boucher et al. |
| 6,719,796 | B2 | 4/2004 | Cohen et al. |
| 6,723,096 | B1 | 4/2004 | Dorchak et al. |
| 6,723,126 | B1 | 4/2004 | Berry |
| 6,723,127 | B2 | 4/2004 | Ralph et al. |
| 6,723,128 | B2 | 4/2004 | Uk |
| 6,726,691 | B2 | 4/2004 | Osorio et al. |
| D490,159 | S | 5/2004 | Sand |
| 6,730,126 | B2 | 5/2004 | Boehm et al. |
| 6,733,093 | B2 | 5/2004 | Deland et al. |
| 6,733,460 | B2 | 5/2004 | Ogura |
| 6,733,532 | B1 | 5/2004 | Gauchet et al. |
| 6,733,534 | B2 | 5/2004 | Sherman |
| 6,733,535 | B2 | 5/2004 | Michelson |
| 6,733,635 | B1 | 5/2004 | Ozawa et al. |
| 6,740,090 | B1 | 5/2004 | Cragg et al. |
| 6,740,093 | B2 | 5/2004 | Hochschuler et al. |
| 6,740,117 | B2 | 5/2004 | Ralph et al. |
| D492,032 | S | 6/2004 | Muller et al. |
| 6,743,166 | B2 | 6/2004 | Berci et al. |
| 6,743,255 | B2 | 6/2004 | Ferree |
| 6,746,451 | B2 | 6/2004 | Middleton et al. |
| 6,749,560 | B1 | 6/2004 | Konstorum et al. |
| 6,752,831 | B2 | 6/2004 | Sybert et al. |
| 6,755,837 | B2 | 6/2004 | Ebner |
| 6,755,841 | B2 | 6/2004 | Fraser et al. |
| D492,775 | S | 7/2004 | Doelling et al. |
| D493,533 | S | 7/2004 | Blain |
| 6,758,673 | B2 | 7/2004 | Fromovich et al. |
| 6,758,847 | B2 | 7/2004 | Maguire |
| 6,758,861 | B2 | 7/2004 | Ralph et al. |
| 6,758,862 | B2 | 7/2004 | Berry et al. |
| 6,761,720 | B1 | 7/2004 | Senegas |
| 6,764,491 | B2 | 7/2004 | Frey et al. |
| 6,764,514 | B1 | 7/2004 | Li et al. |
| D495,417 | S | 8/2004 | Doelling et al. |
| 6,770,075 | B2 | 8/2004 | Howland |
| 6,773,460 | B2 | 8/2004 | Jackson |
| 6,780,151 | B2 | 8/2004 | Grabover et al. |
| 6,783,530 | B1 | 8/2004 | Levy |
| 6,790,210 | B1 | 9/2004 | Cragg et al. |
| 6,793,656 | B1 | 9/2004 | Mathews |
| 6,793,678 | B2 | 9/2004 | Hawkins |
| 6,793,679 | B2 | 9/2004 | Michelson |
| 6,796,983 | B1 | 9/2004 | Zucherman et al. |
| 6,805,685 | B2 | 10/2004 | Taylor |
| 6,805,695 | B2 | 10/2004 | Keith et al. |
| 6,805,697 | B1 | 10/2004 | Helm et al. |
| 6,805,714 | B2 | 10/2004 | Sutcliffe |
| 6,808,526 | B1 | 10/2004 | Magerl et al. |
| 6,808,537 | B2 | 10/2004 | Michelson |
| 6,814,736 | B2 | 11/2004 | Reiley et al. |
| 6,814,756 | B1 | 11/2004 | Michelson |
| 6,821,298 | B1 | 11/2004 | Jackson |
| 6,824,565 | B2 | 11/2004 | Muhanna |
| 6,830,589 | B2 | 12/2004 | Erickson |
| 6,835,205 | B2 | 12/2004 | Atkinson et al. |
| 6,835,206 | B2 | 12/2004 | Jackson |
| 6,835,208 | B2 | 12/2004 | Marchosky |
| 6,840,941 | B2 | 1/2005 | Rogers et al. |
| 6,840,944 | B2 | 1/2005 | Suddaby |
| 6,852,126 | B2 | 2/2005 | Ahlgren |
| 6,852,127 | B2 | 2/2005 | Varga et al. |
| 6,852,129 | B2 | 2/2005 | Gerbec et al. |
| 6,855,167 | B2 | 2/2005 | Shimp |
| 6,863,668 | B2 | 3/2005 | Gillespie et al. |
| 6,863,672 | B2 | 3/2005 | Reiley et al. |
| 6,863,673 | B2 | 3/2005 | Gerbec et al. |
| 6,866,682 | B1 | 3/2005 | An et al. |
| 6,875,215 | B2 | 4/2005 | Taras et al. |
| 6,878,167 | B2 | 4/2005 | Ferree |
| 6,881,228 | B2 | 4/2005 | Zdeblick et al. |
| 6,881,229 | B2 | 4/2005 | Khandkar et al. |
| 6,883,520 | B2 | 4/2005 | Lambrecht et al. |
| 6,887,243 | B2 | 5/2005 | Culbert |
| 6,887,248 | B2 | 5/2005 | McKinley et al. |
| 6,890,333 | B2 | 5/2005 | Von et al. |
| 6,893,464 | B2 | 5/2005 | Kiester |
| 6,893,466 | B2 | 5/2005 | Trieu |
| 6,899,716 | B2 | 5/2005 | Cragg |
| 6,899,719 | B2 | 5/2005 | Reiley et al. |
| 6,899,735 | B2 | 5/2005 | Coates et al. |
| D506,828 | S | 6/2005 | Layne et al. |
| 6,902,566 | B2 | 6/2005 | Zucherman et al. |
| 6,905,512 | B2 | 6/2005 | Paes et al. |
| 6,908,465 | B2 | 6/2005 | Von et al. |
| 6,908,506 | B2 | 6/2005 | Zimmermann |
| 6,916,323 | B2 | 7/2005 | Kitchens |
| 6,921,403 | B2 | 7/2005 | Cragg et al. |
| 6,923,810 | B1 | 8/2005 | Michelson |
| 6,923,811 | B1 | 8/2005 | Carl et al. |
| 6,923,813 | B2 | 8/2005 | Phillips et al. |
| 6,923,814 | B1 | 8/2005 | Hildebrand et al. |
| 6,929,606 | B2 | 8/2005 | Ritland |
| 6,929,647 | B2 | 8/2005 | Cohen |
| 6,936,071 | B1 | 8/2005 | Marnay et al. |
| 6,936,072 | B2 | 8/2005 | Lambrecht et al. |
| 6,942,668 | B2 | 9/2005 | Padget et al. |
| 6,945,973 | B2 | 9/2005 | Bray |
| 6,945,975 | B2 | 9/2005 | Dalton |
| 6,946,000 | B2 | 9/2005 | Senegas et al. |
| 6,949,100 | B1 | 9/2005 | Venturini |
| 6,949,108 | B2 | 9/2005 | Holmes |
| 6,951,561 | B2 | 10/2005 | Warren et al. |
| 6,952,129 | B2 | 10/2005 | Lin et al. |
| 6,953,477 | B2 | 10/2005 | Berry |
| 6,955,691 | B2 | 10/2005 | Chae et al. |
| 6,962,606 | B2 | 11/2005 | Michelson |
| 6,964,674 | B1 | 11/2005 | Matsuura et al. |
| 6,964,686 | B2 | 11/2005 | Gordon |
| 6,966,910 | B2 | 11/2005 | Ritland |
| 6,966,912 | B2 | 11/2005 | Michelson |
| 6,969,404 | B2 | 11/2005 | Ferree |
| 6,969,405 | B2 | 11/2005 | Suddaby |
| D512,506 | S | 12/2005 | Layne et al. |
| 6,972,035 | B2 | 12/2005 | Michelson |
| 6,974,479 | B2 | 12/2005 | Trieu |
| 6,979,341 | B2 | 12/2005 | Scribner et al. |
| 6,979,352 | B2 | 12/2005 | Reynolds |
| 6,979,353 | B2 | 12/2005 | Bresina |
| 6,981,981 | B2 | 1/2006 | Reiley et al. |
| 6,997,929 | B2 | 2/2006 | Manzi et al. |
| 7,004,945 | B2 | 2/2006 | Boyd et al. |
| 7,004,971 | B2 | 2/2006 | Serhan et al. |
| 7,008,431 | B2 | 3/2006 | Simonson |
| 7,008,453 | B1 | 3/2006 | Michelson |
| 7,014,633 | B2 | 3/2006 | Cragg |
| 7,018,089 | B2 | 3/2006 | Wenz et al. |
| 7,018,412 | B2 | 3/2006 | Ferreira et al. |
| 7,018,415 | B1 | 3/2006 | McKay |
| 7,018,416 | B2 | 3/2006 | Hanson et al. |
| 7,018,453 | B2 | 3/2006 | Klein et al. |
| 7,022,138 | B2 | 4/2006 | Mashburn |
| 7,025,746 | B2 | 4/2006 | Tal |
| 7,025,787 | B2 | 4/2006 | Bryan et al. |
| 7,029,473 | B2 | 4/2006 | Zucherman et al. |
| 7,029,498 | B2 | 4/2006 | Boehm et al. |
| 7,037,339 | B2 | 5/2006 | Houfburg et al. |
| 7,041,107 | B2 | 5/2006 | Pohjonen et al. |
| 7,044,954 | B2 | 5/2006 | Reiley et al. |
| 7,048,694 | B2 | 5/2006 | Mark et al. |
| 7,048,736 | B2 | 5/2006 | Robinson et al. |
| 7,060,068 | B2 | 6/2006 | Tromanhauser et al. |
| 7,060,073 | B2 | 6/2006 | Frey et al. |
| 7,063,701 | B2 | 6/2006 | Michelson |
| 7,063,702 | B2 | 6/2006 | Michelson |
| 7,063,703 | B2 | 6/2006 | Reo |

(56) References Cited

U.S. PATENT DOCUMENTS

| | | | |
|---|---|---|---|
| 7,063,725 | B2 | 6/2006 | Foley |
| 7,066,960 | B1 | 6/2006 | Dickman |
| 7,066,961 | B2 | 6/2006 | Michelson |
| 7,069,087 | B2 | 6/2006 | Sharkey et al. |
| 7,070,598 | B2 | 7/2006 | Lim et al. |
| 7,070,601 | B2 | 7/2006 | Culbert et al. |
| 7,074,203 | B1 | 7/2006 | Johanson et al. |
| 7,074,226 | B2 | 7/2006 | Roehm et al. |
| 7,081,120 | B2 | 7/2006 | Li et al. |
| 7,081,122 | B1 | 7/2006 | Reiley et al. |
| 7,083,650 | B2 | 8/2006 | Moskowitz et al. |
| 7,087,053 | B2 | 8/2006 | Vanney |
| 7,087,055 | B2 | 8/2006 | Lim et al. |
| 7,087,083 | B2 | 8/2006 | Pasquet et al. |
| 7,089,063 | B2 | 8/2006 | Lesh et al. |
| 7,094,239 | B1 | 8/2006 | Michelson |
| 7,094,257 | B2 | 8/2006 | Mujwid et al. |
| 7,094,258 | B2 | 8/2006 | Lambrecht et al. |
| 7,101,375 | B2 | 9/2006 | Zucherman et al. |
| 7,114,501 | B2 | 10/2006 | Johnson et al. |
| 7,115,128 | B2 | 10/2006 | Michelson |
| 7,115,163 | B2 | 10/2006 | Zimmermann |
| 7,118,572 | B2 | 10/2006 | Bramlet et al. |
| 7,118,579 | B2 | 10/2006 | Michelson |
| 7,118,580 | B1 | 10/2006 | Beyersdorff et al. |
| 7,118,598 | B2 | 10/2006 | Michelson |
| 7,124,761 | B2 | 10/2006 | Lambrecht et al. |
| 7,125,424 | B2 | 10/2006 | Banick et al. |
| 7,128,760 | B2 | 10/2006 | Michelson |
| 7,135,424 | B2 | 11/2006 | Worley et al. |
| 7,153,304 | B2 | 12/2006 | Robie et al. |
| 7,153,305 | B2 | 12/2006 | Johnson et al. |
| 7,153,306 | B2 | 12/2006 | Ralph et al. |
| 7,153,307 | B2 | 12/2006 | Scribner et al. |
| D536,096 | S | 1/2007 | Hoogland et al. |
| 7,156,874 | B2 | 1/2007 | Paponneau et al. |
| 7,156,875 | B2 | 1/2007 | Michelson |
| 7,156,876 | B2 | 1/2007 | Moumene et al. |
| 7,156,877 | B2 | 1/2007 | Lotz et al. |
| 7,163,558 | B2 | 1/2007 | Senegas et al. |
| 7,166,107 | B2 | 1/2007 | Anderson |
| 7,172,612 | B2 | 2/2007 | Ishikawa |
| 7,179,293 | B2 | 2/2007 | McKay |
| 7,179,294 | B2 | 2/2007 | Eisermann et al. |
| 7,189,242 | B2 | 3/2007 | Boyd et al. |
| 7,201,751 | B2 | 4/2007 | Zucherman et al. |
| 7,204,851 | B2 | 4/2007 | Trieu et al. |
| 7,207,991 | B2 | 4/2007 | Michelson |
| 7,211,112 | B2 | 5/2007 | Baynham et al. |
| 7,214,227 | B2 | 5/2007 | Colleran et al. |
| 7,217,291 | B2 | 5/2007 | Zucherman et al. |
| 7,217,293 | B2 | 5/2007 | Branch |
| 7,220,280 | B2 | 5/2007 | Kast et al. |
| 7,220,281 | B2 | 5/2007 | Lambrecht et al. |
| 7,223,227 | B2 | 5/2007 | Pflueger |
| 7,223,292 | B2 | 5/2007 | Messerli et al. |
| 7,226,481 | B2 | 6/2007 | Kuslich |
| 7,226,482 | B2 | 6/2007 | Messerli et al. |
| 7,226,483 | B2 | 6/2007 | Gerber et al. |
| 7,235,101 | B2 | 6/2007 | Berry et al. |
| 7,238,204 | B2 | 7/2007 | Le et al. |
| 7,241,297 | B2 | 7/2007 | Shaolian et al. |
| 7,244,273 | B2 | 7/2007 | Pedersen et al. |
| 7,250,060 | B2 | 7/2007 | Trieu |
| 7,252,671 | B2 | 8/2007 | Scribner et al. |
| 7,267,683 | B2 | 9/2007 | Sharkey et al. |
| 7,267,687 | B2 | 9/2007 | McGuckin, Jr. |
| 7,270,679 | B2 | 9/2007 | Istephanous et al. |
| 7,276,062 | B2 | 10/2007 | McDaniel et al. |
| 7,282,061 | B2 | 10/2007 | Sharkey et al. |
| 7,291,173 | B2 | 11/2007 | Richelsoph et al. |
| 7,300,440 | B2 | 11/2007 | Zdeblick |
| 7,306,628 | B2 | 12/2007 | Zucherman et al. |
| 7,309,357 | B2 | 12/2007 | Kim |
| 7,311,713 | B2 | 12/2007 | Johnson et al. |
| 7,316,714 | B2 | 1/2008 | Gordon et al. |
| 7,318,840 | B2 | 1/2008 | McKay |
| 7,320,689 | B2 | 1/2008 | Keller |
| 7,320,708 | B1 | 1/2008 | Bernstein |
| 7,322,962 | B2 | 1/2008 | Forrest |
| 7,326,211 | B2 | 2/2008 | Padget et al. |
| 7,326,248 | B2 | 2/2008 | Michelson |
| 7,335,203 | B2 | 2/2008 | Winslow et al. |
| 7,351,262 | B2 | 4/2008 | Bindseil et al. |
| 7,361,140 | B2 | 4/2008 | Ries et al. |
| 7,371,238 | B2 | 5/2008 | Soboleski et al. |
| 7,377,942 | B2 | 5/2008 | Berry |
| 7,383,639 | B2 | 6/2008 | Malandain |
| 7,400,930 | B2 | 7/2008 | Sharkey et al. |
| 7,410,501 | B2 | 8/2008 | Michelson |
| 7,413,576 | B2 | 8/2008 | Sybert et al. |
| 7,422,594 | B2 | 9/2008 | Zander |
| 7,434,325 | B2 | 10/2008 | Foley et al. |
| 7,442,211 | B2 | 10/2008 | De et al. |
| 7,445,636 | B2 | 11/2008 | Michelson |
| 7,445,637 | B2 | 11/2008 | Taylor |
| 7,470,273 | B2 | 12/2008 | Dougherty-Shah |
| D584,812 | S | 1/2009 | Ries |
| 7,473,256 | B2 | 1/2009 | Assell et al. |
| 7,473,268 | B2 | 1/2009 | Zucherman et al. |
| 7,476,251 | B2 | 1/2009 | Zucherman et al. |
| 7,485,134 | B2 | 2/2009 | Simonson |
| 7,488,326 | B2 | 2/2009 | Elliott |
| 7,491,237 | B2 | 2/2009 | Randall et al. |
| 7,500,991 | B2 | 3/2009 | Bartish et al. |
| 7,503,920 | B2 | 3/2009 | Siegal |
| 7,503,933 | B2 | 3/2009 | Michelson |
| 7,507,241 | B2 | 3/2009 | Levy et al. |
| 7,517,363 | B2 | 4/2009 | Rogers |
| 7,520,888 | B2 | 4/2009 | Trieu |
| 7,547,317 | B2 | 6/2009 | Cragg |
| 7,556,629 | B2 | 7/2009 | Von et al. |
| 7,556,651 | B2 | 7/2009 | Humphreys et al. |
| 7,569,054 | B2 | 8/2009 | Michelson |
| 7,569,074 | B2 | 8/2009 | Eisermann et al. |
| 7,572,279 | B2 | 8/2009 | Jackson |
| 7,575,580 | B2 | 8/2009 | Lim et al. |
| 7,575,599 | B2 | 8/2009 | Villiers et al. |
| 7,578,820 | B2 | 8/2009 | Moore et al. |
| 7,588,574 | B2 | 9/2009 | Assell et al. |
| 7,601,173 | B2 | 10/2009 | Messerli et al. |
| 7,608,083 | B2 | 10/2009 | Lee et al. |
| 7,618,458 | B2 | 11/2009 | Biedermann et al. |
| 7,621,950 | B1 | 11/2009 | Globerman et al. |
| 7,621,960 | B2 | 11/2009 | Boyd et al. |
| 7,625,377 | B2 | 12/2009 | Veldhuizen et al. |
| 7,625,378 | B2 | 12/2009 | Foley |
| 7,625,394 | B2 | 12/2009 | Molz et al. |
| 7,637,905 | B2 | 12/2009 | Saadat et al. |
| 7,641,657 | B2 | 1/2010 | Cragg |
| 7,641,670 | B2 | 1/2010 | Davison et al. |
| 7,641,692 | B2 | 1/2010 | Bryan et al. |
| 7,647,123 | B2 | 1/2010 | Sharkey et al. |
| 7,648,523 | B2 | 1/2010 | Mirkovic et al. |
| 7,655,010 | B2 | 2/2010 | Serhan et al. |
| 7,666,186 | B2 | 2/2010 | Harp |
| 7,666,266 | B2 | 2/2010 | Izawa et al. |
| 7,670,354 | B2 | 3/2010 | Davison et al. |
| 7,670,374 | B2 | 3/2010 | Schaller |
| 7,674,265 | B2 | 3/2010 | Smith et al. |
| 7,674,273 | B2 | 3/2010 | Davison et al. |
| 7,682,370 | B2 | 3/2010 | Pagliuca et al. |
| 7,682,400 | B2 | 3/2010 | Zwirkoski |
| 7,691,120 | B2 | 4/2010 | Shluzas et al. |
| 7,691,147 | B2 | 4/2010 | Gutlin et al. |
| 7,699,878 | B2 | 4/2010 | Pavlov et al. |
| 7,703,727 | B2 | 4/2010 | Selness |
| 7,704,280 | B2 | 4/2010 | Lechmann et al. |
| 7,717,944 | B2 | 5/2010 | Foley et al. |
| 7,722,530 | B2 | 5/2010 | Davison |
| 7,722,612 | B2 | 5/2010 | Sala et al. |
| 7,722,674 | B1 | 5/2010 | Grotz |
| 7,727,263 | B2 | 6/2010 | Cragg |
| 7,731,751 | B2 | 6/2010 | Butler et al. |

(56) References Cited

U.S. PATENT DOCUMENTS 7,740,633 B2 6/2010 Assell et al.
7,744,599 B2 6/2010 Cragg
7,744,650 B2 6/2010 Lindner et al.
7,749,270 B2 7/2010 Peterman
7,762,995 B2 7/2010 Eversull et al.
7,763,025 B2 7/2010 Ainsworth
7,763,028 B2 7/2010 Lim et al.
7,763,038 B2 7/2010 O'Brien
7,763,055 B2 7/2010 Foley
7,766,930 B2 8/2010 DiPoto et al.
7,771,473 B2 8/2010 Thramann
7,771,479 B2 8/2010 Humphreys et al.
7,785,368 B2 8/2010 Schaller
7,789,914 B2 9/2010 Michelson
7,794,463 B2 9/2010 Cragg
7,799,032 B2 9/2010 Assell et al.
7,799,033 B2 9/2010 Assell et al.
7,799,036 B2 9/2010 Davison et al.
7,799,080 B2 9/2010 Doty
7,799,081 B2 9/2010 McKinley
7,799,083 B2 9/2010 Smith et al.
7,803,161 B2 9/2010 Foley et al.
D626,233 S 10/2010 Cipoletti et al.
7,814,429 B2 10/2010 Buffet et al.
7,819,921 B2 10/2010 Grotz
7,824,410 B2 11/2010 Simonson et al.
7,824,429 B2 11/2010 Culbert et al.
7,824,445 B2 11/2010 Biro et al.
7,828,807 B2 11/2010 LeHuec et al.
7,837,734 B2 11/2010 Zucherman et al.
7,846,183 B2 12/2010 Blain
7,846,206 B2 12/2010 Oglaza et al.
7,850,695 B2 12/2010 Pagliuca et al.
7,850,733 B2 12/2010 Baynham et al.
7,854,766 B2 12/2010 Moskowitz et al.
7,857,832 B2 12/2010 Culbert et al.
7,857,840 B2 12/2010 Krebs
7,862,590 B2 1/2011 Lim et al.
7,862,595 B2 1/2011 Foley et al.
7,867,259 B2 1/2011 Foley et al.
7,874,980 B2 1/2011 Sonnenschein et al.
7,875,077 B2 1/2011 Humphreys et al.
7,879,098 B1 2/2011 Simmons
7,887,589 B2 2/2011 Glenn et al.
7,892,171 B2 2/2011 Davison et al.
7,892,249 B2 2/2011 Davison et al.
7,901,438 B2 3/2011 Culbert et al.
7,901,459 B2 3/2011 Hodges et al.
7,909,870 B2 3/2011 Kraus
7,909,874 B2 3/2011 Zielinski
7,918,874 B2 4/2011 Siegal
7,922,719 B2 4/2011 Ralph et al.
7,922,729 B2 4/2011 Michelson
7,927,373 B2 4/2011 Parsons et al.
7,931,674 B2 4/2011 Zucherman et al.
7,931,689 B2 4/2011 Hochschuler et al.
7,935,051 B2 5/2011 Miles et al.
7,938,832 B2 5/2011 Culbert et al.
7,942,903 B2 5/2011 Moskowitz et al.
7,947,078 B2 5/2011 Siegal
7,951,199 B2 5/2011 Miller
7,955,391 B2 6/2011 Schaller
7,959,675 B2 6/2011 Gately
7,963,967 B1 6/2011 Woods
7,963,993 B2 6/2011 Schaller
7,967,864 B2 6/2011 Schaller
7,967,865 B2 6/2011 Schaller
7,985,231 B2 7/2011 Sankaran
7,993,403 B2 8/2011 Foley et al.
7,998,176 B2 8/2011 Culbert
8,007,535 B2 8/2011 Hudgins et al.
8,012,212 B2 9/2011 Link et al.
8,021,424 B2 9/2011 Beger et al.
8,021,426 B2 9/2011 Segal et al.
8,025,697 B2 9/2011 McClellan et al.
8,034,109 B2 10/2011 Zwirkoski
8,034,110 B2 10/2011 Garner et al.
8,038,703 B2 10/2011 Dobak et al.
8,043,293 B2 10/2011 Warnick
8,043,381 B2 10/2011 Hestad et al.
8,052,754 B2 11/2011 Froehlich
8,057,544 B2 11/2011 Schaller
8,057,545 B2 11/2011 Hughes et al.
8,062,375 B2 11/2011 Glerum et al.
8,070,815 B2 12/2011 Yu et al.
8,075,621 B2 12/2011 Michelson
8,097,036 B2 1/2012 Cordaro et al.
8,100,978 B2 1/2012 Bass
8,105,382 B2 1/2012 Olmos et al. ..... A61F 2/46 623/17.15
8,109,972 B2 2/2012 Zucherman et al.
8,109,977 B2 2/2012 Culbert et al.
8,114,088 B2 2/2012 Miller
8,118,871 B2 2/2012 Gordon
8,128,700 B2 3/2012 Delurio et al.
8,128,702 B2 3/2012 Zucherman et al.
8,133,232 B2 3/2012 Levy et al.
8,147,549 B2 4/2012 Metcalf et al.
8,177,812 B2 5/2012 Sankaran
8,187,327 B2 5/2012 Edidin et al.
8,192,495 B2 6/2012 Simpson et al.
8,202,322 B2 6/2012 Doty
8,206,423 B2 6/2012 Siegal
8,216,312 B2 7/2012 Gray
8,216,314 B2 7/2012 Richelsoph
8,216,317 B2 7/2012 Thibodeau
8,221,501 B2 7/2012 Eisermann et al.
8,221,502 B2 7/2012 Branch
8,221,503 B2 7/2012 Garcia et al.
8,231,675 B2 7/2012 Rhoda
8,231,681 B2 7/2012 Castleman et al.
8,236,029 B2 8/2012 Siegal
8,236,058 B2 8/2012 Fabian et al.
8,241,328 B2 8/2012 Siegal
8,241,358 B2 8/2012 Butler et al.
8,241,361 B2 8/2012 Link
8,241,364 B2 8/2012 Hansell et al.
8,246,622 B2 8/2012 Siegal et al.
8,257,440 B2 9/2012 Gordon et al.
8,257,442 B2 9/2012 Edie et al.
8,262,666 B2 9/2012 Baynham et al.
8,262,736 B2 9/2012 Michelson
8,267,939 B2 9/2012 Cipoletti et al.
8,267,965 B2 9/2012 Gimbel et al.
8,273,128 B2 9/2012 Oh et al.
8,273,129 B2 9/2012 Baynham et al.
8,287,599 B2 10/2012 McGuckin
8,292,959 B2 10/2012 Webb et al.
8,303,663 B2 11/2012 Jimenez et al.
8,313,528 B1 11/2012 Wensel
8,317,866 B2 11/2012 Palmatier et al.
8,323,345 B2 12/2012 Sledge
8,328,812 B2 12/2012 Siegal et al.
8,328,852 B2 12/2012 Zehavi et al.
8,337,559 B2 12/2012 Hansell et al.
8,343,193 B2 1/2013 Johnson et al.
8,343,222 B2 1/2013 Cope
8,353,961 B2 1/2013 McClintock et al.
8,361,154 B2 1/2013 Reo
8,366,777 B2 2/2013 Matthis et al.
8,377,098 B2 2/2013 Andry et al.
8,377,133 B2 2/2013 Yuan et al.
8,382,842 B2 2/2013 Greenhalgh et al.
8,394,129 B2 3/2013 Morgenstern et al.
8,398,712 B2 3/2013 De et al.
8,398,713 B2 3/2013 Weiman
8,403,990 B2 3/2013 Dryer et al.
8,409,282 B2 4/2013 Kim
8,409,290 B2 4/2013 Zamani et al.
8,409,291 B2 4/2013 Blackwell et al.
8,414,650 B2 4/2013 Bertele et al.
8,425,559 B2 4/2013 Tebbe et al.
8,435,298 B2 5/2013 Weiman
8,454,617 B2 6/2013 Schaller

(56) References Cited

U.S. PATENT DOCUMENTS 8,454,698 B2 6/2013 De et al.
8,465,524 B2 6/2013 Siegal
8,470,043 B2 6/2013 Schaller et al.
8,480,715 B2 7/2013 Gray
8,480,742 B2 7/2013 Pisharodi
8,480,748 B2 7/2013 Poulos
8,486,109 B2 7/2013 Siegal
8,486,148 B2 7/2013 Butler et al.
8,491,591 B2 7/2013 Fuerderer
8,491,653 B2 7/2013 Zucherman et al.
8,491,657 B2 7/2013 Attia et al.
8,491,659 B2 7/2013 Weiman
8,506,635 B2 8/2013 Palmatier et al.
8,518,087 B2 8/2013 Lopez et al.
8,518,120 B2 8/2013 Glerum et al.
8,523,909 B2 9/2013 Hess
8,523,944 B2 9/2013 Jimenez et al.
8,535,380 B2 9/2013 Greenhalgh et al.
8,545,567 B1 10/2013 Krueger
8,551,092 B2 10/2013 Morgan et al.
8,551,173 B2 10/2013 Lechmann et al.
8,556,978 B2 10/2013 Schaller
8,556,979 B2 10/2013 Glerum et al.
8,568,481 B2 10/2013 Olmos et al. ..... A61F 2/30771 623/17.15
8,579,977 B2 11/2013 Fabian
8,579,981 B2 11/2013 Lim
8,591,583 B2 11/2013 Schaller et al.
8,591,585 B2 11/2013 McLaughlin et al.
8,597,330 B2 12/2013 Siegal
8,597,333 B2 12/2013 Morgenstern et al.
8,597,360 B2 12/2013 McLuen et al.
8,603,168 B2 12/2013 Gordon et al.
8,603,170 B2 12/2013 Cipoletti et al.
8,603,177 B2 12/2013 Gray
8,623,088 B1 1/2014 Tohmeh et al.
8,623,091 B2 1/2014 Suedkamp et al.
8,628,576 B2 1/2014 Triplett et al.
8,628,577 B1 1/2014 Jimenez
8,628,578 B2 1/2014 Miller et al.
8,632,595 B2 1/2014 Weiman
8,636,746 B2 1/2014 Jimenez et al.
8,641,764 B2 2/2014 Gately
8,663,329 B2 3/2014 Ernst
8,663,331 B2 3/2014 McClellan et al.
8,668,740 B2 3/2014 Rhoda et al.
8,672,977 B2 3/2014 Siegal et al.
8,679,161 B2 3/2014 Malandain et al.
8,679,183 B2 3/2014 Glerum et al.
8,685,095 B2 4/2014 Miller et al.
8,685,098 B2 4/2014 Glerum et al.
8,696,751 B2 4/2014 Ashley et al.
8,702,757 B2 4/2014 Thommen et al.
8,702,798 B2 4/2014 Matthis et al.
8,709,086 B2 4/2014 Glerum et al.
8,709,088 B2 4/2014 Kleiner et al.
8,715,351 B1 5/2014 Pinto
8,721,723 B2 5/2014 Hansell et al.
8,728,160 B2 5/2014 Globerman et al.
8,728,166 B2 5/2014 Schwab
8,740,954 B2 6/2014 Ghobrial et al.
8,753,398 B2 6/2014 Gordon et al.
8,758,349 B2 6/2014 Germain et al.
8,758,441 B2 6/2014 Hovda et al.
8,764,806 B2 7/2014 Abdou
8,771,360 B2 7/2014 Jimenez et al.
8,777,993 B2 7/2014 Siegal et al.
8,778,025 B2 7/2014 Ragab et al.
8,795,366 B2 8/2014 Varela
8,795,374 B2 8/2014 Chee
8,801,787 B2 8/2014 Schaller
8,801,792 B2 8/2014 De et al.
8,808,376 B2 8/2014 Schaller
8,828,085 B1 9/2014 Jensen
8,845,638 B2 9/2014 Siegal et al.
8,845,728 B1 9/2014 Abdou
8,845,731 B2 9/2014 Weiman
8,845,732 B2 9/2014 Weiman
8,845,733 B2 9/2014 O'Neil et al.
8,845,734 B2 9/2014 Weiman
8,852,242 B2 10/2014 Morgenstern et al.
8,852,243 B2 10/2014 Morgenstern et al.
8,852,279 B2 10/2014 Weiman
8,864,833 B2 10/2014 Glerum et al.
8,888,853 B2 11/2014 Glerum et al.
8,888,854 B2 11/2014 Glerum et al.
8,894,711 B2 11/2014 Varela
8,900,235 B2 12/2014 Siegal
8,900,307 B2 12/2014 Hawkins et al.
8,906,098 B2 12/2014 Siegal
8,920,506 B2 12/2014 McGuckin, Jr.
8,926,704 B2 1/2015 Glerum
8,936,641 B2 1/2015 Cain
8,940,050 B2 1/2015 Laurence et al.
8,940,052 B2 1/2015 Lechmann et al.
8,961,609 B2 2/2015 Schaller
8,968,408 B2 3/2015 Schaller et al.
8,979,860 B2 3/2015 Voellmicke et al.
8,979,929 B2 3/2015 Schaller
8,986,387 B1 3/2015 To et al.
8,986,388 B2 3/2015 Siegal et al.
8,986,389 B2 3/2015 Lim et al.
9,005,291 B2 4/2015 Loebl et al.
9,017,408 B2 4/2015 Siegal et al.
9,017,413 B2 4/2015 Siegal et al.
9,039,767 B2 5/2015 Raymond et al.
9,039,771 B2 5/2015 Glerum et al.
9,044,334 B2 6/2015 Siegal et al.
9,044,338 B2 6/2015 Schaller
9,060,876 B1 6/2015 To et al.
9,066,808 B2 6/2015 Schaller
9,078,767 B1 7/2015 McLean
9,089,428 B2 7/2015 Bertele et al.
9,095,446 B2 8/2015 Landry et al.
9,095,447 B2 8/2015 Barreiro et al.
9,101,488 B2 8/2015 Malandain
9,101,489 B2 8/2015 Protopsaltis et al.
9,101,491 B2 8/2015 Rodgers et al.
9,101,492 B2 8/2015 Mangione et al.
9,107,766 B1 8/2015 Mclean et al.
9,155,631 B2 10/2015 Seifert et al.
9,237,956 B1 1/2016 Jensen
9,254,138 B2 2/2016 Siegal et al.
9,259,326 B2 2/2016 Schaller
9,271,846 B2 3/2016 Lim et al.
9,277,928 B2 3/2016 Morgenstern Lopez
9,282,979 B2 3/2016 O'Neil et al.
9,283,092 B2 3/2016 Siegal et al.
9,295,562 B2 3/2016 Lechmann et al.
9,314,348 B2 4/2016 Emstad
9,320,610 B2 4/2016 Alheidt et al.
9,320,615 B2 4/2016 Suedkamp et al.
9,326,866 B2 5/2016 Schaller et al.
9,333,091 B2 5/2016 DiMauro
9,387,087 B2 7/2016 Tyber
9,402,732 B2 8/2016 Gabelberger
9,402,739 B2 8/2016 Weiman et al.
9,408,712 B2 8/2016 Siegal et al.
9,414,923 B2 8/2016 Studer et al.
9,414,934 B2 8/2016 Cain
9,414,936 B2 8/2016 Miller et al.
9,433,510 B2 9/2016 Lechmann et al.
9,439,776 B2 9/2016 DiMauro et al.
9,439,777 B2 9/2016 DiMauro
9,445,825 B2 9/2016 Belaney et al.
9,463,099 B2 10/2016 Levy et al.
9,474,623 B2 10/2016 Cain
9,492,288 B2 * 11/2016 Wagner ..... A61F 2/4611
9,510,954 B2 12/2016 Glerum et al.
9,522,070 B2 12/2016 Flower et al.
9,532,884 B2 1/2017 Siegal et al.
9,566,165 B2 2/2017 Lee et al.
9,566,167 B2 2/2017 Barrus et al.
9,579,215 B2 2/2017 Suedkamp et al.

(56) References Cited

U.S. PATENT DOCUMENTS 9,592,129 B2 3/2017 Slivka et al.
9,597,197 B2 3/2017 Lechmann et al.
9,662,223 B2 5/2017 Matthis et al.
9,662,224 B2 5/2017 Weiman et al.
9,675,470 B2 6/2017 Packer et al.
9,724,207 B2 8/2017 DiMauro et al.
9,730,803 B2 8/2017 DiMauro et al.
9,750,552 B2 9/2017 Stephan et al.
9,750,618 B1 9/2017 Daffinson et al.
9,788,962 B2 10/2017 Gabelberger
9,788,963 B2 10/2017 Aquino et al.
9,788,971 B1 10/2017 Stein
9,801,639 B2 10/2017 O'Neil et al.
9,801,640 B2 10/2017 O'Neil et al.
9,801,729 B2 10/2017 DiMauro et al.
9,801,734 B1 10/2017 Stein et al.
9,808,351 B2 11/2017 Kelly et al.
9,808,353 B2 11/2017 Suddaby et al.
9,814,589 B2 11/2017 DiMauro
9,814,590 B2 11/2017 Serhan et al.
9,833,334 B2 12/2017 Voellmicke et al.
9,839,528 B2 12/2017 Weiman et al.
9,839,530 B2 12/2017 Hawkins et al.
9,848,991 B2 12/2017 Boehm et al.
9,872,779 B2 1/2018 Miller et al.
9,895,236 B2 2/2018 Voellmicke et al.
9,907,670 B2 3/2018 Deridder et al.
9,918,851 B2 3/2018 Willis et al.
9,924,978 B2 3/2018 Thommen et al.
9,925,060 B2 3/2018 DiMauro et al.
9,931,223 B2 4/2018 Cain
9,931,226 B2 4/2018 Kurtaliaj et al.
9,937,053 B2 4/2018 Melkent et al.
9,949,769 B2 4/2018 Serhan et al.
9,962,272 B1 5/2018 Daffinson et al.
9,974,664 B2 5/2018 Emerick et al.
9,980,823 B2 5/2018 Matthis et al.
9,987,142 B2 6/2018 McConnell
9,993,350 B2 6/2018 Cain
10,004,607 B2 6/2018 Weiman et al.
10,034,772 B2 7/2018 Glerum et al.
10,058,433 B2 8/2018 Lechmann et al.
10,085,843 B2 10/2018 DiMauro
10,092,417 B2 10/2018 Weiman et al.
10,098,759 B2 10/2018 Weiman
10,137,009 B2 11/2018 Weiman et al.
10,143,569 B2 12/2018 Weiman et al.
10,166,117 B1 1/2019 Daffinson et al.
10,182,831 B2 1/2019 Marnay et al.
10,219,915 B1 3/2019 Stein
10,238,500 B2 3/2019 Rogers et al.
10,265,191 B2 4/2019 Lim et al.
10,307,254 B2 6/2019 Levy et al.
10,363,142 B2 7/2019 McClintock et al.
10,376,372 B2 8/2019 Serhan et al.
10,398,566 B2 9/2019 Olmos et al.
10,405,986 B2 9/2019 Kelly et al.
10,405,989 B2 9/2019 O'Neil et al.
10,420,651 B2 9/2019 Serhan et al.
10,426,632 B2 10/2019 Butler et al.
10,433,971 B2 10/2019 DiMauro et al.
10,433,974 B2 10/2019 O'Neil
10,433,977 B2 10/2019 Lechmann et al.
10,449,056 B2 10/2019 Cain
10,449,058 B2 10/2019 Lechmann et al.
10,470,894 B2 11/2019 Foley et al.
10,492,918 B2 12/2019 DiMauro
10,492,924 B2 12/2019 Stein et al.
10,512,489 B2 12/2019 Serhan et al.
10,537,436 B2 1/2020 Maguire et al.
10,548,741 B2 2/2020 Suedkamp et al.
10,555,817 B2 2/2020 DiMauro et al.
10,575,959 B2 3/2020 DiMauro et al.
10,583,013 B2 3/2020 DiMauro et al.
10,583,015 B2 * 3/2020 Olmos ..... A61F 2/4455
10,624,758 B2 4/2020 Slivka et al.
10,639,164 B2 5/2020 DiMauro et al.
10,639,166 B2 5/2020 Weiman et al.
10,682,241 B2 6/2020 Glerum et al.
10,743,914 B2 8/2020 Lopez et al.
10,842,644 B2 11/2020 Weiman et al.
10,966,840 B2 4/2021 Voellmicke et al.
10,973,652 B2 4/2021 Hawkins et al.
11,051,954 B2 7/2021 Greenhalgh et al.
11,103,362 B2 8/2021 Butler et al.
11,426,290 B2 * 8/2022 Miller ..... A61F 2/447
2001/0011174 A1 8/2001 Reiley et al.
2001/0012950 A1 8/2001 Nishtala et al.
2001/0016741 A1 8/2001 Burkus et al.
2001/0016775 A1 8/2001 Scarborough et al.
2001/0027320 A1 10/2001 Sasso
2001/0032020 A1 10/2001 Besselink
2001/0037126 A1 11/2001 Stack et al.
2001/0039452 A1 11/2001 Zucherman et al.
2001/0039453 A1 11/2001 Gresser et al.
2001/0049529 A1 12/2001 Cachia et al.
2001/0049530 A1 12/2001 Culbert et al.
2001/0049531 A1 12/2001 Reiley et al.
2001/0056302 A1 12/2001 Boyer et al.
2002/0001476 A1 1/2002 Nagamine et al.
2002/0010070 A1 1/2002 Cales et al.
2002/0016583 A1 2/2002 Cragg
2002/0026195 A1 2/2002 Layne et al.
2002/0026244 A1 2/2002 Trieu
2002/0029084 A1 3/2002 Paul et al.
2002/0032462 A1 3/2002 Houser et al.
2002/0032483 A1 3/2002 Nicholson et al.
2002/0035400 A1 3/2002 Bryan et al.
2002/0037799 A1 3/2002 Li et al.
2002/0045904 A1 4/2002 Fuss et al.
2002/0045942 A1 4/2002 Ham
2002/0055740 A1 5/2002 Lieberman
2002/0055781 A1 5/2002 Sazy
2002/0058947 A1 5/2002 Hochschuler et al.
2002/0068974 A1 6/2002 Kuslich et al.
2002/0068976 A1 6/2002 Jackson
2002/0068977 A1 6/2002 Jackson
2002/0072801 A1 6/2002 Michelson
2002/0077700 A1 6/2002 Varga et al.
2002/0077701 A1 6/2002 Kuslich
2002/0082584 A1 6/2002 Rosenman et al.
2002/0082608 A1 6/2002 Reiley et al.
2002/0087152 A1 7/2002 Mikus et al.
2002/0087163 A1 7/2002 Dixon et al.
2002/0091387 A1 7/2002 Hoogland
2002/0091390 A1 7/2002 Michelson
2002/0099385 A1 7/2002 Ralph et al.
2002/0107519 A1 8/2002 Dixon et al.
2002/0107573 A1 8/2002 Steinberg
2002/0120335 A1 8/2002 Angelucci et al.
2002/0128713 A1 9/2002 Ferree
2002/0128715 A1 9/2002 Bryan et al.
2002/0128716 A1 9/2002 Cohen et al.
2002/0138078 A1 9/2002 Chappuis
2002/0138146 A1 9/2002 Jackson
2002/0143331 A1 10/2002 Zucherman et al.
2002/0143334 A1 10/2002 Hoffmann et al.
2002/0143335 A1 10/2002 Von et al.
2002/0151895 A1 10/2002 Soboleski et al.
2002/0151976 A1 10/2002 Foley et al.
2002/0156482 A1 10/2002 Scribner et al.
2002/0161444 A1 10/2002 Choi
2002/0165612 A1 11/2002 Gerber et al.
2002/0169471 A1 11/2002 Ferdinand
2002/0172851 A1 11/2002 Corey et al.
2002/0173796 A1 11/2002 Cragg
2002/0173841 A1 11/2002 Ortiz et al.
2002/0173851 A1 11/2002 McKay
2002/0183761 A1 12/2002 Johnson et al.
2002/0183778 A1 12/2002 Reiley et al.
2002/0183848 A1 12/2002 Ray et al.
2002/0191487 A1 12/2002 Sand
2002/0193883 A1 12/2002 Wironen
2002/0198526 A1 12/2002 Shaolian et al.

(56) References Cited

U.S. PATENT DOCUMENTS

| | | | |
|---|---|---|---|
| 2003/0004575 | A1 | 1/2003 | Erickson |
| 2003/0004576 | A1 | 1/2003 | Thalgott |
| 2003/0006942 | A1 | 1/2003 | Searls et al. |
| 2003/0014112 | A1 | 1/2003 | Ralph et al. |
| 2003/0014113 | A1 | 1/2003 | Ralph et al. |
| 2003/0014116 | A1 | 1/2003 | Ralph et al. |
| 2003/0018390 | A1 | 1/2003 | Husson |
| 2003/0023305 | A1 | 1/2003 | McKay |
| 2003/0028250 | A1 | 2/2003 | Reiley et al. |
| 2003/0028251 | A1 | 2/2003 | Mathews |
| 2003/0032963 | A1 | 2/2003 | Reiss et al. |
| 2003/0040796 | A1 | 2/2003 | Ferree |
| 2003/0040799 | A1 | 2/2003 | Boyd et al. |
| 2003/0045937 | A1 | 3/2003 | Ginn |
| 2003/0045939 | A1 | 3/2003 | Casutt |
| 2003/0050644 | A1 | 3/2003 | Boucher et al. |
| 2003/0063582 | A1 | 4/2003 | Mizell et al. |
| 2003/0065330 | A1 | 4/2003 | Zucherman et al. |
| 2003/0065396 | A1 | 4/2003 | Michelson |
| 2003/0069582 | A1 | 4/2003 | Culbert |
| 2003/0069593 | A1 | 4/2003 | Tremulis et al. |
| 2003/0069642 | A1 | 4/2003 | Ralph et al. |
| 2003/0073998 | A1 | 4/2003 | Pagliuca et al. |
| 2003/0074063 | A1 | 4/2003 | Gerbec et al. |
| 2003/0074075 | A1 | 4/2003 | Thomas et al. |
| 2003/0078667 | A1 | 4/2003 | Manasas et al. |
| 2003/0083642 | A1 | 5/2003 | Boyd et al. |
| 2003/0083688 | A1 | 5/2003 | Simonson |
| 2003/0108588 | A1 | 6/2003 | Chen et al. |
| 2003/0130664 | A1 | 7/2003 | Boucher et al. |
| 2003/0130739 | A1 | 7/2003 | Gerbec et al. |
| 2003/0135275 | A1 | 7/2003 | Garcia |
| 2003/0139648 | A1 | 7/2003 | Foley et al. |
| 2003/0139812 | A1 | 7/2003 | Garcia |
| 2003/0139813 | A1 | 7/2003 | Messerli et al. |
| 2003/0153874 | A1 | 8/2003 | Tal |
| 2003/0171812 | A1 | 9/2003 | Grunberg et al. |
| 2003/0187431 | A1 | 10/2003 | Simonson |
| 2003/0187445 | A1 | 10/2003 | Keith et al. |
| 2003/0187506 | A1 | 10/2003 | Ross et al. |
| 2003/0191414 | A1 | 10/2003 | Reiley et al. |
| 2003/0191489 | A1 | 10/2003 | Reiley et al. |
| 2003/0191531 | A1 | 10/2003 | Berry et al. |
| 2003/0195518 | A1 | 10/2003 | Cragg |
| 2003/0195547 | A1 | 10/2003 | Scribner et al. |
| 2003/0195630 | A1 | 10/2003 | Ferree |
| 2003/0199979 | A1 | 10/2003 | McGuckin |
| 2003/0204261 | A1 | 10/2003 | Eiserman |
| 2003/0208122 | A1 | 11/2003 | Melkent et al. |
| 2003/0208136 | A1 | 11/2003 | Mark et al. |
| 2003/0208203 | A1 | 11/2003 | Lim et al. |
| 2003/0208220 | A1 | 11/2003 | Worley et al. |
| 2003/0208270 | A9 | 11/2003 | Michelson |
| 2003/0220643 | A1 | 11/2003 | Ferree |
| 2003/0220648 | A1 | 11/2003 | Osorio et al. |
| 2003/0220695 | A1 | 11/2003 | Sevrain |
| 2003/0229350 | A1 | 12/2003 | Kay |
| 2003/0229372 | A1 | 12/2003 | Reiley et al. |
| 2003/0233096 | A1 | 12/2003 | Osorio et al. |
| 2003/0233102 | A1 | 12/2003 | Nakamura et al. |
| 2003/0233145 | A1 | 12/2003 | Landry et al. |
| 2003/0233146 | A1 | 12/2003 | Grinberg et al. |
| 2004/0002761 | A1 | 1/2004 | Rogers et al. |
| 2004/0006391 | A1 | 1/2004 | Reiley |
| 2004/0008949 | A1 | 1/2004 | Liu et al. |
| 2004/0010251 | A1 | 1/2004 | Pitaru et al. |
| 2004/0010260 | A1 | 1/2004 | Scribner et al. |
| 2004/0010263 | A1 | 1/2004 | Boucher et al. |
| 2004/0010318 | A1 | 1/2004 | Ferree |
| 2004/0019354 | A1 | 1/2004 | Johnson et al. |
| 2004/0019359 | A1 | 1/2004 | Worley et al. |
| 2004/0024408 | A1 | 2/2004 | Burkus et al. |
| 2004/0024409 | A1 | 2/2004 | Sand et al. |
| 2004/0024410 | A1 | 2/2004 | Olson et al. |
| 2004/0024463 | A1 | 2/2004 | Thomas et al. |
| 2004/0024465 | A1 | 2/2004 | Lambrecht et al. |
| 2004/0030387 | A1 | 2/2004 | Landry et al. |
| 2004/0034343 | A1 | 2/2004 | Gillespie et al. |
| 2004/0034429 | A1 | 2/2004 | Lambrecht et al. |
| 2004/0049190 | A1 | 3/2004 | Biedermann et al. |
| 2004/0049203 | A1 | 3/2004 | Scribner et al. |
| 2004/0049223 | A1 | 3/2004 | Nishtala et al. |
| 2004/0049270 | A1 | 3/2004 | Gewirtz |
| 2004/0054412 | A1 | 3/2004 | Gerbec et al. |
| 2004/0059333 | A1 | 3/2004 | Carl et al. |
| 2004/0059337 | A1 | 3/2004 | Hanson et al. |
| 2004/0059339 | A1 | 3/2004 | Roehm et al. |
| 2004/0059350 | A1 | 3/2004 | Gordon et al. |
| 2004/0059418 | A1 | 3/2004 | McKay et al. |
| 2004/0064144 | A1 | 4/2004 | Johnson et al. |
| 2004/0068269 | A1 | 4/2004 | Bonati et al. |
| 2004/0073213 | A1 | 4/2004 | Serhan et al. |
| 2004/0073308 | A1 | 4/2004 | Kuslich et al. |
| 2004/0073310 | A1 | 4/2004 | Moumene et al. |
| 2004/0082953 | A1 | 4/2004 | Petit |
| 2004/0083000 | A1 | 4/2004 | Keller et al. |
| 2004/0087947 | A1 | 5/2004 | Lim et al. |
| 2004/0088055 | A1 | 5/2004 | Hanson et al. |
| 2004/0092933 | A1 | 5/2004 | Shaolian et al. |
| 2004/0092948 | A1 | 5/2004 | Stevens et al. |
| 2004/0092988 | A1 | 5/2004 | Shaolian et al. |
| 2004/0093083 | A1 | 5/2004 | Branch et al. |
| 2004/0097924 | A1 | 5/2004 | Lambrecht et al. |
| 2004/0097930 | A1 | 5/2004 | Justis et al. |
| 2004/0097932 | A1 | 5/2004 | Ray et al. |
| 2004/0097941 | A1 | 5/2004 | Weiner et al. |
| 2004/0097973 | A1 | 5/2004 | Loshakove et al. |
| 2004/0098131 | A1 | 5/2004 | Bryan et al. |
| 2004/0102774 | A1 | 5/2004 | Trieu |
| 2004/0102784 | A1 | 5/2004 | Pasquet et al. |
| 2004/0102846 | A1 | 5/2004 | Keller et al. |
| 2004/0106925 | A1 | 6/2004 | Culbert |
| 2004/0106940 | A1 | 6/2004 | Shaolian et al. |
| 2004/0111161 | A1 | 6/2004 | Trieu |
| 2004/0116997 | A1 | 6/2004 | Taylor et al. |
| 2004/0117019 | A1 | 6/2004 | Trieu et al. |
| 2004/0117022 | A1 | 6/2004 | Marnay et al. |
| 2004/0127906 | A1 | 7/2004 | Culbert et al. |
| 2004/0127990 | A1 | 7/2004 | Bartish et al. |
| 2004/0127991 | A1 | 7/2004 | Ferree |
| 2004/0133124 | A1 | 7/2004 | Bates et al. |
| 2004/0133229 | A1 | 7/2004 | Lambrecht et al. |
| 2004/0133279 | A1 | 7/2004 | Krueger et al. |
| 2004/0133280 | A1 | 7/2004 | Trieu |
| 2004/0138748 | A1 | 7/2004 | Boyer et al. |
| 2004/0143284 | A1 | 7/2004 | Chin |
| 2004/0143332 | A1 | 7/2004 | Krueger et al. |
| 2004/0143734 | A1 | 7/2004 | Buer et al. |
| 2004/0147129 | A1 | 7/2004 | Rolfson |
| 2004/0147877 | A1 | 7/2004 | Heuser |
| 2004/0147950 | A1 | 7/2004 | Mueller et al. |
| 2004/0148027 | A1 | 7/2004 | Errico et al. |
| 2004/0153064 | A1 | 8/2004 | Foley et al. |
| 2004/0153065 | A1 | 8/2004 | Lim |
| 2004/0153115 | A1 | 8/2004 | Reiley et al. |
| 2004/0153156 | A1 | 8/2004 | Cohen et al. |
| 2004/0153160 | A1 | 8/2004 | Carrasco |
| 2004/0158206 | A1 | 8/2004 | Aboul-Hosn et al. |
| 2004/0158258 | A1 | 8/2004 | Bonati et al. |
| 2004/0162617 | A1 | 8/2004 | Zucherman et al. |
| 2004/0162618 | A1 | 8/2004 | Mujwid et al. |
| 2004/0167561 | A1 | 8/2004 | Boucher et al. |
| 2004/0167562 | A1 | 8/2004 | Osorio et al. |
| 2004/0167625 | A1 | 8/2004 | Beyar et al. |
| 2004/0172133 | A1 | 9/2004 | Gerber et al. |
| 2004/0172134 | A1 | 9/2004 | Berry |
| 2004/0176775 | A1 | 9/2004 | Burkus et al. |
| 2004/0186052 | A1 | 9/2004 | Iyer et al. |
| 2004/0186471 | A1 | 9/2004 | Trieu |
| 2004/0186482 | A1 | 9/2004 | Kolb et al. |
| 2004/0186528 | A1 | 9/2004 | Ries et al. |
| 2004/0186570 | A1 | 9/2004 | Rapp |
| 2004/0186573 | A1 | 9/2004 | Ferree |
| 2004/0186577 | A1 | 9/2004 | Ferree |

(56) References Cited

U.S. PATENT DOCUMENTS

2004/0193271 A1 9/2004 Fraser et al.
2004/0193277 A1 9/2004 Long et al.
2004/0199162 A1 10/2004 Von et al.
2004/0210231 A1 10/2004 Boucher et al.
2004/0210310 A1 10/2004 Trieu
2004/0215343 A1 10/2004 Hochschuler et al.
2004/0215344 A1 10/2004 Hochschuler et al.
2004/0220580 A1 11/2004 Johnson et al.
2004/0220668 A1 11/2004 Eisermann et al.
2004/0220669 A1 11/2004 Studer
2004/0220672 A1 11/2004 Shadduck
2004/0225292 A1 11/2004 Sasso et al.
2004/0225296 A1 11/2004 Reiss et al.
2004/0225361 A1 11/2004 Glenn et al.
2004/0230191 A1 11/2004 Frey et al.
2004/0230309 A1 11/2004 DiMauro
2004/0243229 A1 12/2004 Vidlund et al.
2004/0243239 A1 12/2004 Taylor
2004/0243241 A1 12/2004 Istephanous et al.
2004/0249377 A1 12/2004 Kaes et al.
2004/0249461 A1 12/2004 Ferree
2004/0249466 A1 12/2004 Liu et al.
2004/0254520 A1 12/2004 Porteous et al.
2004/0254575 A1 12/2004 Obenchain et al.
2004/0254643 A1 12/2004 Jackson
2004/0254644 A1 12/2004 Taylor
2004/0260297 A1 12/2004 Padget et al.
2004/0260300 A1 12/2004 Gorensek et al.
2004/0260397 A1 12/2004 Lambrecht et al.
2004/0266257 A1 12/2004 Ries et al.
2004/0267271 A9 12/2004 Scribner et al.
2004/0267367 A1 12/2004 O'Neil
2005/0004578 A1 1/2005 Lambrecht et al.
2005/0010292 A1 1/2005 Carrasco
2005/0010293 A1 1/2005 Zucherman et al.
2005/0010298 A1 1/2005 Zucherman et al.
2005/0015148 A1 1/2005 Jansen et al.
2005/0015152 A1 1/2005 Sweeney
2005/0019365 A1 1/2005 Frauchiger et al.
2005/0021041 A1 1/2005 Michelson
2005/0027360 A1 2/2005 Webb et al.
2005/0033289 A1 2/2005 Warren et al.
2005/0033295 A1 2/2005 Wisnewski
2005/0033434 A1 2/2005 Berry
2005/0033440 A1 2/2005 Lambrecht et al.
2005/0038431 A1 2/2005 Bartish et al.
2005/0038515 A1 2/2005 Kunzler
2005/0038517 A1 2/2005 Carrison et al.
2005/0043737 A1 2/2005 Reiley et al.
2005/0043796 A1 2/2005 Grant et al.
2005/0054948 A1 3/2005 Goldenberg
2005/0055097 A1 3/2005 Grunberg et al.
2005/0060036 A1 3/2005 Schultz et al.
2005/0060038 A1 3/2005 Lambrecht et al.
2005/0065519 A1 3/2005 Michelson
2005/0065609 A1 3/2005 Wardlaw
2005/0065610 A1 3/2005 Pisharodi
2005/0069571 A1 3/2005 Slivka et al.
2005/0070908 A1 3/2005 Cragg
2005/0070911 A1 3/2005 Carrison et al.
2005/0070913 A1 3/2005 Milbocker et al.
2005/0071011 A1 3/2005 Ralph et al.
2005/0080443 A1 4/2005 Fallin et al.
2005/0080488 A1 4/2005 Schultz
2005/0085912 A1 4/2005 Arnin et al.
2005/0090443 A1 4/2005 Reed
2005/0090833 A1 4/2005 DiPoto
2005/0090852 A1 4/2005 Layne et al.
2005/0090899 A1 4/2005 DiPoto
2005/0096745 A1 5/2005 Andre et al.
2005/0102202 A1 5/2005 Linden et al.
2005/0107880 A1 5/2005 Shimp et al.
2005/0113916 A1 5/2005 Branch
2005/0113917 A1 5/2005 Chae et al.
2005/0113918 A1 5/2005 Messerli et al.
2005/0113919 A1 5/2005 Cragg et al.
2005/0113927 A1 5/2005 Malek
2005/0113928 A1 5/2005 Cragg et al.
2005/0118228 A1 6/2005 Trieu
2005/0118550 A1 6/2005 Turri
2005/0119657 A1 6/2005 Goldsmith
2005/0119662 A1 6/2005 Reiley et al.
2005/0119750 A1 6/2005 Studer
2005/0119751 A1 6/2005 Lawson
2005/0119752 A1 6/2005 Williams et al.
2005/0119754 A1 6/2005 Trieu et al.
2005/0124989 A1 6/2005 Suddaby
2005/0124992 A1 6/2005 Ferree
2005/0124999 A1 6/2005 Teitelbaum et al.
2005/0125062 A1 6/2005 Biedermann et al.
2005/0125066 A1 6/2005 McAfee
2005/0130929 A1 6/2005 Boyd
2005/0131267 A1 6/2005 Talmadge
2005/0131268 A1 6/2005 Talmadge
2005/0131269 A1 6/2005 Talmadge
2005/0131406 A1 6/2005 Reiley et al.
2005/0131409 A1 6/2005 Chervitz et al.
2005/0131411 A1 6/2005 Culbert
2005/0131536 A1 6/2005 Eisermann et al.
2005/0131538 A1 6/2005 Chervitz et al.
2005/0131540 A1 6/2005 Trieu
2005/0131541 A1 6/2005 Trieu
2005/0137595 A1 6/2005 Hoffmann et al.
2005/0137602 A1 6/2005 Assell et al.
2005/0142211 A1 6/2005 Wenz
2005/0143734 A1 6/2005 Cachia et al.
2005/0143763 A1 6/2005 Ortiz et al.
2005/0143827 A1 6/2005 Globerman et al.
2005/0149022 A1 7/2005 Shaolian et al.
2005/0149030 A1 7/2005 Serhan et al.
2005/0149034 A1 7/2005 Assell et al.
2005/0149191 A1 7/2005 Cragg et al.
2005/0149194 A1 7/2005 Ahlgren
2005/0149197 A1 7/2005 Cauthen
2005/0154396 A1 7/2005 Foley et al.
2005/0154463 A1 7/2005 Trieu
2005/0154467 A1 7/2005 Peterman et al.
2005/0159819 A1 7/2005 McCormack et al.
2005/0165398 A1 7/2005 Reiley
2005/0165406 A1 7/2005 Assell et al.
2005/0165420 A1 7/2005 Cha
2005/0165484 A1 7/2005 Ferree
2005/0165485 A1 7/2005 Trieu
2005/0171539 A1 8/2005 Braun et al.
2005/0171541 A1 8/2005 Boehm et al.
2005/0171552 A1 8/2005 Johnson et al.
2005/0171608 A1 8/2005 Peterman et al.
2005/0171610 A1 8/2005 Humphreys et al.
2005/0177173 A1 8/2005 Aebi et al.
2005/0177235 A1 8/2005 Baynham et al.
2005/0177240 A1 8/2005 Blain
2005/0182412 A1 8/2005 Johnson et al.
2005/0182413 A1 8/2005 Johnson et al.
2005/0182414 A1 8/2005 Manzi et al.
2005/0182418 A1 8/2005 Boyd et al.
2005/0187556 A1 8/2005 Stack et al.
2005/0187558 A1 8/2005 Johnson et al.
2005/0187559 A1 8/2005 Raymond et al.
2005/0187564 A1 8/2005 Jayaraman
2005/0197702 A1 9/2005 Coppes et al.
2005/0197707 A1 9/2005 Trieu et al.
2005/0203512 A1 9/2005 Hawkins et al.
2005/0203515 A1 9/2005 Doherty et al.
2005/0216018 A1 9/2005 Sennett
2005/0216026 A1 9/2005 Culbert
2005/0216081 A1 9/2005 Taylor
2005/0216087 A1 9/2005 Zucherman et al.
2005/0222681 A1 10/2005 Richley et al.
2005/0222684 A1 10/2005 Ferree
2005/0228383 A1 10/2005 Zucherman et al.
2005/0228391 A1 10/2005 Levy et al.
2005/0228397 A1 10/2005 Malandain et al.
2005/0234425 A1 10/2005 Miller et al.
2005/0234451 A1 10/2005 Markworth

(56) References Cited

U.S. PATENT DOCUMENTS

2005/0234452 A1 10/2005 Malandain
2005/0234456 A1 10/2005 Malandain
2005/0240182 A1 10/2005 Zucherman et al.
2005/0240189 A1 10/2005 Rousseau et al.
2005/0240193 A1 10/2005 Layne et al.
2005/0240269 A1 10/2005 Lambrecht et al.
2005/0251142 A1 11/2005 Hoffmann et al.
2005/0251149 A1 11/2005 Wenz
2005/0251260 A1 11/2005 Gerber et al.
2005/0256525 A1 11/2005 Culbert et al.
2005/0256576 A1 11/2005 Moskowitz et al.
2005/0261682 A1 11/2005 Ferree
2005/0261684 A1 11/2005 Shaolian et al.
2005/0261695 A1 11/2005 Cragg et al.
2005/0261769 A1 11/2005 Moskowitz et al.
2005/0261781 A1 11/2005 Sennett et al.
2005/0267471 A1 12/2005 Biedermann et al.
2005/0273166 A1 12/2005 Sweeney
2005/0273173 A1 12/2005 Gordon et al.
2005/0277938 A1 12/2005 Parsons
2005/0278023 A1 12/2005 Zwirkoski
2005/0278026 A1 12/2005 Gordon et al.
2005/0278027 A1 12/2005 Hyde, Jr.
2005/0278029 A1 12/2005 Trieu
2005/0283238 A1 12/2005 Reiley
2005/0283244 A1 12/2005 Gordon et al.
2005/0287071 A1 12/2005 Wenz
2006/0004326 A1 1/2006 Collins et al.
2006/0004456 A1 1/2006 McKay
2006/0004457 A1 1/2006 Collins et al.
2006/0004458 A1 1/2006 Collins et al.
2006/0009778 A1 1/2006 Collins et al.
2006/0009779 A1 1/2006 Collins et al.
2006/0009851 A1 1/2006 Collins et al.
2006/0015105 A1 1/2006 Warren et al.
2006/0015119 A1 1/2006 Plassky et al.
2006/0020284 A1 1/2006 Foley et al.
2006/0022180 A1 2/2006 Selness
2006/0030850 A1 2/2006 Keegan et al.
2006/0030872 A1 2/2006 Culbert et al.
2006/0030933 A1 2/2006 Delegge et al.
2006/0030943 A1 2/2006 Peterman
2006/0036241 A1 2/2006 Siegal
2006/0036244 A1 2/2006 Spitler et al.
2006/0036246 A1 2/2006 Carl et al.
2006/0036256 A1 2/2006 Carl et al.
2006/0036259 A1 2/2006 Carl et al.
2006/0036261 A1 2/2006 McDonnell
2006/0036273 A1 2/2006 Siegal
2006/0036323 A1 2/2006 Carl et al.
2006/0036324 A1 2/2006 Sachs et al.
2006/0041258 A1 2/2006 Galea
2006/0041314 A1 2/2006 Millard
2006/0045904 A1 3/2006 Aronson
2006/0058790 A1 3/2006 Carl et al.
2006/0058807 A1 3/2006 Landry et al.
2006/0058876 A1 3/2006 McKinley
2006/0058880 A1 3/2006 Wysocki
2006/0064101 A1 3/2006 Arramon
2006/0064102 A1 3/2006 Ebner
2006/0064171 A1 3/2006 Trieu
2006/0064172 A1 3/2006 Trieu
2006/0069436 A1 3/2006 Sutton et al.
2006/0069439 A1 3/2006 Zucherman et al.
2006/0069440 A1 3/2006 Zucherman et al.
2006/0074429 A1 4/2006 Ralph et al.
2006/0079908 A1 4/2006 Lieberman
2006/0084867 A1 4/2006 Tremblay et al.
2006/0084977 A1 4/2006 Lieberman
2006/0084988 A1 4/2006 Kim
2006/0085002 A1 4/2006 Trieu et al.
2006/0085009 A1 4/2006 Truckai et al.
2006/0085010 A1 4/2006 Lieberman
2006/0089642 A1 4/2006 Diaz et al.
2006/0089646 A1 4/2006 Bonutti
2006/0089654 A1 4/2006 Lins et al.
2006/0089715 A1 4/2006 Truckai et al.
2006/0089718 A1 4/2006 Zucherman et al.
2006/0089719 A1 4/2006 Trieu
2006/0095045 A1 5/2006 Trieu
2006/0095046 A1 5/2006 Trieu et al.
2006/0095134 A1 5/2006 Trieu et al.
2006/0095138 A1 5/2006 Truckai et al.
2006/0100622 A1 5/2006 Jackson
2006/0100706 A1 5/2006 Shadduck et al.
2006/0100707 A1 5/2006 Stinson et al.
2006/0106381 A1 5/2006 Ferree et al.
2006/0106397 A1 5/2006 Lins
2006/0106459 A1 5/2006 Truckai et al.
2006/0111715 A1 5/2006 Jackson
2006/0111728 A1 5/2006 Abdou
2006/0111785 A1 5/2006 O'Neil
2006/0119629 A1 6/2006 An et al.
2006/0122609 A1 6/2006 Mirkovic et al.
2006/0122610 A1 6/2006 Culbert et al.
2006/0122701 A1 6/2006 Kiester
2006/0122703 A1 6/2006 Aebi et al.
2006/0122704 A1 6/2006 Vresilovic et al.
2006/0129244 A1 6/2006 Ensign
2006/0136062 A1 6/2006 DiNello et al.
2006/0136063 A1 6/2006 Zeegers
2006/0136064 A1 6/2006 Sherman
2006/0142759 A1 6/2006 Arnin et al.
2006/0142765 A9 6/2006 Dixon et al.
2006/0142776 A1 6/2006 Iwanari
2006/0142858 A1 6/2006 Colleran et al.
2006/0142864 A1 6/2006 Cauthen
2006/0149136 A1 7/2006 Seto et al.
2006/0149237 A1 7/2006 Markworth et al.
2006/0149252 A1 7/2006 Markworth et al.
2006/0149379 A1 7/2006 Kuslich et al.
2006/0149380 A1 7/2006 Lotz et al.
2006/0149385 A1 7/2006 McKay
2006/0155379 A1 7/2006 Heneveld et al.
2006/0161162 A1 7/2006 Lambrecht et al.
2006/0161166 A1 7/2006 Johnson et al.
2006/0167547 A1 7/2006 Suddaby
2006/0167553 A1 7/2006 Cauthen et al.
2006/0173545 A1 8/2006 Cauthen et al.
2006/0178743 A1 8/2006 Carter
2006/0178745 A1 8/2006 Bartish et al.
2006/0178746 A1 8/2006 Bartish et al.
2006/0184192 A1 8/2006 Markworth et al.
2006/0184247 A1 8/2006 Edidin et al.
2006/0184248 A1 8/2006 Edidin et al.
2006/0189999 A1 8/2006 Zwirkoski
2006/0190083 A1 8/2006 Arnin et al.
2006/0190085 A1 8/2006 Cauthen
2006/0195102 A1 8/2006 Malandain
2006/0195103 A1 8/2006 Padget et al.
2006/0195191 A1 8/2006 Sweeney et al.
2006/0200139 A1 9/2006 Michelson
2006/0200164 A1 9/2006 Michelson
2006/0200239 A1 9/2006 Rothman et al.
2006/0200240 A1 9/2006 Rothman et al.
2006/0200241 A1 9/2006 Rothman et al.
2006/0200242 A1 9/2006 Rothman et al.
2006/0200243 A1 9/2006 Rothman et al.
2006/0206116 A1 9/2006 Yeung
2006/0206207 A1 9/2006 Dryer et al.
2006/0212118 A1 9/2006 Abernathie
2006/0217711 A1 9/2006 Stevens et al.
2006/0229627 A1 10/2006 Hunt et al.
2006/0229629 A1 10/2006 Manzi et al.
2006/0235403 A1 10/2006 Blain
2006/0235412 A1 10/2006 Blain
2006/0235423 A1 10/2006 Cantu
2006/0235521 A1 10/2006 Zucherman et al.
2006/0235531 A1 10/2006 Buettner
2006/0241643 A1 10/2006 Lim et al.
2006/0241663 A1 10/2006 Rice et al.
2006/0241770 A1 10/2006 Rhoda et al.
2006/0247634 A1 11/2006 Warner et al.
2006/0247770 A1 11/2006 Peterman

(56) References Cited

U.S. PATENT DOCUMENTS

2006/0247771 A1 11/2006 Peterman et al.
2006/0247781 A1 11/2006 Francis
2006/0253120 A1 11/2006 Anderson et al.
2006/0253201 A1 11/2006 McLuen
2006/0254784 A1 11/2006 Hartmann et al.
2006/0264896 A1 11/2006 Palmer
2006/0264939 A1 11/2006 Zucherman et al.
2006/0264945 A1 11/2006 Edidin et al.
2006/0265067 A1 11/2006 Zucherman et al.
2006/0265075 A1 11/2006 Baumgartner et al.
2006/0265077 A1 11/2006 Zwirkoski
2006/0271049 A1 11/2006 Zucherman et al.
2006/0271061 A1 11/2006 Beyar et al.
2006/0276897 A1 12/2006 Winslow et al.
2006/0276899 A1 12/2006 Zipnick et al.
2006/0276901 A1 12/2006 Zipnick et al.
2006/0276902 A1 12/2006 Zipnick et al.
2006/0282167 A1 12/2006 Lambrecht et al.
2006/0287726 A1 12/2006 Segal et al.
2006/0287727 A1 12/2006 Segal et al.
2006/0293662 A1 12/2006 Boyer et al.
2006/0293663 A1 12/2006 Walkenhorst et al.
2006/0293753 A1 12/2006 Thramann
2007/0006692 A1 1/2007 Phan
2007/0010716 A1 1/2007 Malandain et al.
2007/0010717 A1 1/2007 Cragg
2007/0010824 A1 1/2007 Malandain et al.
2007/0010826 A1 1/2007 Rhoda et al.
2007/0010844 A1 1/2007 Gong et al.
2007/0010845 A1 1/2007 Gong et al.
2007/0010846 A1 1/2007 Leung et al.
2007/0010848 A1 1/2007 Leung et al.
2007/0010886 A1 1/2007 Banick et al.
2007/0010889 A1 1/2007 Francis
2007/0016191 A1 1/2007 Culbert et al.
2007/0032703 A1 2/2007 Sankaran et al.
2007/0032790 A1 2/2007 Aschmann et al.
2007/0032791 A1 2/2007 Greenhalgh
2007/0043361 A1 2/2007 Malandain et al.
2007/0043362 A1 2/2007 Malandain et al.
2007/0043363 A1 2/2007 Malandain et al.
2007/0043440 A1 2/2007 William et al.
2007/0048382 A1 3/2007 Meyer et al.
2007/0049849 A1 3/2007 Schwardt et al.
2007/0049934 A1 3/2007 Edidin et al.
2007/0049935 A1 3/2007 Edidin et al.
2007/0050034 A1 3/2007 Schwardt et al.
2007/0050035 A1 3/2007 Schwardt et al.
2007/0055201 A1 3/2007 Seto et al.
2007/0055236 A1 3/2007 Hudgins et al.
2007/0055237 A1 3/2007 Edidin et al.
2007/0055246 A1 3/2007 Zucherman et al.
2007/0055264 A1 3/2007 Parmigiani
2007/0055265 A1 3/2007 Schaller
2007/0055266 A1 3/2007 Osorio et al.
2007/0055267 A1 3/2007 Osorio et al.
2007/0055271 A1 3/2007 Schaller
2007/0055272 A1 3/2007 Schaller
2007/0055273 A1 3/2007 Schaller
2007/0055274 A1 3/2007 Appenzeller et al.
2007/0055275 A1 3/2007 Schaller
2007/0055276 A1 3/2007 Edidin
2007/0055277 A1 3/2007 Osorio et al.
2007/0055278 A1 3/2007 Osorio et al.
2007/0055281 A1 3/2007 Osorio et al.
2007/0055284 A1 3/2007 Osorio et al.
2007/0055300 A1 3/2007 Osorio et al.
2007/0055377 A1 3/2007 Hanson et al.
2007/0060933 A1 3/2007 Sankaran et al.
2007/0060935 A1 3/2007 Schwardt et al.
2007/0067034 A1 3/2007 Chirico et al.
2007/0067035 A1 3/2007 Falahee
2007/0068329 A1 3/2007 Phan et al.
2007/0073292 A1 3/2007 Kohm et al.
2007/0073399 A1 3/2007 Zipnick et al.
2007/0078436 A1 4/2007 Leung et al.
2007/0078463 A1 4/2007 Malandain
2007/0093689 A1 4/2007 Steinberg
2007/0093897 A1 4/2007 Gerbec et al.
2007/0093899 A1 4/2007 Dutoit et al.
2007/0093901 A1 4/2007 Grotz et al.
2007/0093906 A1 4/2007 Hudgins et al.
2007/0118132 A1 5/2007 Culbert et al.
2007/0118222 A1 5/2007 Lang
2007/0118223 A1 5/2007 Allard et al.
2007/0123868 A1 5/2007 Culbert et al.
2007/0123891 A1 5/2007 Ries et al.
2007/0123892 A1 5/2007 Ries et al.
2007/0123986 A1 5/2007 Schaller
2007/0129730 A1 6/2007 Woods et al.
2007/0135922 A1 6/2007 Trieu
2007/0142843 A1 6/2007 Dye
2007/0149978 A1 6/2007 Shezifi et al.
2007/0150059 A1 6/2007 Ruberte et al.
2007/0150060 A1 6/2007 Trieu
2007/0150061 A1 6/2007 Trieu
2007/0150063 A1 6/2007 Ruberte et al.
2007/0150064 A1 6/2007 Ruberte et al.
2007/0161992 A1 7/2007 Kwak et al.
2007/0162005 A1 7/2007 Peterson et al.
2007/0162127 A1 7/2007 Peterman et al.
2007/0162132 A1 7/2007 Messerli
2007/0162138 A1 7/2007 Heinz
2007/0167945 A1 7/2007 Lange et al.
2007/0168036 A1 7/2007 Ainsworth et al.
2007/0168038 A1 7/2007 Trieu
2007/0173939 A1 7/2007 Kim et al.
2007/0173940 A1 7/2007 Hestad et al.
2007/0178222 A1 8/2007 Storey et al.
2007/0179612 A1 8/2007 Johnson et al.
2007/0179615 A1 8/2007 Heinz et al.
2007/0179616 A1 8/2007 Braddock et al.
2007/0179618 A1 8/2007 Trieu et al.
2007/0185578 A1 8/2007 O'Neil et al.
2007/0191953 A1 8/2007 Trieu
2007/0191954 A1 8/2007 Hansell et al.
2007/0191959 A1 8/2007 Hartmann et al.
2007/0197935 A1 8/2007 Reiley et al.
2007/0198023 A1 8/2007 Sand et al.
2007/0198025 A1 8/2007 Trieu et al.
2007/0198089 A1 8/2007 Moskowitz et al.
2007/0203491 A1 8/2007 Pasquet et al.
2007/0208423 A1 9/2007 Messerli et al.
2007/0208426 A1 9/2007 Trieu
2007/0213717 A1 9/2007 Trieu et al.
2007/0213737 A1 9/2007 Schermerhorn et al.
2007/0213826 A1 9/2007 Smith et al.
2007/0219634 A1 9/2007 Greenhalgh et al.
2007/0225706 A1 9/2007 Clark et al.
2007/0225726 A1 9/2007 Dye et al.
2007/0225807 A1 9/2007 Phan et al.
2007/0225815 A1 9/2007 Keith et al.
2007/0233074 A1 10/2007 Anderson et al.
2007/0233076 A1 10/2007 Trieu
2007/0233083 A1 10/2007 Abdou
2007/0233089 A1 10/2007 DiPoto et al.
2007/0233130 A1 10/2007 Suddaby
2007/0233244 A1 10/2007 Lopez et al.
2007/0233254 A1 10/2007 Grotz et al.
2007/0239278 A1 10/2007 Heinz
2007/0250167 A1 10/2007 Bray et al.
2007/0260245 A1 11/2007 Malandain et al.
2007/0260255 A1 11/2007 Haddock et al.
2007/0260314 A1 11/2007 Biyani
2007/0270823 A1 11/2007 Trieu et al.
2007/0270954 A1 11/2007 Wu
2007/0270957 A1 11/2007 Heinz
2007/0270968 A1 11/2007 Baynham et al.
2007/0276373 A1 11/2007 Malandain
2007/0276375 A1 11/2007 Rapp
2007/0276497 A1 11/2007 Anderson
2007/0282443 A1 12/2007 Globerman et al.
2007/0282449 A1 12/2007 De et al.
2007/0288091 A1 12/2007 Braddock et al.

(56) References Cited

U.S. PATENT DOCUMENTS

2007/0299521 A1 12/2007 Glenn
2008/0009877 A1 1/2008 Sankaran et al.
2008/0015694 A1 1/2008 Tribus
2008/0015701 A1 1/2008 Garcia et al.
2008/0021556 A1 1/2008 Edie
2008/0021557 A1 1/2008 Trieu
2008/0021558 A1 1/2008 Thramann
2008/0021559 A1 1/2008 Thramann
2008/0027437 A1 1/2008 Johnson et al.
2008/0027438 A1 1/2008 Abdou
2008/0027453 A1 1/2008 Johnson et al.
2008/0027454 A1 1/2008 Johnson et al.
2008/0027544 A1 1/2008 Melkent
2008/0027550 A1 1/2008 Link et al.
2008/0033440 A1 2/2008 Moskowitz et al.
2008/0033480 A1 2/2008 Hardert
2008/0045966 A1 2/2008 Buttermann et al.
2008/0051890 A1 2/2008 Waugh et al.
2008/0051897 A1 2/2008 Lopez et al.
2008/0051902 A1 2/2008 Dwyer
2008/0058598 A1 3/2008 Ries et al.
2008/0058937 A1 3/2008 Malandain et al.
2008/0058944 A1 3/2008 Duplessis et al.
2008/0065082 A1 3/2008 Chang et al.
2008/0065219 A1 3/2008 Dye
2008/0071356 A1 3/2008 Greenhalgh et al.
2008/0071380 A1 3/2008 Sweeney
2008/0077148 A1 3/2008 Ries et al.
2008/0077150 A1 3/2008 Nguyen
2008/0077241 A1 3/2008 Nguyen
2008/0082172 A1 4/2008 Jackson
2008/0082173 A1 4/2008 Delurio et al.
2008/0097436 A1 4/2008 Culbert et al.
2008/0097454 A1 4/2008 Deridder et al.
2008/0097611 A1 4/2008 Mastrorio et al.
2008/0103601 A1 5/2008 Biro et al.
2008/0108990 A1 5/2008 Mitchell et al.
2008/0108996 A1 5/2008 Padget et al.
2008/0119935 A1 5/2008 Alvarez
2008/0125865 A1 5/2008 Abdelgany
2008/0132934 A1 6/2008 Reiley
2008/0133012 A1 6/2008 McGuckin
2008/0133017 A1 6/2008 Beyar et al.
2008/0140085 A1 6/2008 Gately et al.
2008/0140207 A1 6/2008 Olmos et al.
2008/0147129 A1 6/2008 Biedermann et al.
2008/0147193 A1 6/2008 Matthis et al.
2008/0154377 A1 6/2008 Voellmicke et al.
2008/0154379 A1 6/2008 Steiner et al.
2008/0161927 A1 7/2008 Savage
2008/0167657 A1 7/2008 Greenhalgh
2008/0172128 A1 7/2008 Perez-Cruet et al.
2008/0177306 A1 7/2008 Lamborne et al.
2008/0177312 A1 7/2008 Perez-Cruet et al.
2008/0177388 A1 7/2008 Patterson et al.
2008/0183204 A1 7/2008 Greenhalgh et al.
2008/0188945 A1 8/2008 Boyce et al.
2008/0195096 A1 8/2008 Frei
2008/0195209 A1 8/2008 Garcia et al.
2008/0195210 A1 8/2008 Milijasevic et al.
2008/0208255 A1 8/2008 Siegal
2008/0208344 A1 8/2008 Kilpela et al.
2008/0221586 A1 9/2008 Garcia-Bengochea et al.
2008/0221687 A1 9/2008 Viker
2008/0228225 A1 9/2008 Trautwein et al.
2008/0229597 A1 9/2008 Malandain
2008/0234732 A1 9/2008 Landry et al.
2008/0234733 A1 9/2008 Scrantz et al.
2008/0243126 A1 10/2008 Gutierrez et al.
2008/0243251 A1 10/2008 Stad et al.
2008/0243254 A1 10/2008 Butler
2008/0249622 A1 10/2008 Gray
2008/0249628 A1 10/2008 Altarac et al.
2008/0255563 A1 10/2008 Farr et al.
2008/0255574 A1 10/2008 Dye
2008/0255618 A1 10/2008 Fisher et al.
2008/0262619 A1 10/2008 Ray
2008/0269904 A1 10/2008 Voorhies
2008/0281346 A1 11/2008 Greenhalgh et al.
2008/0281364 A1 11/2008 Chirico et al.
2008/0281425 A1 11/2008 Thalgott
2008/0287981 A1 11/2008 Culbert et al.
2008/0287997 A1 11/2008 Altarac et al.
2008/0300685 A1 12/2008 Carls et al.
2008/0306537 A1 12/2008 Culbert
2008/0312743 A1 12/2008 Vila et al.
2008/0319477 A1 12/2008 Justis et al.
2009/0005870 A1 1/2009 Hawkins et al.
2009/0005873 A1 1/2009 Slivka et al.
2009/0018524 A1 1/2009 Greenhalgh et al.
2009/0030423 A1 1/2009 Puno
2009/0048631 A1 2/2009 Bhatnagar et al.
2009/0048678 A1 2/2009 Saal et al.
2009/0054898 A1 2/2009 Gleason
2009/0054911 A1 2/2009 Mueller et al.
2009/0054988 A1 2/2009 Hess
2009/0054991 A1 2/2009 Biyani et al.
2009/0062807 A1 3/2009 Song
2009/0069813 A1 3/2009 Von et al.
2009/0069895 A1 3/2009 Gittings et al.
2009/0076607 A1 3/2009 Aalsma et al.
2009/0076610 A1 3/2009 Afzal
2009/0088789 A1 4/2009 O'Neil et al.
2009/0099568 A1 4/2009 Lowry et al.
2009/0105712 A1 4/2009 Dauster
2009/0105745 A1 4/2009 Culbert
2009/0112217 A1 4/2009 Hester
2009/0112320 A1 4/2009 Kraus
2009/0112324 A1 4/2009 Refai et al.
2009/0131986 A1 5/2009 Lee et al.
2009/0149857 A1 6/2009 Culbert et al.
2009/0164020 A1 6/2009 Janowski
2009/0177281 A1 7/2009 Swanson et al.
2009/0177284 A1 7/2009 Rogers et al.
2009/0182429 A1 7/2009 Humphreys et al.
2009/0192613 A1 7/2009 Wing et al.
2009/0192614 A1 7/2009 Beger et al.
2009/0198339 A1 8/2009 Kleiner
2009/0216234 A1 8/2009 Farr et al.
2009/0221967 A1 9/2009 Thommen et al.
2009/0222043 A1 9/2009 Altarac et al.
2009/0222096 A1 9/2009 Trieu
2009/0222099 A1 9/2009 Liu et al.
2009/0222100 A1 9/2009 Cipoletti et al.
2009/0234364 A1 9/2009 Crook
2009/0234389 A1 9/2009 Chuang et al.
2009/0234398 A1 9/2009 Chirico et al.
2009/0240333 A1 9/2009 Trudeau et al.
2009/0240334 A1 9/2009 Richelsoph
2009/0240335 A1 9/2009 Arcenio et al.
2009/0248159 A1 10/2009 Aflatoon
2009/0248163 A1 10/2009 King et al.
2009/0275890 A1 11/2009 Leibowitz et al.
2009/0276049 A1 11/2009 Weiland
2009/0276051 A1 11/2009 Arramon et al.
2009/0292361 A1 11/2009 Lopez et al.
2009/0299479 A1 12/2009 Jones et al.
2010/0016905 A1 1/2010 Greenhalgh et al.
2010/0016968 A1 1/2010 Moore
2010/0024779 A1 2/2010 Makita
2010/0030217 A1 2/2010 Mitusina
2010/0040332 A1 2/2010 Van et al.
2010/0042218 A1 2/2010 Nebosky et al.
2010/0049324 A1 2/2010 Valdevit et al.
2010/0057204 A1 3/2010 Kadaba et al.
2010/0070036 A1 3/2010 Implicito
2010/0076492 A1 3/2010 Warner et al.
2010/0076502 A1 3/2010 Guyer et al.
2010/0076559 A1 3/2010 Bagga
2010/0082109 A1 4/2010 Greenhalgh et al.
2010/0094422 A1 4/2010 Hansell et al.
2010/0094424 A1 4/2010 Woodburn et al.
2010/0094426 A1 4/2010 Grohowski et al.
2010/0100098 A1 4/2010 Norton et al.

(56) References Cited

U.S. PATENT DOCUMENTS

2010/0100183 A1 4/2010 Prewett et al.
2010/0106191 A1 4/2010 Yue et al.
2010/0114105 A1 5/2010 Butters
2010/0114147 A1 5/2010 Biyani
2010/0125334 A1 5/2010 Krueger
2010/0174314 A1 7/2010 Mirkovic et al.
2010/0179594 A1 7/2010 Theofilos et al.
2010/0185290 A1 7/2010 Compton et al.
2010/0185292 A1 7/2010 Hochschuler et al.
2010/0191241 A1 7/2010 McCormack et al.
2010/0191334 A1 7/2010 Keller
2010/0191336 A1 7/2010 Greenhalgh
2010/0204795 A1 8/2010 Greenhalgh
2010/0204796 A1 8/2010 Bae et al.
2010/0211107 A1 8/2010 Muhanna
2010/0211176 A1 8/2010 Greenhalgh
2010/0211182 A1 8/2010 Zimmermann
2010/0217269 A1 8/2010 Landes
2010/0222884 A1 9/2010 Greenhalgh
2010/0234849 A1 9/2010 Bouadi
2010/0234956 A1 9/2010 Attia et al.
2010/0241231 A1 9/2010 Marino et al.
2010/0249935 A1 9/2010 Slivka et al.
2010/0256768 A1 10/2010 Lim et al.
2010/0262240 A1 10/2010 Chavatte et al.
2010/0268231 A1 10/2010 Kuslich et al.
2010/0268338 A1 10/2010 Melkent et al.
2010/0274358 A1 10/2010 Mueller et al.
2010/0286777 A1 11/2010 Errico et al.
2010/0286783 A1 11/2010 Lechmann et al.
2010/0292700 A1 11/2010 Ries
2010/0298938 A1 11/2010 Humphreys et al.
2010/0305700 A1 12/2010 Ben-Arye et al.
2010/0305704 A1 12/2010 Messerli et al.
2010/0324607 A1 12/2010 Davis
2010/0324683 A1 12/2010 Reichen et al.
2010/0331845 A1 12/2010 Foley et al.
2010/0331891 A1 12/2010 Culbert et al.
2011/0004216 A1 1/2011 Amendola et al.
2011/0004308 A1 1/2011 Marino et al.
2011/0004310 A1 1/2011 Michelson
2011/0009970 A1 1/2011 Puno
2011/0015747 A1 1/2011 McManus et al.
2011/0029082 A1 2/2011 Hall
2011/0029083 A1 2/2011 Hynes et al.
2011/0029085 A1 2/2011 Hynes et al.
2011/0029086 A1 2/2011 Glazer et al.
2011/0035011 A1 2/2011 Cain
2011/0040332 A1 2/2011 Culbert et al.
2011/0046674 A1 2/2011 Calvosa et al.
2011/0054538 A1 3/2011 Zehavi et al.
2011/0066186 A1 3/2011 Boyer et al.
2011/0071527 A1 3/2011 Nelson et al.
2011/0082552 A1 4/2011 Wistrom et al.
2011/0093074 A1 4/2011 Glerum et al.
2011/0093076 A1 4/2011 Reo et al.
2011/0098531 A1 4/2011 To
2011/0098628 A1 4/2011 Yeung et al.
2011/0098818 A1 4/2011 Brodke et al.
2011/0112586 A1 5/2011 Guyer et al.
2011/0118840 A1 5/2011 Huntsman et al.
2011/0130835 A1 6/2011 Ashley et al.
2011/0130838 A1 6/2011 Lopez
2011/0144692 A1 6/2011 Saladin et al.
2011/0144753 A1 6/2011 Marchek et al.
2011/0153020 A1 6/2011 Abdelgany et al.
2011/0159070 A1 6/2011 Jin et al.
2011/0160773 A1 6/2011 Aschmann et al.
2011/0160866 A1 6/2011 Laurence et al.
2011/0172716 A1 7/2011 Glerum
2011/0172774 A1 7/2011 Varela
2011/0190816 A1 8/2011 Sheffer et al.
2011/0190891 A1 8/2011 Suh et al.
2011/0230971 A1 9/2011 Donner et al.
2011/0238072 A1 9/2011 Tyndall
2011/0251690 A1 10/2011 Berger et al.
2011/0270261 A1 11/2011 Mast et al.
2011/0276142 A1 11/2011 Niemiec et al.
2011/0282453 A1 11/2011 Greenhalgh et al.
2011/0282459 A1 11/2011 McClellan et al.
2011/0301711 A1 12/2011 Palmatier et al.
2011/0301712 A1 12/2011 Palmatier et al.
2011/0307010 A1 12/2011 Pradhan
2011/0313465 A1 12/2011 Warren et al.
2011/0319899 A1 12/2011 O'Neil et al.
2011/0319943 A1 12/2011 Donahoe et al.
2011/0319998 A1 12/2011 O'Neil et al.
2011/0320000 A1 12/2011 O'Neil
2012/0004726 A1 1/2012 Greenhalgh et al.
2012/0004732 A1 1/2012 Goel et al.
2012/0006361 A1 1/2012 Miyagi et al.
2012/0010715 A1 1/2012 Spann
2012/0022654 A1 1/2012 Farris et al.
2012/0029636 A1 2/2012 Ragab et al.
2012/0029639 A1 2/2012 Blackwell et al.
2012/0035730 A1 2/2012 Spann
2012/0059474 A1 3/2012 Weiman
2012/0059475 A1 3/2012 Weiman
2012/0071977 A1 3/2012 Oglaza et al.
2012/0071980 A1 3/2012 Purcell et al.
2012/0083887 A1 4/2012 Purcell et al.
2012/0083889 A1 4/2012 Purcell et al.
2012/0109319 A1 5/2012 Perisic
2012/0123546 A1 5/2012 Medina
2012/0136443 A1 5/2012 Wenzel
2012/0150304 A1 6/2012 Glerum et al.
2012/0150305 A1 6/2012 Glerum et al.
2012/0158146 A1 6/2012 Glerum et al.
2012/0158147 A1 6/2012 Glerum et al.
2012/0158148 A1 6/2012 Glerum et al.
2012/0185049 A1 7/2012 Varela
2012/0191204 A1 7/2012 Bae et al.
2012/0197299 A1 8/2012 Fabian, Jr.
2012/0197403 A1 8/2012 Merves
2012/0197405 A1 8/2012 Cuevas et al.
2012/0203290 A1 8/2012 Warren et al.
2012/0203347 A1 8/2012 Glerum et al.
2012/0209383 A1 8/2012 Tsuang et al.
2012/0215262 A1 8/2012 Culbert et al.
2012/0215315 A1 8/2012 Hochschuler et al.
2012/0215316 A1 8/2012 Mohr et al.
2012/0226357 A1 9/2012 Varela
2012/0232552 A1 9/2012 Morgenstern et al.
2012/0232658 A1 9/2012 Morgenstern et al.
2012/0253395 A1 10/2012 Linares
2012/0253406 A1 10/2012 Bae et al.
2012/0265309 A1 10/2012 Glerum et al.
2012/0277795 A1 11/2012 Von et al.
2012/0277869 A1 11/2012 Siccardi et al.
2012/0277877 A1 11/2012 Smith et al.
2012/0283837 A1 11/2012 Bae et al.
2012/0290090 A1 11/2012 Glerum et al.
2012/0290097 A1 11/2012 Cipoletti et al.
2012/0310350 A1 12/2012 Farris et al.
2012/0310352 A1 12/2012 DiMauro et al.
2012/0323327 A1 12/2012 McAfee
2012/0323328 A1 12/2012 Weiman
2012/0330421 A1 12/2012 Weiman
2012/0330422 A1 12/2012 Weiman
2013/0006361 A1 1/2013 Glerum et al.
2013/0006362 A1 1/2013 Biedermann et al.
2013/0023937 A1 1/2013 Biedermann et al.
2013/0023993 A1 1/2013 Weiman
2013/0023994 A1 1/2013 Glerum
2013/0030536 A1 1/2013 Rhoda et al.
2013/0030544 A1 1/2013 Studer
2013/0053966 A1 2/2013 Jimenez et al.
2013/0060337 A1 3/2013 Petersheim et al.
2013/0073044 A1 3/2013 Gamache
2013/0079790 A1 3/2013 Stein et al.
2013/0085572 A1 4/2013 Glerum et al.
2013/0085574 A1 4/2013 Sledge
2013/0109925 A1 5/2013 Horton et al.
2013/0110240 A1 5/2013 Hansell et al.

(56) References Cited

U.S. PATENT DOCUMENTS

2013/0116791 A1 5/2013 Theofilos
2013/0123924 A1 5/2013 Butler et al.
2013/0123927 A1 5/2013 Malandain
2013/0138214 A1 5/2013 Greenhalgh et al.
2013/0144387 A1 6/2013 Walker et al.
2013/0144388 A1 6/2013 Emery et al.
2013/0144391 A1 6/2013 Siegal et al.
2013/0150906 A1 6/2013 Kerboul et al.
2013/0158663 A1 6/2013 Miller et al.
2013/0158664 A1 6/2013 Palmatier et al.
2013/0158667 A1 6/2013 Tabor et al.
2013/0158668 A1 6/2013 Nichols et al.
2013/0158669 A1 6/2013 Sungarian et al.
2013/0173004 A1 7/2013 Greenhalgh et al.
2013/0190875 A1 7/2013 Shulock et al.
2013/0190876 A1 7/2013 Drochner et al.
2013/0190877 A1 7/2013 Medina
2013/0197647 A1 8/2013 Wolters et al.
2013/0204371 A1 8/2013 McLuen et al.
2013/0211525 A1 8/2013 McLuen et al.
2013/0211526 A1* 8/2013 Alheidt ..... A61F 2/4611 623/17.16
2013/0218276 A1 8/2013 Fiechter et al.
2013/0231747 A1 9/2013 Olmos et al.
2013/0238006 A1 9/2013 O'Neil et al.
2013/0253585 A1 9/2013 Garcia et al.
2013/0261746 A1 10/2013 Linares et al.
2013/0261747 A1 10/2013 Geisert
2013/0268077 A1 10/2013 You et al.
2013/0274883 A1 10/2013 McLuen et al.
2013/0310937 A1 11/2013 Luiz
2013/0310939 A1 11/2013 Fabian et al.
2013/0325128 A1 12/2013 Perloff et al.
2014/0018816 A1 1/2014 Fenn et al.
2014/0025169 A1 1/2014 Lechmann et al.
2014/0039622 A1 2/2014 Glerum et al. ..... A61F 2/4611 623/17.15
2014/0039626 A1 2/2014 Dale
2014/0046333 A1 2/2014 Johnson et al.
2014/0046446 A1 2/2014 Robinson
2014/0052259 A1 2/2014 Garner et al.
2014/0058512 A1 2/2014 Petersheim
2014/0058513 A1 2/2014 Gahman et al.
2014/0067073 A1 3/2014 Hauck
2014/0081267 A1 3/2014 Orsak et al.
2014/0086962 A1 3/2014 Jin et al.
2014/0094916 A1 4/2014 Glerum et al.
2014/0094917 A1 4/2014 Salerni
2014/0100662 A1 4/2014 Patterson
2014/0107790 A1 4/2014 Combrowski
2014/0114414 A1 4/2014 Abdou et al.
2014/0114423 A1 4/2014 Suedkamp et al.
2014/0121774 A1 5/2014 Glerum et al.
2014/0128977 A1 5/2014 Glerum et al.
2014/0128980 A1 5/2014 Kirschman
2014/0135934 A1 5/2014 Hansell et al.
2014/0142706 A1 5/2014 Hansell et al.
2014/0148904 A1 5/2014 Robinson
2014/0163682 A1 6/2014 Lott
2014/0163683 A1 6/2014 Seifert et al.
2014/0172103 A1 6/2014 O'Neil et al.
2014/0172105 A1 6/2014 Frasier et al.
2014/0172106 A1 6/2014 To et al.
2014/0180421 A1 6/2014 Glerum et al.
2014/0188225 A1 7/2014 Dmuschewsky
2014/0228959 A1 8/2014 Niemiec et al.
2014/0236296 A1 8/2014 Wagner et al.
2014/0243892 A1 8/2014 Choinski
2014/0243981 A1 8/2014 Davenport et al.
2014/0243982 A1 8/2014 Miller
2014/0249629 A1 9/2014 Moskowitz et al.
2014/0249630 A1 9/2014 Weiman
2014/0257484 A1 9/2014 Flower et al.
2014/0257486 A1 9/2014 Alheidt
2014/0257494 A1 9/2014 Thorwarth et al.
2014/0277139 A1 9/2014 Vrionis et al.
2014/0277204 A1 9/2014 Sandhu
2014/0277464 A1 9/2014 Richter et al.
2014/0277473 A1 9/2014 Perrow
2014/0277474 A1 9/2014 Robinson et al.
2014/0277476 A1 9/2014 McLean et al.
2014/0277481 A1 9/2014 Lee et al.
2014/0277507 A1 9/2014 Baynham
2014/0296983 A1 10/2014 Fauth et al.
2014/0303731 A1 10/2014 Glerum et al.
2014/0303732 A1 10/2014 Rhoda et al.
2014/0324171 A1 10/2014 Glerum et al.
2014/0336764 A1 11/2014 Masson et al.
2014/0336771 A1 11/2014 Zambiasi et al.
2014/0343678 A1 11/2014 Suddaby et al.
2015/0012097 A1 1/2015 Ibarra et al.
2015/0012098 A1 1/2015 Eastlack et al.
2015/0045894 A1 2/2015 Hawkins et al.
2015/0051701 A1 2/2015 Glerum et al.
2015/0057755 A1 2/2015 Suddaby et al.
2015/0066145 A1 3/2015 Rogers et al.
2015/0088256 A1 3/2015 Ballard
2015/0094610 A1 4/2015 Morgenstern et al.
2015/0094812 A1 4/2015 Cain
2015/0094813 A1 4/2015 Lechmann et al.
2015/0094814 A1 4/2015 Emerick et al.
2015/0100128 A1 4/2015 Glerum et al.
2015/0112398 A1 4/2015 Morgenstern et al.
2015/0112437 A1 4/2015 Davis et al.
2015/0112438 A1 4/2015 McLean
2015/0157470 A1 6/2015 Voellmicke et al.
2015/0164655 A1 6/2015 DiMauro
2015/0173914 A1 6/2015 DiMauro et al.
2015/0173916 A1 6/2015 Cain
2015/0182347 A1 7/2015 Robinson
2015/0190242 A1 7/2015 Blain et al.
2015/0196400 A1 7/2015 Dace
2015/0196401 A1 7/2015 DiMauro et al.
2015/0202052 A1 7/2015 DiMauro
2015/0216671 A1 8/2015 Cain
2015/0216672 A1 8/2015 Cain et al.
2015/0216673 A1 8/2015 DiMauro
2015/0230929 A1 8/2015 Lorio
2015/0230932 A1 8/2015 Schaller
2015/0238324 A1 8/2015 Nebosky et al.
2015/0250606 A1 9/2015 Mclean
2015/0272743 A1 10/2015 Jimenez et al.
2015/0305881 A1 10/2015 Bal et al.
2015/0320571 A1 11/2015 Lechmann et al.
2016/0000577 A1 1/2016 DiMauro
2016/0016309 A1 1/2016 Swift et al.
2016/0022437 A1 1/2016 Kelly et al.
2016/0022438 A1 1/2016 Lamborne et al.
2016/0038301 A1 2/2016 Wickham
2016/0038304 A1 2/2016 Aquino et al.
2016/0045333 A1 2/2016 Baynham
2016/0051373 A1 2/2016 Faulhaber
2016/0051374 A1 2/2016 Faulhaber
2016/0051376 A1 2/2016 Serhan et al.
2016/0058573 A1 3/2016 DiMauro et al.
2016/0067055 A1 3/2016 Hawkins et al.
2016/0074170 A1 3/2016 Rogers et al.
2016/0074175 A1 3/2016 O'Neil
2016/0081814 A1 3/2016 Baynham
2016/0089247 A1 3/2016 Nichols et al.
2016/0100954 A1 4/2016 Rumi et al.
2016/0106551 A1 4/2016 Grimberg et al.
2016/0113776 A1 4/2016 Capote
2016/0120662 A1 5/2016 Schaller
2016/0128843 A1 5/2016 Tsau et al.
2016/0199195 A1 7/2016 Hauck et al.
2016/0199196 A1 7/2016 Serhan et al.
2016/0228258 A1 8/2016 Schaller et al.
2016/0235455 A1 8/2016 Wahl
2016/0242929 A1 8/2016 Voellmicke et al.
2016/0256291 A1 9/2016 Miller
2016/0296342 A1 10/2016 Woods
2016/0310296 A1 10/2016 DiMauro et al.
2016/0317313 A1 11/2016 DiMauro

(56) References Cited

U.S. PATENT DOCUMENTS

2016/0317317 A1 11/2016 Marchek et al.
2016/0317714 A1 11/2016 DiMauro et al.
2016/0331541 A1 11/2016 DiMauro et al.
2016/0331546 A1 11/2016 Lechmann et al.
2016/0331548 A1 11/2016 DiMauro et al.
2016/0338854 A1 11/2016 Serhan et al.
2016/0367265 A1 12/2016 Morgenstern Lopez
2016/0367380 A1 12/2016 DiMauro
2016/0374821 A1 12/2016 DiMauro et al.
2017/0000622 A1 1/2017 Thommen et al.
2017/0035578 A1 2/2017 DiMauro et al.
2017/0056179 A1 3/2017 Lorio
2017/0065427 A1 3/2017 Songer
2017/0071756 A1 3/2017 Slivka et al.
2017/0095341 A1 4/2017 Smith
2017/0100177 A1 4/2017 Kim
2017/0100255 A1 4/2017 Hleihil et al.
2017/0119542 A1 5/2017 Logan et al.
2017/0209284 A1 7/2017 Overes et al.
2017/0216045 A1 8/2017 Dewey et al.
2017/0216046 A1 8/2017 Greenhalgh et al.
2017/0266015 A1 9/2017 Overes et al.
2017/0290674 A1 10/2017 Olmos et al.
2017/0290675 A1 10/2017 Olmos et al.
2017/0290677 A1 10/2017 Olmos et al.
2017/0296352 A1 10/2017 Richerme et al.
2017/0304074 A1 10/2017 DiMauro et al.
2017/0367843 A1 12/2017 Eisen et al.
2017/0367844 A1 12/2017 Eisen et al.
2017/0367845 A1 12/2017 Eisen et al.
2018/0028200 A1 2/2018 O'Neil et al.
2018/0036141 A1 2/2018 Oneil et al.
2018/0055649 A1 3/2018 Kelly et al.
2018/0071111 A1 3/2018 Sharifi-Mehr et al.
2018/0078379 A1 3/2018 Serhan et al.
2018/0116811 A1 5/2018 Bernard et al.
2018/0161171 A1 6/2018 Frasier et al.
2018/0161175 A1 6/2018 Frasier et al.
2018/0193164 A1 7/2018 Shoshtaev
2018/0256360 A1 9/2018 Cain
2018/0256362 A1 9/2018 Slivka et al.
2018/0360616 A1 12/2018 Luu
2019/0008654 A1 1/2019 Thommen
2019/0021868 A1 1/2019 Ludwig et al.
2019/0083276 A1 3/2019 DiMauro
2019/0105171 A1 4/2019 Rogers et al.
2019/0117409 A1* 4/2019 Shoshtaev ..... A61F 2/447
2019/0133785 A1 5/2019 Georges
2019/0142602 A1 5/2019 Olmos et al.
2019/0269521 A1* 9/2019 Shoshtaev ..... A61F 2/4455
2019/0269522 A1 9/2019 Pavento et al.
2019/0336301 A1 11/2019 Engstrom
2019/0388238 A1 12/2019 Lechmann et al.
2020/0008950 A1 1/2020 Serhan et al.
2020/0015982 A1 1/2020 O'Neil
2020/0030114 A1 1/2020 Cain
2020/0078192 A1 3/2020 Marchek et al.
2020/0121473 A1 4/2020 Gamache et al.
2020/0129307 A1* 4/2020 Hunziker ..... A61F 2/447
2020/0129308 A1 4/2020 Suedkamp et al.
2020/0297506 A1 9/2020 Olmos et al.
2020/0375754 A1 12/2020 Cain
2020/0375755 A1 12/2020 Cain
2020/0383799 A1 12/2020 Cain
2020/0405497 A1 12/2020 Olmos et al.
2020/0405500 A1 12/2020 Cain
2021/0000160 A1 1/2021 Olmos et al.
2021/0101585 A1* 4/2021 Son ..... B60L 50/15
2021/0177619 A1 6/2021 Voellmicke et al.
2021/0186706 A1 6/2021 Spitler et al.
2021/0353427 A1 11/2021 Butler et al.
2022/0313450 A1* 10/2022 Donohoe ..... A61F 2/447
2022/0401225 A1* 12/2022 Miller ..... A61F 2/4611
2022/0409395 A1* 12/2022 Hunziker ..... A61F 2/4611
2023/0019591 A1* 1/2023 Rogers ..... A61F 2/4611
2023/0026598 A1* 1/2023 Weiman ..... A61F 2/4455

FOREIGN PATENT DOCUMENTS

CA 2617872 A1 2/2007
CN 1177918 A 4/1998
CN 1383790 A 12/2002
CN 1819805 A 8/2006
CN 101031260 A 9/2007
CN 101087566 A 12/2007
CN 101185594 A 5/2008
CN 101631516 A 1/2010
CN 101909548 A 12/2010
CN 101951847 A 1/2011
CN 102164552 A 8/2011
CN 103620249 A 3/2014
CN 104023674 A 9/2014
CN 104023675 A 9/2014
CN 104042366 A 9/2014
CN 104822332 A 8/2015
CN 104921848 A 9/2015
CN 104939876 A 9/2015
CN 105025846 A 11/2015
CN 105188582 A 12/2015
CN 204971722 U 1/2016
CN 105769391 A 7/2016
CN 105769392 A 7/2016
CN 107205829 A 9/2017
DE 2804936 8/1979
DE 2804936 A1 8/1979
DE 3023353 A1 4/1981
DE 3801459 A1 8/1989
DE 3911610 10/1990
DE 3911610 A1 10/1990
DE 4012622 C1 7/1991
DE 9407806 U1 7/1994
DE 4012622 7/1997
DE 19710392 C1 7/1999
DE 19832798 C1 11/1999
DE 20101793 U1 5/2001
DE 202006005868 U1 6/2006
DE 202008001079 3/2008
DE 202008001079 U1 3/2008
DE 10357960 B4 9/2015
EP 0077159 A1 4/1983
EP 0260044 A1 3/1988
EP 0270704 A1 6/1988
EP 282161 9/1988
EP 0282161 A1 9/1988
EP 0433717 A1 6/1991
EP 0509084 A1 10/1992
EP 0525352 A1 2/1993
EP 0529275 A2 3/1993
EP 0609084 A2 8/1994
EP 0611557 A2 8/1994
EP 0621020 A1 10/1994
EP 0625336 A2 11/1994
EP 678489 10/1995
EP 0678489 A1 10/1995
EP 0743045 A2 11/1996
EP 0853929 A2 7/1998
EP 1046376 A1 10/2000
EP 1121906 A2 8/2001
EP 1157676 A1 11/2001
EP 1283026 A2 2/2003
EP 1290985 3/2003
EP 1290985 A2 3/2003
EP 1308132 A2 5/2003
EP 1374784 A1 1/2004
EP 1378205 A1 1/2004
EP 1405602 A1 4/2004
EP 1532949 5/2005
EP 1532949 A1 5/2005
EP 1541096 6/2005
EP 1541096 A1 6/2005
EP 1605836 A1 12/2005
EP 1385449 B1 7/2006

(56) References Cited

FOREIGN PATENT DOCUMENTS

| | | | |
|---|---|---|---|
| EP | 1683593 | | 7/2006 |
| EP | 1683593 | A2 | 7/2006 |
| EP | 1698305 | A1 | 9/2006 |
| EP | 1698305 | B1 | 8/2007 |
| EP | 1829486 | A1 | 9/2007 |
| EP | 1843723 | A1 | 10/2007 |
| EP | 1845874 | A1 | 10/2007 |
| EP | 1924227 | A2 | 5/2008 |
| EP | 1925272 | | 5/2008 |
| EP | 2156812 | A1 | 2/2010 |
| EP | 1843723 | | 3/2010 |
| EP | 2331023 | A2 | 6/2011 |
| EP | 2368529 | | 9/2011 |
| EP | 2368529 | A1 | 9/2011 |
| EP | 2237748 | B1 | 9/2012 |
| EP | 2641571 | A1 | 9/2013 |
| EP | 2705809 | A1 | 3/2014 |
| EP | 2764851 | | 8/2014 |
| EP | 2764851 | A1 | 8/2014 |
| EP | 2645965 | B1 | 8/2016 |
| EP | 3366263 | A1 | 8/2018 |
| ES | 2361099 | A1 | 6/2011 |
| FR | 2634260 | A1 | 1/1990 |
| FR | 2649311 | A1 | 1/1991 |
| FR | 2699065 | A1 | 6/1994 |
| FR | 2712486 | A1 | 5/1995 |
| FR | 2718635 | | 10/1995 |
| FR | 2718635 | A1 | 10/1995 |
| FR | 2728778 | A1 | 7/1996 |
| FR | 2730159 | | 8/1996 |
| FR | 2730159 | A1 | 8/1996 |
| FR | 2745709 | A1 | 9/1997 |
| FR | 2800601 | A1 | 5/2001 |
| FR | 2801189 | A1 | 5/2001 |
| FR | 2808182 | A1 | 11/2001 |
| FR | 2874814 | | 3/2006 |
| FR | 2874814 | A1 | 3/2006 |
| FR | 2913331 | A1 | 9/2008 |
| FR | 2948277 | | 1/2011 |
| FR | 3026294 | | 4/2016 |
| GB | 2157788 | A | 10/1985 |
| GB | 2173565 | A | 10/1986 |
| JP | 64-052439 | A | 2/1989 |
| JP | 06-500039 | A | 1/1994 |
| JP | 06-319742 | A | 11/1994 |
| JP | 07-502419 | A | 3/1995 |
| JP | 07-184922 | A | 7/1995 |
| JP | 07-213533 | A | 8/1995 |
| JP | 10-085232 | A | 4/1998 |
| JP | 11-089854 | A | 4/1999 |
| JP | 2003-010197 | A | 1/2003 |
| JP | 2003-126266 | A | 5/2003 |
| JP | 2003-526457 | | 9/2003 |
| JP | 2003-526457 | A | 9/2003 |
| JP | 2005-524472 | A | 8/2005 |
| JP | 2006-501901 | A | 1/2006 |
| JP | 2006-516456 | | 7/2006 |
| JP | 2007-054666 | A | 3/2007 |
| JP | 2007-530243 | A | 11/2007 |
| JP | 2008-507363 | A | 3/2008 |
| JP | 2008-514362 | A | 5/2008 |
| JP | 2008-126085 | A | 6/2008 |
| JP | 2011-509766 | A | 3/2011 |
| JP | 2011-520580 | A | 7/2011 |
| JP | 2012-020153 | A | 2/2012 |
| JP | 2012-508048 | A | 4/2012 |
| JP | 4988203 | B2 | 8/2012 |
| JP | 2013-508031 | | 3/2013 |
| JP | 5164571 | B2 | 3/2013 |
| JP | 2013-516206 | A | 5/2013 |
| JP | 2014-502867 | A | 2/2014 |
| JP | 2015-500707 | A | 1/2015 |
| JP | 2015-525652 | A | 9/2015 |
| JP | 2017-505196 | A | 2/2017 |
| KR | 20-0290058 | Y1 | 9/2002 |
| WO | 91/09572 | A1 | 7/1991 |
| WO | 92/04423 | A2 | 3/1992 |
| WO | 92/07594 | A1 | 5/1992 |
| WO | 92/14423 | A1 | 9/1992 |
| WO | 93/04634 | A1 | 3/1993 |
| WO | 93/04652 | A1 | 3/1993 |
| WO | 93/17669 | A1 | 9/1993 |
| WO | 94/04100 | A1 | 3/1994 |
| WO | WO 94/04100 | | 3/1994 |
| WO | 95/31158 | | 11/1995 |
| WO | WO 95/31158 | | 11/1995 |
| WO | 96/28100 | A1 | 9/1996 |
| WO | 97/00054 | A1 | 1/1997 |
| WO | WO 97/00054 | | 1/1997 |
| WO | 97/26847 | A1 | 7/1997 |
| WO | 98/34552 | A1 | 8/1998 |
| WO | 98/34568 | A1 | 8/1998 |
| WO | 99/02214 | A1 | 1/1999 |
| WO | 99/26562 | A1 | 6/1999 |
| WO | 99/42062 | A1 | 8/1999 |
| WO | 99/52478 | A1 | 10/1999 |
| WO | 99/53871 | A1 | 10/1999 |
| WO | WO 99/53871 | | 10/1999 |
| WO | 99/60956 | A1 | 12/1999 |
| WO | 99/62417 | A1 | 12/1999 |
| WO | 99/63914 | A1 | 12/1999 |
| WO | 00/12033 | | 3/2000 |
| WO | 00/13620 | A1 | 3/2000 |
| WO | WO 00/12033 | | 3/2000 |
| WO | 00/24343 | A1 | 5/2000 |
| WO | 00/67652 | | 5/2000 |
| WO | 00/44288 | A1 | 8/2000 |
| WO | 00/53127 | A1 | 9/2000 |
| WO | WO 00/53127 | | 9/2000 |
| WO | 00/67650 | A1 | 11/2000 |
| WO | 00/67651 | A1 | 11/2000 |
| WO | 00/74605 | A1 | 12/2000 |
| WO | 00/76409 | A1 | 12/2000 |
| WO | WO 00/74605 | | 12/2000 |
| WO | 01/01893 | A1 | 1/2001 |
| WO | 01/01895 | A1 | 1/2001 |
| WO | WO 01/01893 | | 1/2001 |
| WO | WO 01/01895 | | 1/2001 |
| WO | 01/10316 | A1 | 2/2001 |
| WO | 01/12054 | A2 | 2/2001 |
| WO | 01/17464 | A1 | 3/2001 |
| WO | WO 01/17464 | | 3/2001 |
| WO | 01/80751 | A1 | 11/2001 |
| WO | 01/95838 | A1 | 12/2001 |
| WO | 02/03870 | A1 | 1/2002 |
| WO | 02/17824 | A2 | 3/2002 |
| WO | 02/17825 | A2 | 3/2002 |
| WO | 02/30338 | A1 | 4/2002 |
| WO | 02/43601 | A2 | 6/2002 |
| WO | 02/43628 | A1 | 6/2002 |
| WO | 02/45627 | A1 | 6/2002 |
| WO | 02/47563 | A1 | 6/2002 |
| WO | 02/71921 | A2 | 9/2002 |
| WO | 02/85250 | A2 | 10/2002 |
| WO | 03/02021 | A2 | 1/2003 |
| WO | 03/05937 | A1 | 1/2003 |
| WO | 03/07854 | A1 | 1/2003 |
| WO | 03/20169 | A2 | 3/2003 |
| WO | 03/21308 | A2 | 3/2003 |
| WO | 03/22165 | A1 | 3/2003 |
| WO | 03/28587 | A2 | 4/2003 |
| WO | 03/43488 | A2 | 5/2003 |
| WO | 03/03951 | A1 | 6/2003 |
| WO | 2003/101308 | A1 | 12/2003 |
| WO | 2004/008949 | A2 | 1/2004 |
| WO | 03/59180 | A2 | 3/2004 |
| WO | 2004/030582 | A2 | 4/2004 |
| WO | 2004/034924 | A2 | 4/2004 |
| WO | 2004/062505 | A1 | 7/2004 |
| WO | 2004/064603 | A2 | 8/2004 |
| WO | 2004/069033 | A2 | 8/2004 |
| WO | 2004/073563 | A2 | 9/2004 |
| WO | 2004/078220 | A2 | 9/2004 |
| WO | 2004/078221 | A2 | 9/2004 |

(56) References Cited

FOREIGN PATENT DOCUMENTS

| | | | |
|---|---|---|---|
| WO | 2004/080316 | A1 | 9/2004 |
| WO | 2004/082526 | A2 | 9/2004 |
| WO | 2004/098420 | A2 | 11/2004 |
| WO | 2004/098453 | A2 | 11/2004 |
| WO | 2004/108022 | A1 | 12/2004 |
| WO | 2005/027734 | A2 | 3/2005 |
| WO | 2005/032433 | A2 | 4/2005 |
| WO | 2005/039455 | A1 | 5/2005 |
| WO | 2005/051246 | A2 | 6/2005 |
| WO | 2005/081877 | A2 | 9/2005 |
| WO | 2005/094297 | A2 | 10/2005 |
| WO | 2005/112834 | A2 | 12/2005 |
| WO | 2005/112835 | A2 | 12/2005 |
| WO | 2005/115261 | A1 | 12/2005 |
| WO | WO 2005/112834 | | 12/2005 |
| WO | 2006/017507 | A2 | 2/2006 |
| WO | 2006/044920 | A2 | 4/2006 |
| WO | 2006/047587 | A2 | 5/2006 |
| WO | 2006/047645 | A2 | 5/2006 |
| WO | WO 2006/047587 | | 5/2006 |
| WO | 2006/058079 | A2 | 6/2006 |
| WO | 2006/058281 | A2 | 6/2006 |
| WO | 2006/060420 | A1 | 6/2006 |
| WO | 2006/063083 | A1 | 6/2006 |
| WO | 2006/065419 | A2 | 6/2006 |
| WO | 2006/066228 | A2 | 6/2006 |
| WO | WO 2006/058281 | | 6/2006 |
| WO | WO 2006/065419 | | 6/2006 |
| WO | 2006/072941 | A2 | 7/2006 |
| WO | 2006/078972 | A2 | 7/2006 |
| WO | 2006/081843 | A1 | 8/2006 |
| WO | WO 2006/081843 | | 8/2006 |
| WO | 2006/108067 | A2 | 10/2006 |
| WO | 2006/118944 | A1 | 11/2006 |
| WO | 2007/009107 | A2 | 1/2007 |
| WO | WO 2007/009107 | | 1/2007 |
| WO | 2007/022194 | A2 | 2/2007 |
| WO | 2007/028098 | A2 | 3/2007 |
| WO | WO 2007/028098 | | 3/2007 |
| WO | 2007/048012 | A2 | 4/2007 |
| WO | WO 2007/048012 | | 4/2007 |
| WO | 2007/067726 | A2 | 6/2007 |
| WO | 2007/084427 | A2 | 7/2007 |
| WO | 2007/119212 | A2 | 10/2007 |
| WO | 2007/124130 | A2 | 11/2007 |
| WO | 2008/005627 | A2 | 1/2008 |
| WO | 2008/011378 | A1 | 1/2008 |
| WO | 2008/044057 | A1 | 4/2008 |
| WO | WO 2008/044057 | | 4/2008 |
| WO | 2008/064842 | A2 | 6/2008 |
| WO | 2008/070863 | A2 | 6/2008 |
| WO | 2008/103781 | A2 | 8/2008 |
| WO | 2008/103832 | A2 | 8/2008 |
| WO | 2009/064787 | A2 | 5/2009 |
| WO | WO 2009/064787 | | 5/2009 |
| WO | 2009/092102 | A1 | 7/2009 |
| WO | WO 2009/092102 | | 7/2009 |
| WO | 2009/124269 | A1 | 10/2009 |
| WO | WO 2009/124269 | | 10/2009 |
| WO | 2009/143496 | A1 | 11/2009 |
| WO | WO 2009/143496 | | 11/2009 |
| WO | 2009/147527 | A2 | 12/2009 |
| WO | 2009/152919 | A1 | 12/2009 |
| WO | 2010/011348 | A1 | 1/2010 |
| WO | 2010/054181 | A1 | 5/2010 |
| WO | 2010/068725 | A2 | 6/2010 |
| WO | WO 2010/068725 | | 6/2010 |
| WO | 2010/075451 | A1 | 7/2010 |
| WO | 2010/075555 | A2 | 7/2010 |
| WO | 2010/088766 | A1 | 8/2010 |
| WO | 2010/121002 | A1 | 10/2010 |
| WO | 2010/125514 | A1 | 11/2010 |
| WO | 2010/136170 | A1 | 12/2010 |
| WO | 2010/148112 | A1 | 12/2010 |
| WO | WO 2010/148112 | | 12/2010 |
| WO | 2011/013047 | A2 | 2/2011 |
| WO | 2011/046459 | A1 | 4/2011 |
| WO | 2011/046460 | A1 | 4/2011 |
| WO | 2011/060087 | A1 | 5/2011 |
| WO | 2011/079910 | A2 | 7/2011 |
| WO | 2011/119617 | A1 | 9/2011 |
| WO | 2011/142761 | A1 | 11/2011 |
| WO | WO 2011/142761 | | 11/2011 |
| WO | 2011/150350 | A1 | 12/2011 |
| WO | 2012/009152 | A1 | 1/2012 |
| WO | WO 2012/009152 | | 1/2012 |
| WO | 2012/027490 | A2 | 3/2012 |
| WO | 2012/028182 | A1 | 3/2012 |
| WO | 2012/030331 | A1 | 3/2012 |
| WO | 2012/089317 | A1 | 7/2012 |
| WO | WO 2012/089317 | | 7/2012 |
| WO | 2012/103254 | A2 | 8/2012 |
| WO | 2012/122294 | A1 | 9/2012 |
| WO | 2012/129197 | A1 | 9/2012 |
| WO | 2012/135764 | A1 | 10/2012 |
| WO | WO 2012/135764 | | 10/2012 |
| WO | 2013/006669 | A2 | 1/2013 |
| WO | WO 2013/006669 | | 1/2013 |
| WO | 2013/023096 | A1 | 2/2013 |
| WO | 2013/025876 | A1 | 2/2013 |
| WO | WO 2013/023096 | | 2/2013 |
| WO | WO 2013/025876 | | 2/2013 |
| WO | 2013/043850 | A2 | 3/2013 |
| WO | 2013/062903 | A1 | 5/2013 |
| WO | WO 2013/043850 | | 5/2013 |
| WO | WO 2013/062903 | | 5/2013 |
| WO | 2013/082184 | A1 | 6/2013 |
| WO | WO 2013/082184 | | 6/2013 |
| WO | 2013/148176 | A1 | 10/2013 |
| WO | 2013/149611 | A1 | 10/2013 |
| WO | 2013/158294 | A1 | 10/2013 |
| WO | WO 2013/158294 | | 10/2013 |
| WO | 2013/173767 | A1 | 11/2013 |
| WO | WO 2013/173767 | | 11/2013 |
| WO | 2013/184946 | A1 | 12/2013 |
| WO | WO 2013/184946 | | 12/2013 |
| WO | 2014/014610 | A1 | 1/2014 |
| WO | 2014/018098 | A1 | 1/2014 |
| WO | WO 2014/018098 | | 1/2014 |
| WO | 2014/026007 | A1 | 2/2014 |
| WO | WO 2014/026007 | | 2/2014 |
| WO | 2014/035962 | A1 | 3/2014 |
| WO | WO 2014/035962 | | 3/2014 |
| WO | 2014/088521 | A2 | 6/2014 |
| WO | WO 2014/088521 | | 6/2014 |
| WO | 2014/116891 | A1 | 7/2014 |
| WO | WO 2014/116891 | | 7/2014 |
| WO | 2014/144696 | A1 | 9/2014 |
| WO | 2015/004660 | A1 | 1/2015 |
| WO | 2015/013479 | A2 | 1/2015 |
| WO | 2015/022039 | A1 | 2/2015 |
| WO | 2015/048997 | A1 | 4/2015 |
| WO | 2016/069796 | A1 | 5/2016 |
| WO | 2016/118246 | A1 | 7/2016 |
| WO | 2016/127139 | A1 | 8/2016 |
| WO | 2017/040881 | A1 | 3/2017 |
| WO | 2017/136620 | A1 | 8/2017 |
| WO | 2018/078148 | A1 | 5/2018 |

OTHER PUBLICATIONS

Brochure for PERPOS PLS System Surgical Technique by Interventional Spine, 2008, 8 pages.

Brooks et al., "Efficacy of Supplemental Posterior Transfacet Pedicle Device Fixation in the Setting of One- or Two-Level Anterior Lumbar Interbody Fusion", Retrieved Jun. 19, 2017, 6 pages.

Chiang, "Biomechanical Comparison of Instrumented Posterior Lumbar Interbody Fusion with One or Two Cages by Finite Element Analysis", Spine, Sep. 2006, pp. E682-E689, vol. 31(19), Lippincott Williams & Wilkins, Inc.

Chin, "Early Results of the Triage Medical Percutaneous Transfacet Pedicular Bone-Lok Compression Device for Lumbar Fusion", Accessed online Jul. 10, 2017, 10 pages.

(56) References Cited

OTHER PUBLICATIONS

Fuchs, "The use of an interspinous implant in conjuction with a graded facetectomy procedure", Spine vol. 30, No. 11, pp. 1266-1272, 2005.
Gore, "Technique of Cervical Interbody Fusion", Clinical Orthopaedics and Related Research, Sep. 1984, pp. 191-195, No. 188.
Gray's Anatomy, Crown Publishers, Inc., 1977, pp. 33-54.
Hoogland et al., "Total Lumar Intervertebral Disc Replacement: Testing a New Articulating Space in Human Cadaver Spines—24 1", Annual ORS, Dallas, TX, Feb. 21-23, 1978, 8 pages.
Hunt, "Expandable Cage Placement Via a Posterolateral Approach in Lumbar Spine Reconstructions", Journal of Neurosurgery: Spine, Sep. 2006, pp. 271-274, vol. 5.
Iprenburg et al., "Transforaminal Endocopic Surgery in Lumbar Disc Hermiation in an Economic crises—The Tessys Method", US Musculoskeletal, 2008, pp. 47-49.
King., "Internal Fixation for Lumbosacral Fusion", The Journal of Bone and Joint Surgery, J. Bone Joint Surg. Am., 1948; 30: 560-578.
Krbec, "Replacement of the Vertebral Body with an Expansion Implant (Synex)", Acta Chir Orthop Traumatol Cech, 2002, pp. 158-162, vol. 69(3).
Mahar et al., "Biomechanical Comparison of Novel Percutaneous Transfacet Device and a Traditional Posterior System for Single Level Fusion", Journal of Spinal Disorders & Techniques, Dec. 2006, vol. 19, No. 8, pp. 591-594.
Medco Forum, "Percutaneous Lumbar Fixation Via PERPOS PLS System Interventional Spine", Sep. 2008, vol. 15, No. 37.
Medco Forum, "Percutaneous Lumbar Fixation via PERPOS System From Interventional Spine", Oct. 2007, vol. 14, No. 49.
Morgenstern, "Transforaminal Endoscopic Stenosis Surgery—A Comparative Study of Laser and Reamed Foraminoplasty", in European Musculoskeletal Review, Issue 1, 2009.
Niosi, "Biomechanical Characterization of the three-dimentional kinematic behavior of the dynesys dynamic stabilization system: an in vitro study", Eur Spine J. (2006), 15: pp. 913-922.
ProMap TM EMG Navigation Probe. Technical Brochure Spineology Inc, Dated May 2009.
Shin, "Posterior Lumbar Interbody Fusion via a Unilateral Approach", Yonsei Medical Journal, 2006, pp. 319-325, vol. 47(3).
Siddiqui, "The Positional Magnetic Resonance Imaging Changes in the Lumbar Spine Following Insertion of a Novel Interspinous Process Distraction Device", Spine, vol. 30, No. 23, pp. 2677-2682, 2005.
Talwar "Insertion loads of the X Stop interspinous process distraction system designed to treat neurogenic intermittent claudication", Eur Spine J. (2006) 15: pp. 908-912.
U.S. Appl. No. 60/424,055, filed Nov. 5, 2002, entitled Method and apparatus for spinal fixation.
U.S. Appl. No. 60/397,588, Method and apparatus for spinal fixation, filed Jul. 19, 2002.
U.S. Appl. No. 61/675,975, Expandable Implant, filed Jul. 26, 2012.
U.S. Appl. No. 60/942,998, Method and Apparatus for Spinal Stabilization, filed Jun. 8, 2007.
U.S. Appl. No. 14/640,220, filed Mar. 6, 2015, entitled Expandable Intervertebral Implant.
U.S. Appl. No. 14/685,358, filed Apr. 13, 2015, entitled Expandable Intervertebral Implant.
U.S. Appl. No. 14/685,402, filed Apr. 13, 2015, entitled Expandable Intervertebral Implant.
U.S. Appl. No. 14/790,866, filed Jul. 2, 2015, entitled Expandable Implant.
U.S. Appl. No. 60/794,171, filed Apr. 21, 2006, entitled Method and Apparatus for Spinal Fixation.
Zucherman, "A Multicenter, Prospective, Randomized Trial Evaluating the X Stop Interspinous Process Decompression System for the Treatment of Neurogenic Intermittent Claudication", Spine, vol. 30, No. 12, pp. 1351-1358, 2005.
International Patent Application No. PCT/US2013/029014, International Search Report dated Jul. 1, 2013, 2 pages.
Bruder et al., Identification and characterization of a cell surface differentiation antigen on human osteoprogenitor cells. 42nd Annual Meeting of the Orthopaedic Research Society. p. 574, Feb. 19-22, 1996, Atlanta, Georgia.
Bruder et al., Monoclonal antibodies reactive with human osteogenic cell surface antigens. Bone. Sep. 1997;21 (3):225-235.
Burkoth et al., A review of photocrosslinked polyanhydrides: in situ forming degradable networks. Biomaterials. Dec. 2000; 21 (23): 2395-2404.
Cambridge Scientific News, FDA Approves Cambridge Scientific, Inc.'s Orthopedic Wisorb (TM) Malleolar Screw [online], Jul. 30, 2002 [retrieved on Oct. 14, 2003]. Retrieved from the Internet <URL: http://www.cambridgescientificinc.com>.
Carrino, John A., Roxanne Chan and Alexander R. Vaccaro, "Vertebral Augmentation: Vertebroplasty and Kyphoplasty", Seminars in Roentgenology, vol. 39, No. 1 Jan. 2004: pp. 68-84.
Cheng, B.C., Ph.D., Biomechanical pullout strength and histology of Plasmapore Registered XP coated implants: Ovine multi time point survival study. Aesculap Implant Systems, LLC, 2013, 12 pages.
Edeland, H.G., "Some Additional Suggestions For An Intervertebral Disc Prosthesis", J of Bio Medical Engr., vol. 7(1) pp. 57-62, Jan. 1985.
European Search Report EP03253921 dated Nov. 13, 2003, 4 pages.
Flemming et al., Monoclonal anitbody against adult marrow-derived mesenchymal stem cells recognizes developing vasculature in embryonic human skin. Developmental Dynamics. 1998;212:119-132.
Gennaro, A.R., ed., Remington: The Science and Practice of Pharmacy. Williams & Wilkins, 19th edition, Jun. 1995.
Ha et al. (Topographical characterization and microstructural interface analysis of vacuum-plasma-sprayed titanium and hydroxyapatite coatings on carbon fiber-reinforced poly(etheretherketone), Journal of Materials Science: Materials in Science 9 (1997), pp. 891-896.
Haas, Norbert P., New Products from AO Development [online], May 2002 [retrieved on Oct. 14, 2003]. Retrieved from the Internet <URL: http://www.ao.asif.ch/development/pdf_tk_news_02.pdf>.
Hao et al., Investigation of nanocomposites based on semi-interpenetrating network of [L-poly (epsilon-caprolactone)]/[net-poly (epsilon-caprolactone)] and hydroxyapatite nanocrystals. Biomaterials. Apr. 2003;24(9): 1531-9.
Harsha et al., Tribo performance of polyaryletherketone composites, Polymer Testing (21) (2002) pp. 697-709.
Haynesworth et al., Cell surface antigens on human marrow-derived mesenchymal cells are detected by monoclonal antibodies. Bone. 1992;13(1):69-80.
Hitchon et al., Comparison of the biomechanics of hydroxyapatite and polymethylmethacrylate vertebroplasty in a cadaveric spinal compression fracture model. J Neurosurg. Oct. 2001;95(2 Suppl):215-20.
Joshi, Ajeya P., M.D. and Paul A. Glazer, M.D., "Vertebroplasty: Current Concepts and Outlook for the Future", 2003, (5 pages), From: http://www.orthojournalhms.org/html/pdfs/manuscript-15.pdf.
Kandziora, Frank, et al., "Biomechanical Analysis of Biodegradable Interbody Fusion Cages Augmented with Poly (propylene Glycol-co-Fumaric Acid)," Spine, 27(15): 1644-1651 (2002).
Kotsias, A., Clinical trial of titanium-coated Peel cages anterior cervical discectomy and fusion. [Klinishe Untersuching zum Einsatz von titanbeschichteten Polyetheretherketon-Implantaten bei der cervikalen interkorporalen fusion]. Doctoral thesis. Department of Medicine, Charite, University of Medicine Berlin, 2014, 73 pages. (German language document/Engl. summary).
Kroschwitz et al., eds., Hydrogels. Concise Encyclopedia of Polymer Science and Engineering. Wiley and Sons, pp. 458-459, 1990.
Lendlein et al., AB-polymer networks based on oligo(epsilon-caprolactone) segments showing shape-memory properties. Proc Natl Acad Sci US A. Jan. 30, 2001;98(3):842-7. Epub Jan. 23, 2001.
Malberg. M.I., MD; Pimenta, L., MD; Millan, M.M., MD, 9th International Meeting on Advanced Spine Techniques, May 23-25, 2002, Montreux, Switzerland. Paper #54, Paper #60, and E-Poster #54, 5 pages.

(56) References Cited

OTHER PUBLICATIONS

McAfee et al., Minimally invasive anterior retroperitoneal approach to the lumbar spine: Emphasis on the lateral Bak. Spine. 1998;23(13):1476-84.
Mendez et al., Self-curing acrylic formulations containing PMMA/PCL composites: properties and antibiotic release behavior. J Biomed Mater Res. Jul. 2002;61 (1 ):66-74.
Nguyen et al., Poly(Aryl-Ether-Ether-Ketone) and its Advanced Composites: A Review, Polymer Composites, Apr. 1987, vol. 8, No. 2, pp. 57-73.
Osteoset Registered DBM Pellets (Important Medical Information) [online], Nov. 2002 [retrieved on Oct. 14, 2003]. Retrieved from the Internet <URL: http://www.wmt.com/Literature>.
Porocoat(R) Porous Coating, 1 Page, https://emea.depuysynthese.com/hcp/hip/products/qs/porocoat-porous-coatingemea Accessed on Jul. 31, 2017.
Regan et al., Endoscopic thoracic fusion cage. Atlas of Endoscopic Spine Surgery. Quality Medical Publishing, Inc. 1995;350-354.
Slivka et al., In vitro compression testing of fiber-reinforced, bioabsorbable, porous implants. Synthetic Bioabsorbable Polymers for Implants. STP1396, pp. 124-135, ATSM International, Jul. 2000.
Sonic Accelerated Fracture Healing System/Exogen 3000. Premarket Approval. U.S. Food & Drug Administration. Date believed to be May 10, 2000. Retrieved Jul. 23, 2012 from <http://www.accessdata.fda.gov/scripts/cdrh/cfdocs/cfPMA/pma.cfm?id=14736#>. 4 pages, 2012.
Stewart et al., Co-expression of the stro-1 anitgen and alkaline phosphatase in cultures of human bone and marrow cells. ASBMR 18th Annual Meeting. Bath Institute for Rheumatic Diseases, Bath, Avon, UK. Abstract No. P208, p. S142, 1996.
Timmer et al., In vitro degradation of polymeric networks of poly(propylene fumarate) and the crosslinking macromer poly(propylene fumarate)-diacrylate. Biomaterials. Feb. 2003;24(4 ):571-7.
United States Disctrict Court, Central District of California, Case No. 1 :10-CV-00849-LPS, *Nuvasive, Inc.*, vs., *Globus Medical, Inc.*, Videotaped Deposition of: Luiz Pimenta, M.D., May 9, 2012, 20 pages.
Walsh et al., Preparation of porous composite implant materials by in situ polymerization of porous apatite containing epsilon-caprolactone or methyl methacrylate. Biomaterials. Jun. 2001;22(11):1205-12.
Zimmer.com, Longer BAK/L Sterile Interbody Fusion Devices. Date believed to be 1997. Product Data Sheet.Zimmer. Retrieved Jul. 23, 2012 from <http:/ catalog.zimmer.com/contenUzpc/products/600/600/620/S20/S045. html>, 2 pages.
Allcock, "Polyphosphazenes"; The Encyclopedia of Polymer Science; 1988; pp. 31-41; vol. 13; Wiley Intersciences, John Wiley & Sons.
CN Office Action dated Apr. 24, 2020 for ON Application No. 201780040910.
Cohn, "Biodegradable PEO/PLA Block Copolymers"; Journal of Biomedical Materials Research; 1988; pp. 993-1009; vol. 22; John Wiley & Sons, Inc.
Cohn, "Polymer Preprints"; Journal of Biomaterials Research; 1989; p. 498; Biomaterials Research Labortatory, Casali Institute of Applied Chemistry, Israel.
Heller, "Poly (Otrho Esters)"; Handbook of Biodegradable Polymers; edited by Domb; et al; Hardwood Academic Press; 1997; pp. 99-118.
Japanese Office Action for Application No. 2013-542047, dated Sep. 8, 2015 (12 pages).
Japanese Office Action for Application No. 2016-135826, dated Jun. 6, 2017, (7 pages).
Kambin, et al.; Percutaneous Lateral Discectomy of the Lumbar Spine: A Preliminary Report; Clin. Orthop.; 1983; 174: 127-132.
Kemnitzer, "Degradable Polymers Derived From the Amino Acid L-Tyrosine"; 1997; pp. 251-272; edited by Domb, et al., Hardwood Academic Press.
Khoo, "Minimally Invasive Correction of Grade I and II Isthmic Spondylolisthesis using AxiaLIF for L5/S1 Fusion", pp. 1-7, Rev B Sep. 15, 2008.
Khoo, Axilif address spongy from the caudal approach. Minimally Invasive Correction of Grage I and II Isthmic Spondylolisthesis using AsiaLiF for L5/S1 Fusion, pp. 45-0123 Rev B Sep. 15, 2008.
Krbec, "Replacement of the vertebral body with an expansion implant (Synex)", Acta Chir Orthrop Traumatol Cech., 2002, pp. 158-162, vol. 69(3) (only Abstract available).
U.S. Appl. No. 61/009,546, filed Dec. 28, 2007 Rodgers.
U.S. Appl. No. 61/140,926, filed Dec. 26, 2008 Spann.
U.S. Appl. No. 61/178,315, filed May 14, 2009 Spann.
U.S. Appl. No. 09/558,057, filed Apr. 26, 2000, entitled Bone Fixation System.
Vandorpe, "Biodegradable Polyphosphazenes for Biomedical Applications"; Handbook of Biodegradable Polymers; 1997; pp. 161-182; Hardwood Academic Press.
International Patent Application No. PCT/US2013/029014, International Search Report dated Jul. 1, 2013, 7 pages.
Folman, Posterior Lumbar Interbody Fusion for Degenerative Disc Disease Using a Minimally Invasive B-Twin Expandable Spinal Spacer, Journal of Spinal Disorders & Techniques, 2003, pp. 455-460, vol. 16(5).
Polikeit, The importance of the endplate for interbody cages in the lumbar spine, Eur Spine J, 2003, pp. 556-561, vol. 12.
Spine Solutions Brochure—Prodisc 2001, 16 pages.
Link SB Charite Brochure—Intervertebral Prosthesis 1988, 29 pages.

* cited by examiner

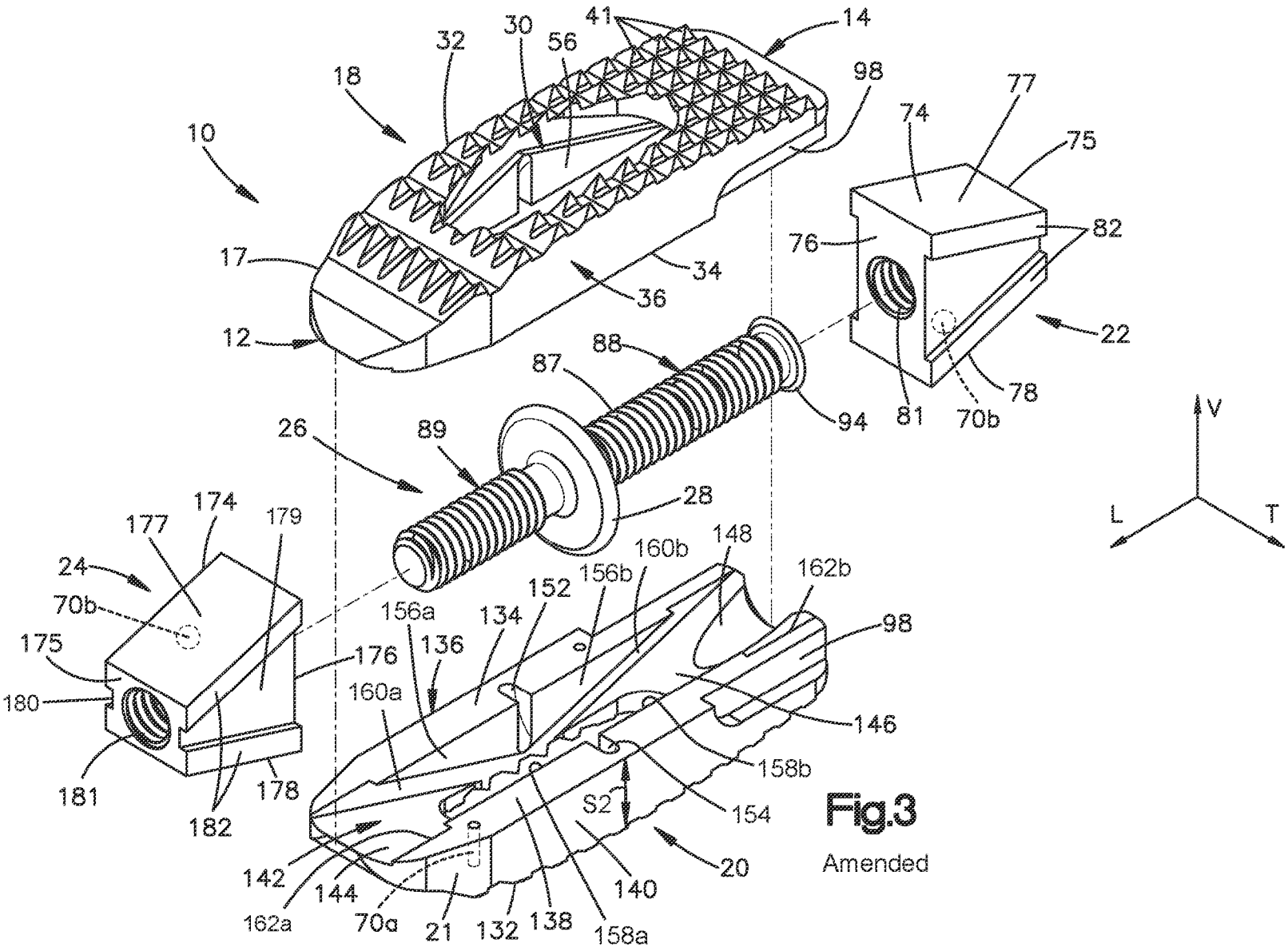
T
V
L
22
82
75
77
78
70b
74
81
76
94
98
14
34
36
41
56
30
32
18
10
17
12
88
87
28
89
26
162b
146
158b
154
148
160b
156b
152
134
136
156a
160a
176
20
S2
140
158a
138
132
21
70a
144
142
162a
179
178
182
174
177
24
70b
175
180
181
Fig.3
Amended

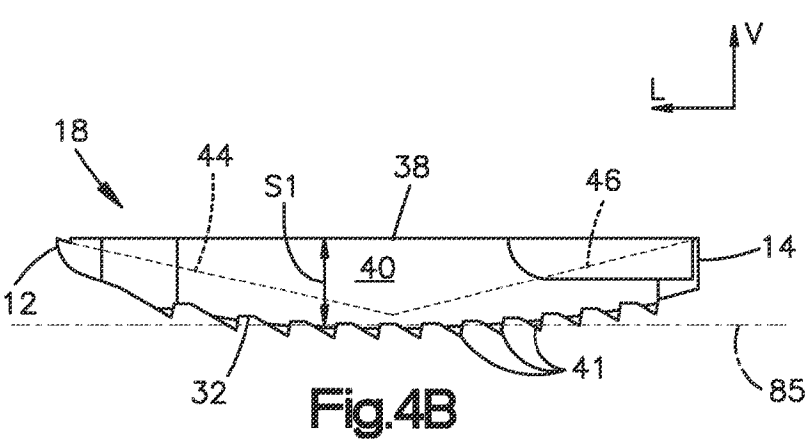
Fig.4B
Amended
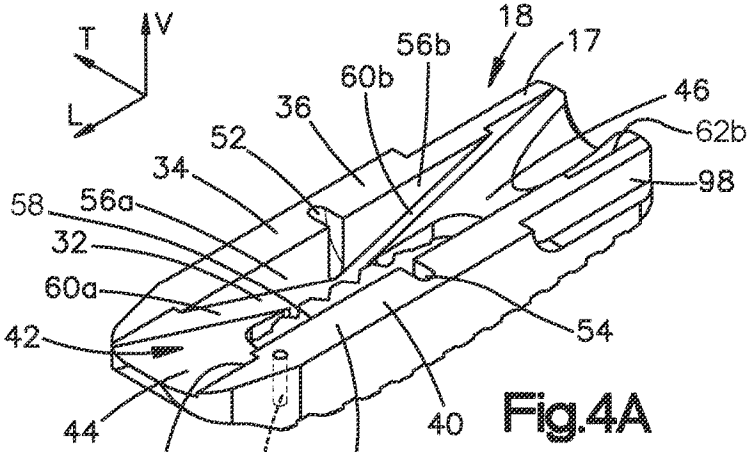
Fig.4A
Amended
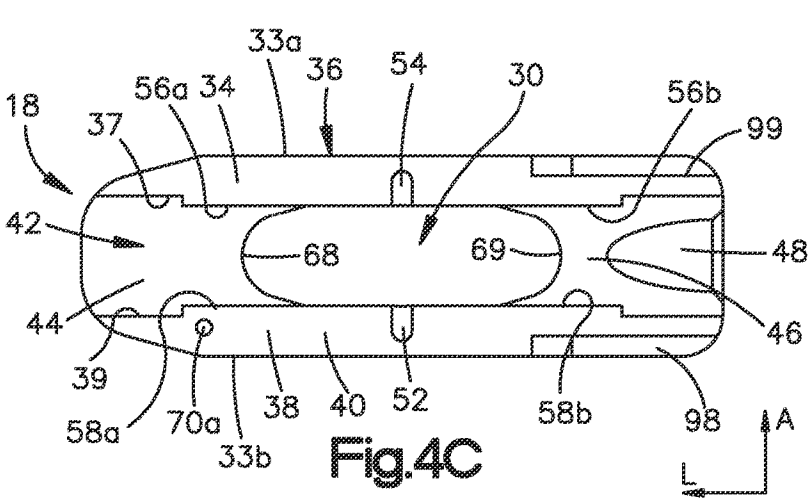
Fig.4C
Amended

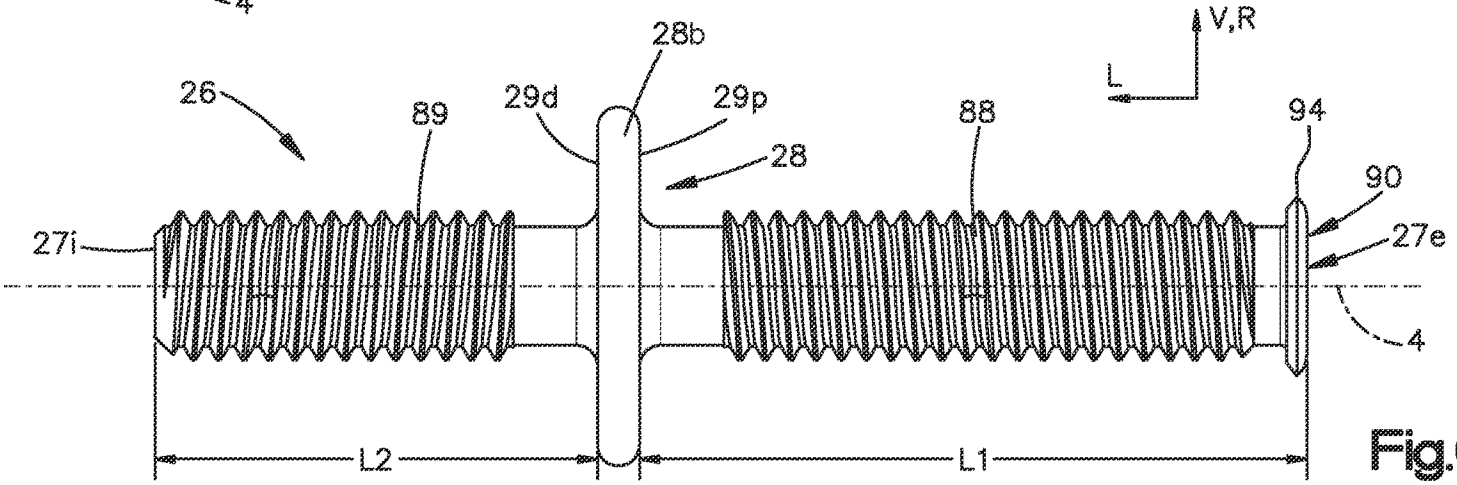
Fig.6B
Amended

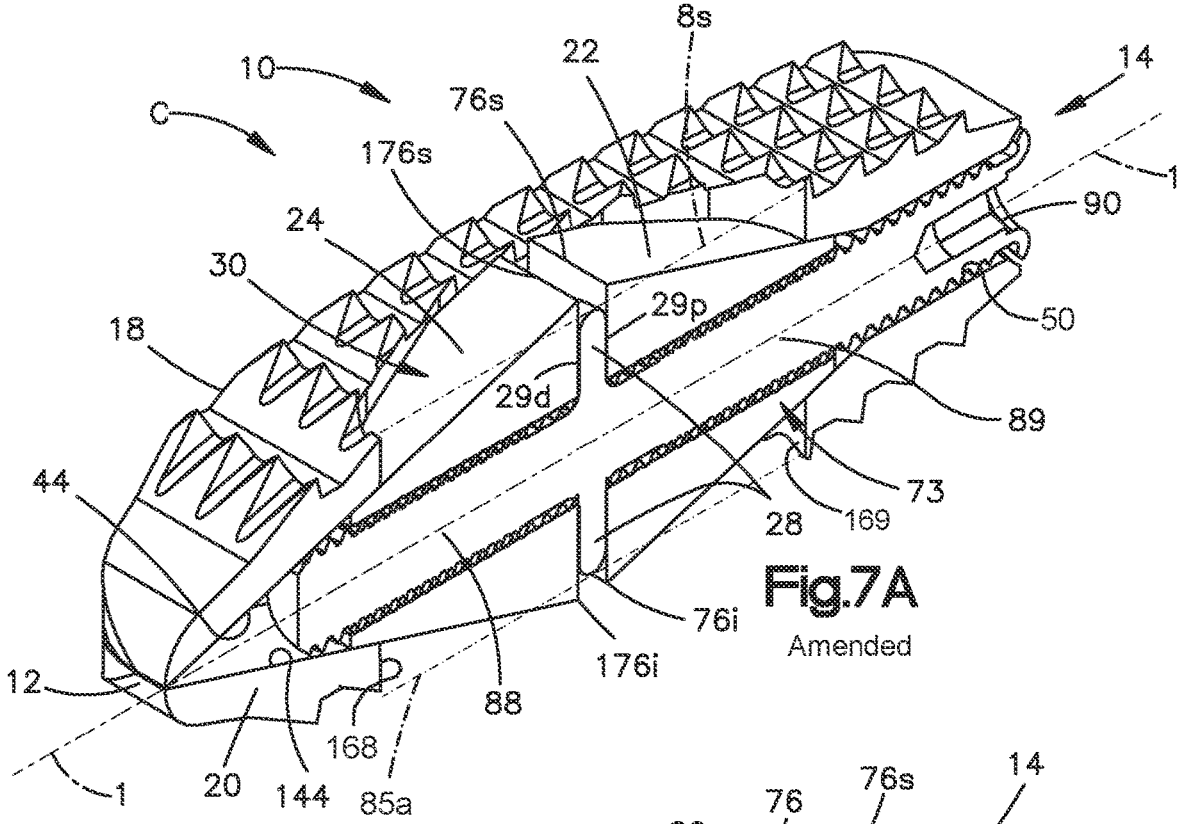
Fig.7A
Amended

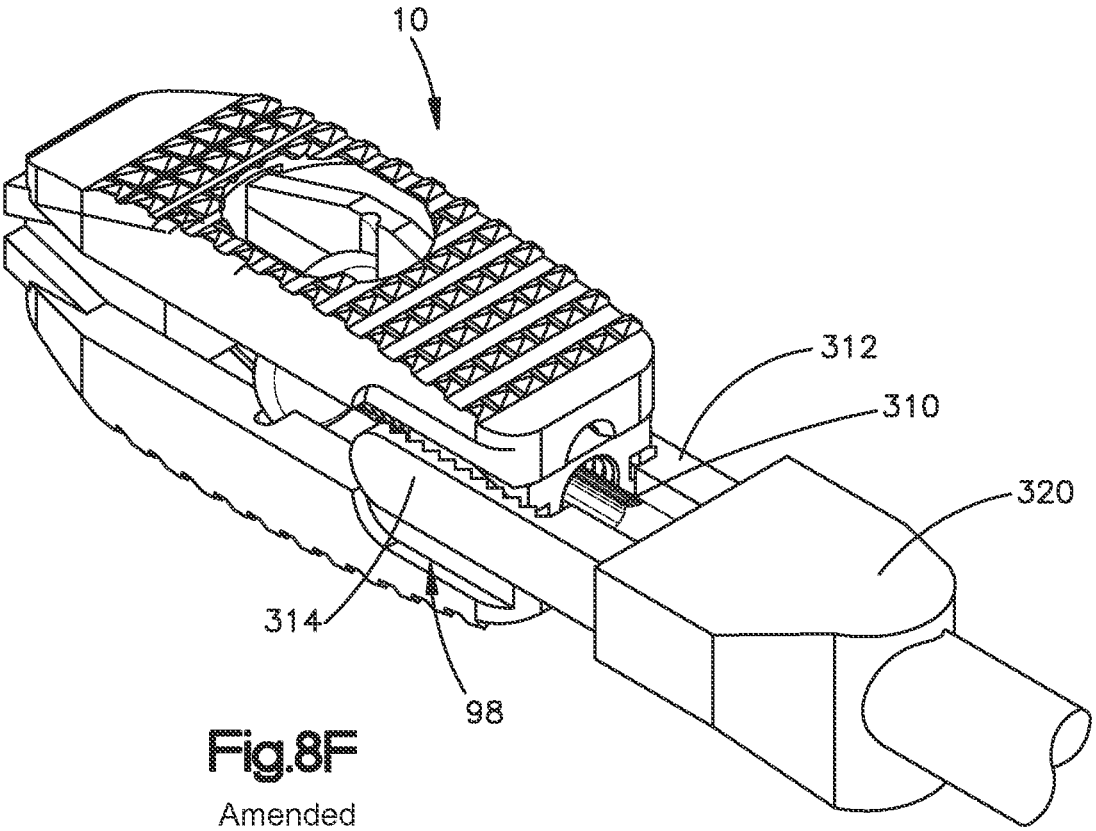
Fig.8F
Amended

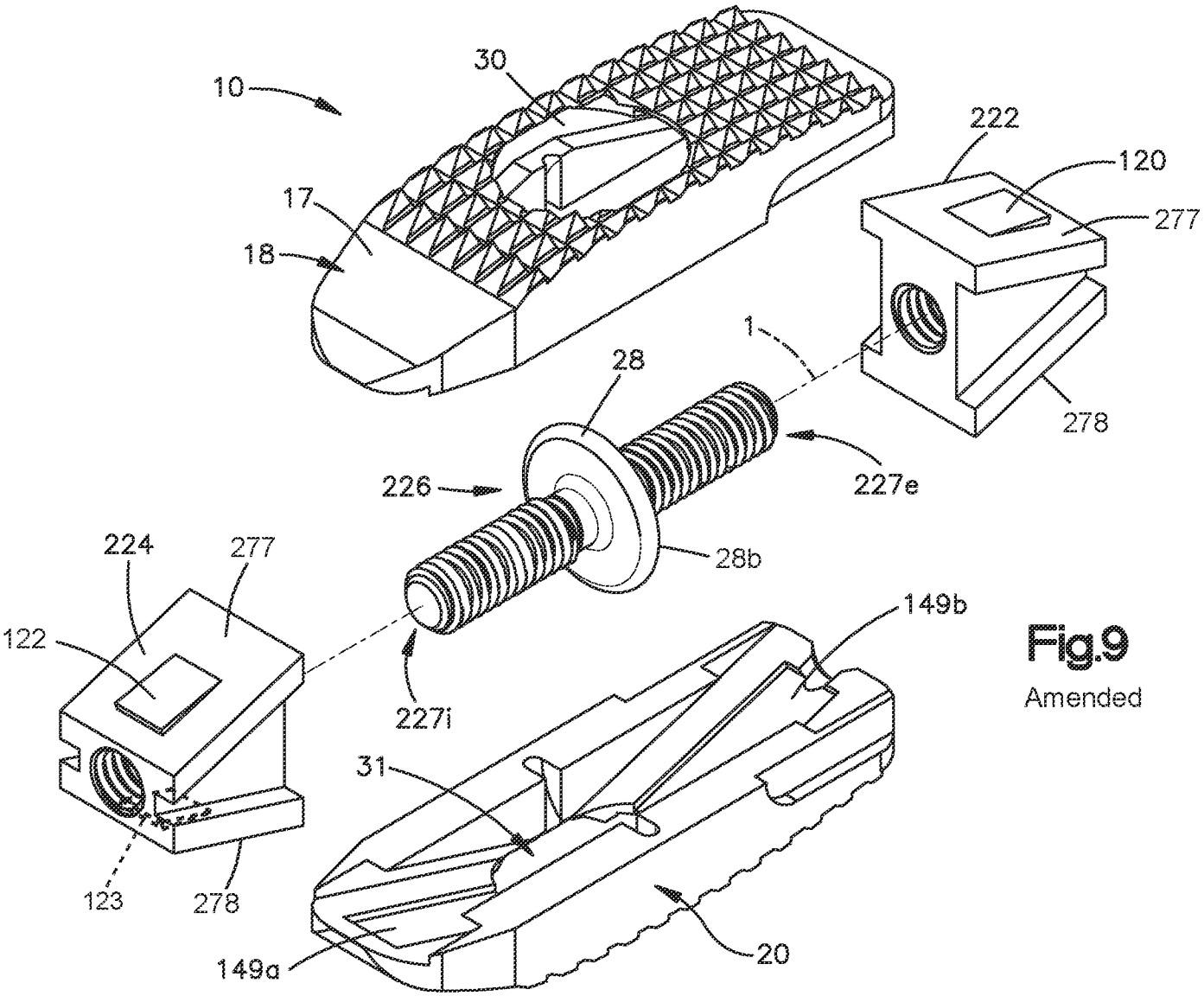
Fig.9
Amended

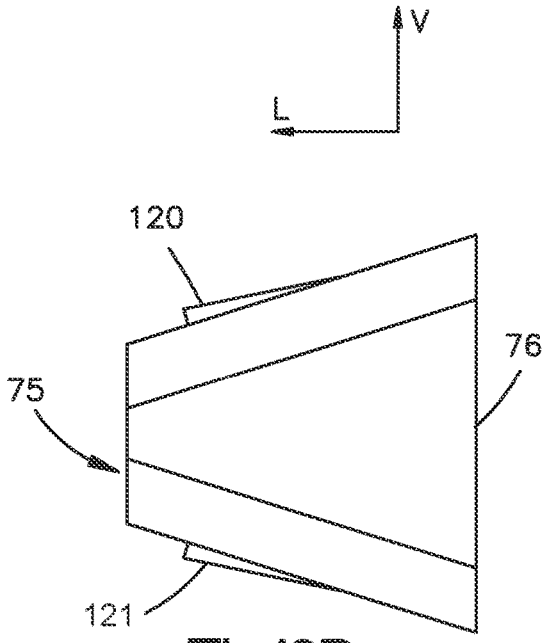
Fig.10B
Amended

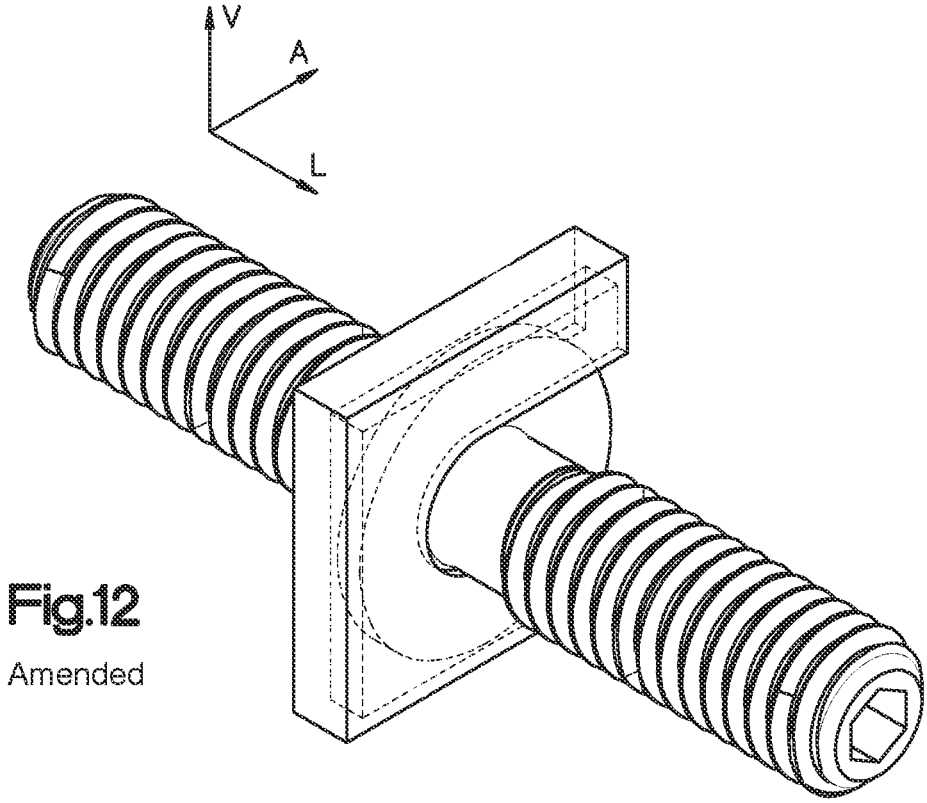
Fig.12
Amended

EXPANDABLE INTERVERTEBRAL IMPLANT, SYSTEM, KIT AND METHOD

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*CROSS-REFERENCE TO RELATED APPLICATIONS*

*This application is a reissue application of U.S. Pat. No. 9,717,601, issued Aug. 1, 2017.*

TECHNICAL FIELD

The present invention relates to an expandable intervertebral implant, system, kit and method.

BACKGROUND

Removal of an intervertebral disc is often desired if the disc degenerates. Spinal fusion may be used to treat such a condition and involves replacing a degenerative disc with a device such as a cage or other spacer that restores the height of the disc space and allows bone growth through the device to fuse the adjacent vertebrae. Spinal fusion attempts to restore normal spinal alignment, stabilize the spinal segment for proper fusion, create an optimal fusion environment, and allows for early active mobilization by minimizing damage to spinal vasculature, dura, and neural elements. When spinal fusion meets these objectives, healing quickens and patient function, comfort and mobility improve. Spacer devices that are impacted into the disc space and allow growth of bone from adjacent vertebral bodies through the upper and lower surfaces of the implant are known in the art. Yet there continues to be a need for devices that minimize procedural invasiveness yet stabilize the spinal segment and create an optimum space for spinal fusion.

SUMMARY

According to an embodiment of the present disclosure, the expandable implant configured for insertion in an intervertebral space defined between a first vertebral body and a second vertebral body. The implant defines an insertion end spaced apart from a trailing end along a longitudinal direction. The implant can include a first plate and a second plate opposed to the first plate along a vertical direction that is perpendicular to the longitudinal direction. The implant can include a first wedge member and a second wedge member spaced from the first wedge member along the longitudinal direction, the first and second wedge members coupled to the first and second plates. Each wedge member defines a narrow end spaced apart from an inner end along the longitudinal direction, and the inner ends of each wedge member face other. The first and second wedge members configured to translate along the longitudinal direction along to the first and second plates from a first contracted configuration into a second separated configuration. The implant can include an actuation member coupled to the first wedge member and the second wedge member, the actuating member defining a flange extending toward the first and second plates, the actuation member configured to move the first and second wedge members from the first contracted configuration into the second separated configuration so as to separate the first and second plates from each other along the vertical direction.

BRIEF DESCRIPTION OF THE DRAWINGS

The foregoing summary, as well as the following detailed description of illustrative embodiments of the intervertebral implant of the present application, will be better understood when read in conjunction with the appended drawings. For the purposes of illustrating the expandable intervertebral implant of the present application, there is shown in the drawings illustrative embodiments. It should be understood, however, that the application is not limited to the precise arrangements and instrumentalities shown. In the drawings:

FIG. 3 is an exploded perspective view of the implant shown in FIG. 1;

FIG. 4A is a perspective view of the interior surface of a plate of the implant shown in FIG. 1;

FIG. 4B is side view of a plate of the implant shown in FIG. 4A;

FIGS. 4C and 4D are bottom and top plan views, respectively, of a plate of the implant shown in FIG. 4A;

FIGS. 6A and 6B are perspective and side views of the actuation member used in the implant shown in FIG. 1;

FIGS. 7A and 7B are sectional views of the implant taken along lines 7-7 in FIGS. 2A and 2B, illustrating the collapsed and expanded configurations;

FIGS. 8E and 8F are partial perspective views of the tool shown in FIG. 8D supporting an implant;

FIG. 9 is an exploded perspective view an implant according to another embodiment of the present disclosure;

FIGS. 10A and 10B are perspective and side views of a wedge member of the implant shown in FIG. 9;

FIG. 12 is a perspective view of an actuation member in accordance with another embodiment of the present disclosure.

DETAILED DESCRIPTION OF ILLUSTRATIVE EMBODIMENTS

Figure 1:
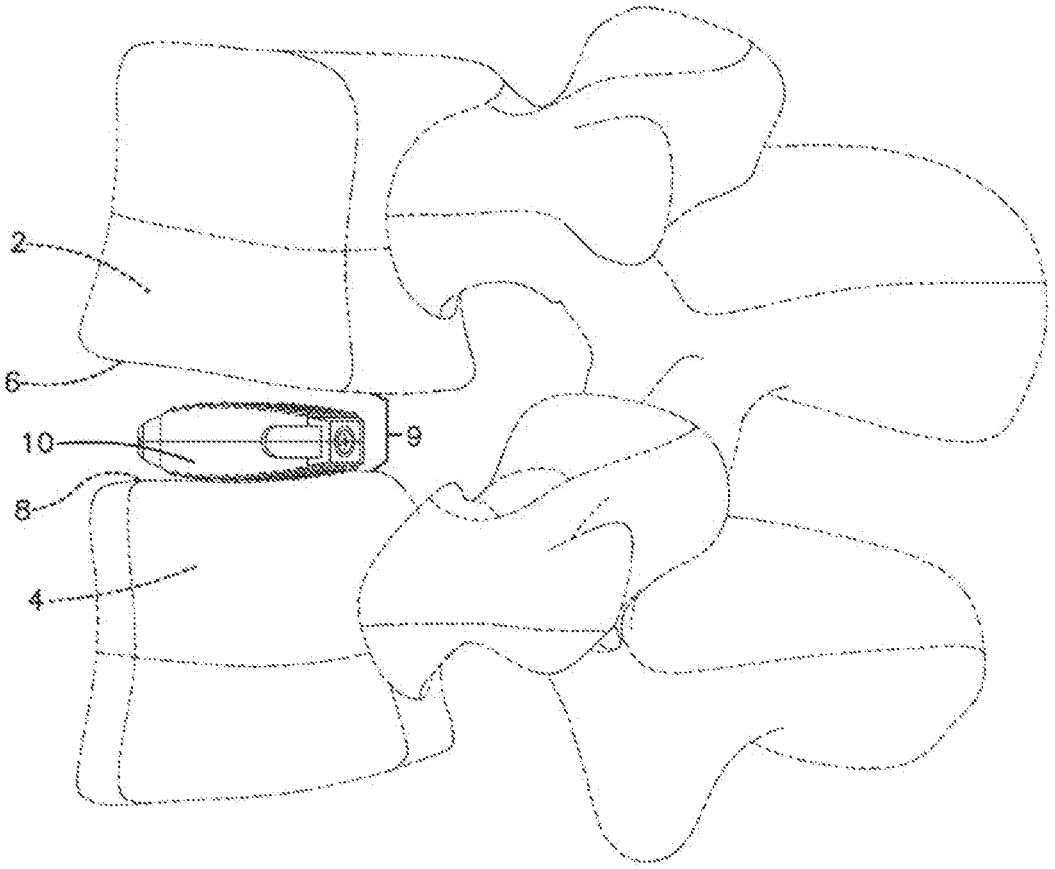
FIG. 1 illustrates an implant positioned between vertebral bodies, according to an embodiment of the present disclosure.
Figure 2A:
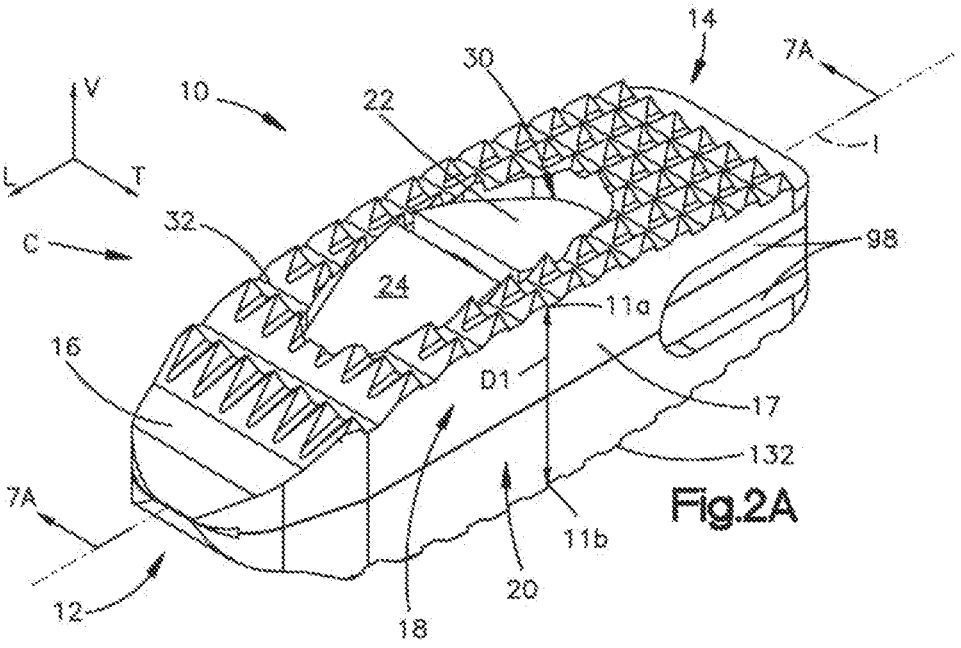
FIGS. 2A and 2B are perspective views of the implant shown in FIG. 1 in a collapsed configuration and an expanded configuration, respectively.
Figure 2B:
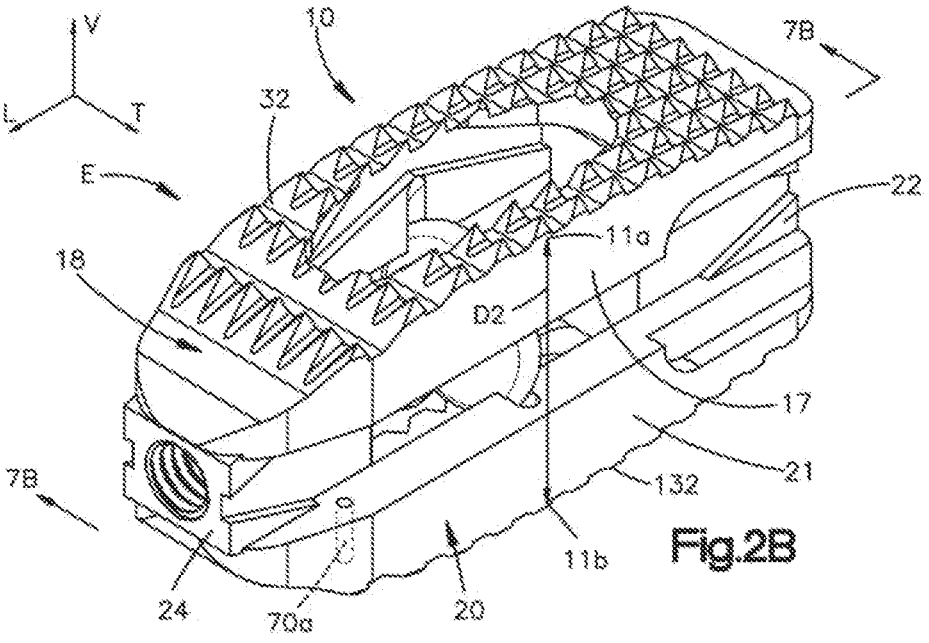

Referring to FIG. 1, a superior vertebral body 2 and an adjacent inferior vertebral body 4 defines an intervertebral space 9 extending between the vertebral bodies 2 and 4. The superior vertebral body 2 defines superior vertebral surface 6, and the adjacent inferior vertebral body 4 defines an inferior vertebral surface 8. The vertebral bodies 2 and 4 can be anatomically adjacent, or remaining vertebral bodies after a vertebral body has been removed from a location between the vertebral bodies 2 and 4. The intervertebral space 9 in FIG. 1 is illustrated after a discectomy, whereby the disc material has been removed or at least partially removed to prepare the intervertebral space 9 to receive an intervertebral implant or implant 10, as shown in FIGS. 2A-2B. The inserted and expanded implant 10 can achieve appropriate height restoration. The intervertebral space 9 can be disposed anywhere along the spine as desired, including at the lumbar, thoracic, and cervical regions of the spine.

Certain terminology is used in the following description for convenience only and is not limiting. The words "right", "left", "lower" and "upper" designate directions in the drawings to which reference is made. The words "inner" or "distal" and "outer" or "proximal" refer to directions toward and away from, respectively, the geometric center of the implant and related parts thereof. The words, "anterior", "posterior", "superior," "inferior," "medial," "lateral," and related words and/or phrases are used to designate various positions and orientations in the human body to which reference is made and are not meant to be limiting. The terminology includes the above-listed words, derivatives thereof and words of similar import.

The implant 10 is described herein as extending horizontally along a longitudinal direction "L" and a transverse direction "T", and vertically along a vertical direction "V". Unless otherwise specified herein, the terms "longitudinal," "transverse," and "vertical" are used to describe the orthogonal directional components of various implant components and implant component axes. It should be appreciated that while the longitudinal and transverse directions are illustrated as extending along a horizontal plane, and that the vertical direction is illustrated as extending along a vertical plane, the planes that encompass the various directions may differ during use. For instance, when the implant 10 is inserted into an intervertebral space, such as the intervertebral space 9, the vertical direction V extends vertically generally along the superior-inferior (or caudal-cranial) direction, while the horizontal plane defined by the longitudinal direction L and transverse direction T lies generally in the anatomical plane defined by the anterior-posterior direction, and the medial-lateral direction. Accordingly, the directional terms "vertical" and "horizontal" may be used to describe the implant 10 and its components as illustrated merely for the purposes of clarity and illustration.

Referring to FIGS. 1-3, the expandable intervertebral implant or implant 10 extends between a distal or insertion end 12 and proximal or trailing end 14 that is spaced from the insertion end 12 along an implant axis 1. The implant axis 1 can extend along the longitudinal direction L or any other linear or nonlinear direction as desired. The trailing end 14 is configured to couple with one or more insertion instruments, which are configured to support and carry the implant 10 into the intervertebral space 9, and/or actuate the implant 10 from a collapsed configuration C shown in FIG. 2A into an expanded configuration E shown in FIG. 2B. The implant 10 can also extend between an upper or first bone-contacting surface 32 and a lower or second bone contacting surface 132 spaced from the first bone-contacting surface along the vertical direction V. The bone contacting surfaces 32 and 132 are configured to engage opposing vertebral bodies 4 and 6, respectively. Each bone-contacting surface can be convex or partially convex, for instance, one portion of the surface is convex while another portion can be planar. The bone contacting surfaces 32 and 132 can also define a texture 41, such as spikes, ridges, cones, barbs, indentations, or knurls, which are configured to engage respective vertebral bodies 4 and 6 when the implant 10 is inserted into the intervertebral space 9. The bone contacting surfaces 32 and 132 may be partially textured. For instance, the bone contacting surfaces 32 and 132 can include specific patterns of textured and non-textured portions. As used herein, the term "proximal" and derivatives thereof refer to a direction from the distal or insertion end 12 toward the proximal end 14. As used herein, the term "distal" and derivatives thereof refer to a direction from the proximal end 14 toward the insertion end 12. As used herein, the term "superior" and derivatives thereof refer to a direction from the bone contact surface 132 toward the first bone-contacting surface 32. As used herein, the term "inferior" and derivatives thereof refer to a direction from the upper or first bone-contacting surface 32 toward the lower or second bone contacting surface 132.

Continuing with FIGS. 1-3, the implant 10 includes a first or superior plate 18, a second or inferior plate 20 opposing the superior plate 18 along the vertical direction V, and a pair of wedge members. The pair of wedge members include a first wedge member 22 and a second wedge member 24 that couple to the superior plate 18 to the inferior plate 20. The first and second wedge members 22 and 24 are translatable along the longitudinal direction or the implant axis 1 so as separate the superior plate 18 from the inferior plate 20 along the vertical direction V. The implant 10 can include an actuation member 26 coupled to the first wedge member 22 and the second wedge member 24. The actuation member 26 has a flange 28 protruding from the actuation member 26 along the vertical direction V toward the superior plate 18 and the inferior plate 20. The superior plate 18 can define a first lumen 30 and the inferior plate 20 can define a second lumen 31 aligned with and opposite to the first lumen 30. The implant 10 is configured such that when the implant 10 is in the collapsed configuration C shown in FIG. 2A, a portion of first wedge member 22 and the second wedge member 24 are disposed at least partially in the first lumen 30 and the second lumen 31. The implant plates and/or wedge members can be formed of polyether ether ketone (PEEK) or any other suitable biocompatible polymeric material. The actuation member can formed from a biocompatible polymeric material or metallic alloy, such as titanium or steel. It should appreciated that the any suitable material can be used to form the implant components as described herein.

Figure 4D:
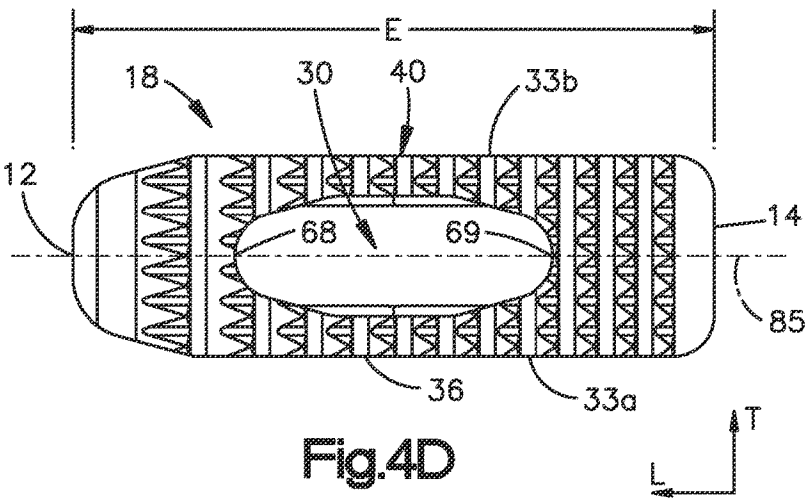

Referring to FIGS. 3-4D, the superior plate 18 is configured for coupling with the first wedge member 22, the second wedge member 24, and at least a portion of the actuation member 26, for support on the flange 28. The superior plate body 17 can define a cavity 42 configured carry the first and second wedge members 22 and 24 are the actuation member 26. The superior plate 18 defines a first or superior plate body 17 that extends between the insertion end 12 and the trailing end 14 along the longitudinal direction L. The superior plate body 17 defines the first bone-contacting surface 32, and first and second interior plate contact surfaces 34 and 38 spaced from the bone-contacting surface 32 along the vertical direction V. The superior plate body 17 also defines first and second ramp surfaces 44 and 46 spaced from the bone contacting surface 32 along the vertical direction V. The plate body 17 further defines a first side 33a and a second side 33b opposite the first side 33a. The first and second sides 33a and 33b extend between the bone-contacting surface 32 and respective interior plate contact surfaces 34 and 38 along the vertical direction V. The plate body 17 also defines a first vertical surface 37 and a second vertical surface 39 that extend from the ramp surface 44 and 46 to respective interior plate contact surfaces 34 and 38 along the direction V. The plate body 17 thus defines a first sidewall 36 and a second sidewall 40 spaced from the first sidewall 36 along the transverse direction T. Specifically, the first sidewall 36 extends between the side 33a and vertical surface 37 along the transverse direction T, and from the ramp surfaces 44 and 46 to the interior plate contact surface 34 along the vertical direction V. The second sidewall 40 extends between the side 33b and vertical surface 39 along the transverse direction T, and from the ramp surfaces 44 and 46 toward the interior surface 38 along the vertical direction V. As illustrated, the cavity 42 extends along the longitudinal direction L of the plate body 17 and along the transverse direction T between opposing first and second walls 36 and 40. The first lumen 30 is in communication with the cavity 42 as detailed below. In the embodiment shown, the first and second walls 36 and 40 converge with the bone contacting surface 32 to form a tapered insertion end 16 (FIG. 2A).

Continuing with FIGS. 3-4D, the first and second walls 36 and 40 are configured to couple to the first and second wedge members 22 and 24. The first wall 36 can define at least one slot, for instance a first slot 52 for receiving a portion of the flange 28 of the actuation member 26. The first slot 52 is disposed in the first wall 36 at a location between the insertion end 12 and the trailing end 14 of the plate body 17. The second wall 40 can define at least one or second slot 54 for receiving another portion of the flange 28 of the actuation member 26. The second slot 54 is disposed in the first wall 36 at a location between the insertion end 12 and the trailing end 14 of the plate body 17. The second slot 54 is aligned, for instance transversely aligned, with and opposing the first slot 52 such that each slot 52 and 54 is positioned to receive a portion of the flange 28. The first and second slots 52 and 54 are also configured to mate with the structure of the flange 28. For instance, the first and second slots have an inner profile that is curvilinear and corresponds to the curvilinear profile of the flange 28. In other alternate embodiments, the first and second slots 52 and 54 may have a rectilinear shape. It should be appreciated that the slots 52 and 54 may have any desired shape that can slidingly receive a portion of the flange 28. For example, if the flange 28 has a square profile, the slots 52 and 54 can be configured to mate with the square shaped flange. In alternate embodiments, the first and second wall 36 and 40 can include a plurality of spaced slots spaced apart along the longitudinal direction L and disposed on the first and second walls 36 and 40 to receive a corresponding number of flanges or flanges portions protruding from the actuation member 26. For example, the first and second walls may include slots 52 and 54, and additional slots [52L and 54L] (not shown) spaced apart from the slots 52 and 54 along the longitudinal direction (the longitudinal direction L).

The plate body 17, or for instance the first and second walls 36 and 40, can define one or more projections 56 and 58 that protrude from the walls 36 and 40 along the transverse direction T. The projections 56 and 58 are configured to engage a portion of the first and second wedge members 22 and 24 as further detailed below. In particular, the first wall 36 can define a first set of projections 56 that extend from the first wall 36 along the transverse direction T into the cavity 42. The first set of projections 56 can include a first wall projection 56a and a second wall projection 56b spaced proximally from the first wall projection 56a along the longitudinal direction L. In the illustrated embodiment, the first slot 52 separates the first wall projection 56a from the second wall projection 56a. The second wall 40 can define a second set of wall projections 58 that extend from the second wall 40 along the transverse direction T into the cavity 42. The second set of projections 58 can include a third wall projection 58a and a fourth wall projection 58b spaced proximally from the third projection 58a along the longitudinal direction L. In the illustrated embodiment, slot 54 separates the third wall projection 58a from the fourth wall projection 58b. While each wall 36 and 40 is illustrated has having two projections, each wall 36 and 40 can have a single projection, or more than two projections.

The plate body 17, for instance the first and second walls 36 and 40, can further define [set] *sets* of inclined connection grooves [60] *60a-60b* and [62] *62a-62b* configured to receive a portion of the first and second wedge members 22 and 24. The wall projections 56 and 58 protrude from respective walls 36 and 40 along the transverse direction T, as discussed above. The wall projections 56 and 58 are also spaced from the respective first and second ramp surfaces 44 and 46 along the vertical direction V to define the sets of inclined connection grooves [60] *60a-60b* and [62] *62a-62b*. The first set of projections 56a and 56b extend from the first wall 36 so as to define first and second inclined connection grooves 60a and 60b respectively (FIG. 4A). The second connecting groove 60b is proximal disposed relative to the first connection groove 60a. The slot 52 is disposed between the first and second inclined connection grooves 60a and 60b. The second set of projections 58a and 58b extend from the first wall 40 to define third and fourth inclined connection grooves 62a and 62b, respectively. The fourth connection groove 62b is proximal to the third inclined connection groove 62a. The slot 54 is disposed between the inclined connection grooves 62a and 62b. The first and third projections 56a and 58a can also be referred to as the distally positioned projections, while the second and fourth projections 56b and 58b can be referred to as proximally positioned projections. Further, the first and third inclined connection grooves 60a and 62a can be referred to as the distally positioned connection grooves, while the second and fourth inclined connection grooves 60b and 62b can be referred to as the proximally positioned connection grooves.

Each opposing inclined *set of* connection grooves [60] *60a-60b* and [62] *62a-62b* extends from the lumen 30 toward the opposing implant or implant ends 12 and 14 along the longitudinal direction L. The plate body 17 can define a lumen first perimeter portion 68 and an opposing lumen second perimeter portion 69 that is spaced from the first perimeter portion 68 along the first lumen axis 85. Lumen perimeter portion 69 is disposed proximally toward the trailing end 14 of the implant 10 and lumen perimeter portion 68 is disposed distally toward the insertion end 12 of the implant 10. The distally positioned grooves 60a and 62a extend distally from the first perimeter portion 68 of the lumen 30 toward the plate insertion end 12, while the proximally positioned grooves 60b and 62b extend proximally from the second perimeter portion 69 of the lumen 30 toward the trailing end 14. The inclined connection grooves [60] *60a-60b* and [62] *62a-62b* can thus slidably receive therein the ridges 82 and 182 of the first and second wedge members 22 and 24.

Continuing with FIGS. 3-4C, the plate body 17 defines ramp surfaces 44 and 46, for instance a first ramp surface 44 and a second ramp surface 46 that are configured to mate with and slide along portions of the first and second wedge members 22 and 24. The first ramp surface 44 extends from the first perimeter portion 68 of the lumen 30 distally generally along the longitudinal direction L to the insertion end 12. The ramp surface 44 is inclined to abut and slidingly receive a portion of the second wedge member 24. The second ramp surface 46 extends from the second perimeter portion 69 of the lumen 30 proximally along the longitudinal direction L toward the trailing end 14. The ramps surfaces 44 and 46 also extend transversely along the transverse direction T between the opposing first and second plate walls 36 and 40. Each ramp surface 44 and 46 can define a ramp angle β (not shown) defined with respect to interior plate contact surfaces 34 and 38. It should be appreciated that the angle β can vary as needed. The plate body 17 can also define a curvilinear portion 48 disposed at the trailing end 14 of the plate body 17 and in communication with the second ramp surface 46. The curvilinear portion 48 is configured align with a corresponding curvilinear portion 148 on the inferior plate 20. When the plates 18 and 20 are in the collapsed configuration as shown in FIGS. 2A and 7A, the curvilinear portions 48 and 148 define an access opening 50. The access opening 50 that provides access the actuation member 26, as further detailed below.

Continuing with FIGS. 3-4D, the superior plate 18 can include one or more radiographic markers. The plate body 17 can define one or more bores (not shown) sized and dimensioned to receive a radiographic marker 70a therein. As illustrated *in FIGS. 4A and 4C*, the radiographic marker 70a is disposed in the second wall 40 and positioned toward insertion end 12 of the plate 18. The opposing plate 20 can have a radiographic marker [170a] *70a* as well, *as shown in FIGS. 2B and 3*. When the implant 10 is inserted into the intervertebral space 9, and the implant 10 is expanded from the first configuration C to the expanded configuration E, the markers 70a [and 170a] can separate along the vertical direction V. With image analysis, the extent of plate separation can be determined or indicated by observing the extent of separation between the [markers] *marker* 70a [and 170a] disposed in the superior plate 18 compared to *the* marker *70a* disposed in the inferior plate 20.

The inferior plate 20 is configured similarly to the superior plate 18. The inferior plate 20 thus includes similar structural features that correspond to the structural features described above with respect to the superior plate 18. The inferior or second plate 20 defines a plate body 21 that extends between the insertion end 12 and the trailing end 14 along the longitudinal direction L. The inferior plate body 21 defines a second bone contacting surface 132, first and second plate contact surfaces 134 and 138 spaced from the bone contacting surfaces 32 along the vertical direction V, and first and second ramp surfaces 144 and 146 spaced from the bone contacting surfaces 32 along the vertical direction V. The inferior plate body 21 therefore defines define cavity 142, first and second walls 136 and 140, a first set of projections 156a-b, a second set of projections 158a-b, and inclined connection grooves 160a-b, 162a-b. The interior surfaces 134 and 138 of the inferior plate 20 are configured to oppose and contact the interior contact surfaces 34 and 38 of the superior plate 18. The superior plate 18 and inferior plate 20 can define opposing indentations 98 and 99 at the trailing end 14 of the implant 10. The indentations 98 and 99 are configured to receive a portion of an insertion tool 100 and 300 (FIG. 8A-8F).

The first and second plates 18 and 20 can also define the respective first and second lumens 30 and 31 as discussed above. Each lumen 30 and 31 has been configured to configured receive at least a portion of the first and second wedge members 22 and 24 to maximize the compact design and the expansion characteristics of the implant 10. The lumens 30 and 31 partially receiving portions of the first and second wedge members 22 and 24 when the implant 10 is in the collapsed configuration C (FIG. 2A), which allows for the dimensions of the first and second wedge members 22 and 24 to be increased over wedge members used in implants with lumens not configured to permit a portion of the wedge member to extend therethrough. Further, the configured first and second wedge members 22 and 24 can improve implant 10 stability when expanded. Thus, the implant 10 has a collapsed configuration that is compact and less invasive, and an expanded configuration that is dimensionally stable. The lumens 30 and 31 have the additional benefit of promoting bone growth when implanted in the intervertebral space 9. The first lumen 30 and second *lumen* 31 are generally elongate in the longitudinal direction L. The lumens 30 and 31 can have other shapes, for instance the lumens can be circular (FIGS. 9-11B). The lumen 30 extends through the superior plate body 17 along the vertical direction V into communication with the cavity 42. Likewise, the second lumen *31* extends through the second or inferior plate body 21 into communication with the cavity 142. The superior plate body 17 can define a lumen axis 85 that extends along the longitudinal direction L of plate body 17. The lumen axis 85 is aligned with the bone-contacting surface 32 or at leady portion thereof, for instance the lumen axis 85 is spaced from the implant axis 1 along the vertical direction V with a portion of the bone-contacting surface 32. The plate body 17 can also define a lumen first perimeter portion 68 and an opposing lumen second perimeter portion 69 that is spaced from the first perimeter portion 68 along the first lumen axis 85. Lumen perimeter portion 68 is disposed proximally toward the implant trailing end 14 and lumen perimeter portion 69 is disposed distally toward the implant insertion end 12. Likewise, the inferior plate body 21 can define a second lumen axis 85a [(not shown)] that extends along the longitudinal direction L of plate body 21 and is aligned along the vertical direction V with bone contacting surface 132. The plate body 21 can also define a lumen first perimeter portion 168 and an opposing lumen second perimeter portion 169 that is spaced from the first perimeter portion 168 along the second lumen axis 85a. Lumen perimeter portion 168 is disposed proximally toward the trailing end 14 and lumen perimeter portion 169 is disposed distally toward the implant insertion end 12.

Referring to FIGS. 3, 5A-5D, the first wedge member 22 and the second wedge member 24 are configured for slidable coupling to the superior and inferior plates 18 and 20. The first and second wedge members 22 and 24 are configured similarly, and for illustrative purposes, only the first wedge member 22 will be described below. The first wedge member 22 defines a wedge body 74 extending along a wedge axis 3 between a narrow end 75 and an inner end 76 spaced from the narrow end 75. The wedge axis 3 is generally aligned with the implant axis 1 and extends along the longitudinal direction L. As show in FIGS. 3 and 7A, the first wedge narrow end 75 is positioned toward the outer or trailing end 14 of the implant 10, while the inner end 76 is positioned to face the distal or insertion end 12 of the implant 10. Further, the second wedge member 24 has a wedge body 174 that extends from a narrow end 175 to an inner end 176 along the wedge axis 3, wherein the narrow end 175 is positioned toward the distal or insertion end 12 of the implant 10 and the inner end 176 is positioned toward the proximal or trailing end 14 of the implant. Thus, the first wedge member 22 is positioned such that the inner end 76 of the first wedge member 22 and faces the inner end 176 of the second wedge member 24.

The body 74 defines a superior tip 76s spaced from an inferior tip 76i along a vertical direction V and disposed at the inner end 76. A first or inner wedge dimension H1 is defined as the distance between the superior and inferior tips 76s and 76i along the vertical direction V. The plate body 17 can define first plate dimension [L51] *S1* (*FIG. 4B*) extending between the bone contacting surface 32 and the interior contact surfaces 34 and 38, while the plate body 21 can define a second plate dimension [52] *S2* (*FIG. 3*) extending between the bone contacting surface 132 and the inner surfaces 134 and 138 (*in similar fashion to the first plate dimension S1*). In an embodiment, the first or inner wedge dimension H1 is about twice the distance of the first plate dimension [S] *S1*. In an embodiment, the first or inner wedge dimension H1 can be greater than or equal to the sum of the first plate dimension [S] *S1* and the second plate dimension [52] *S2*. In an embodiment, the first or inner wedge dimension H1 can be less than or equal to sum of the first plate dimension S1 and second plate dimension [52] *S2*.

Figures 5A, 5B, 5C, 5D:
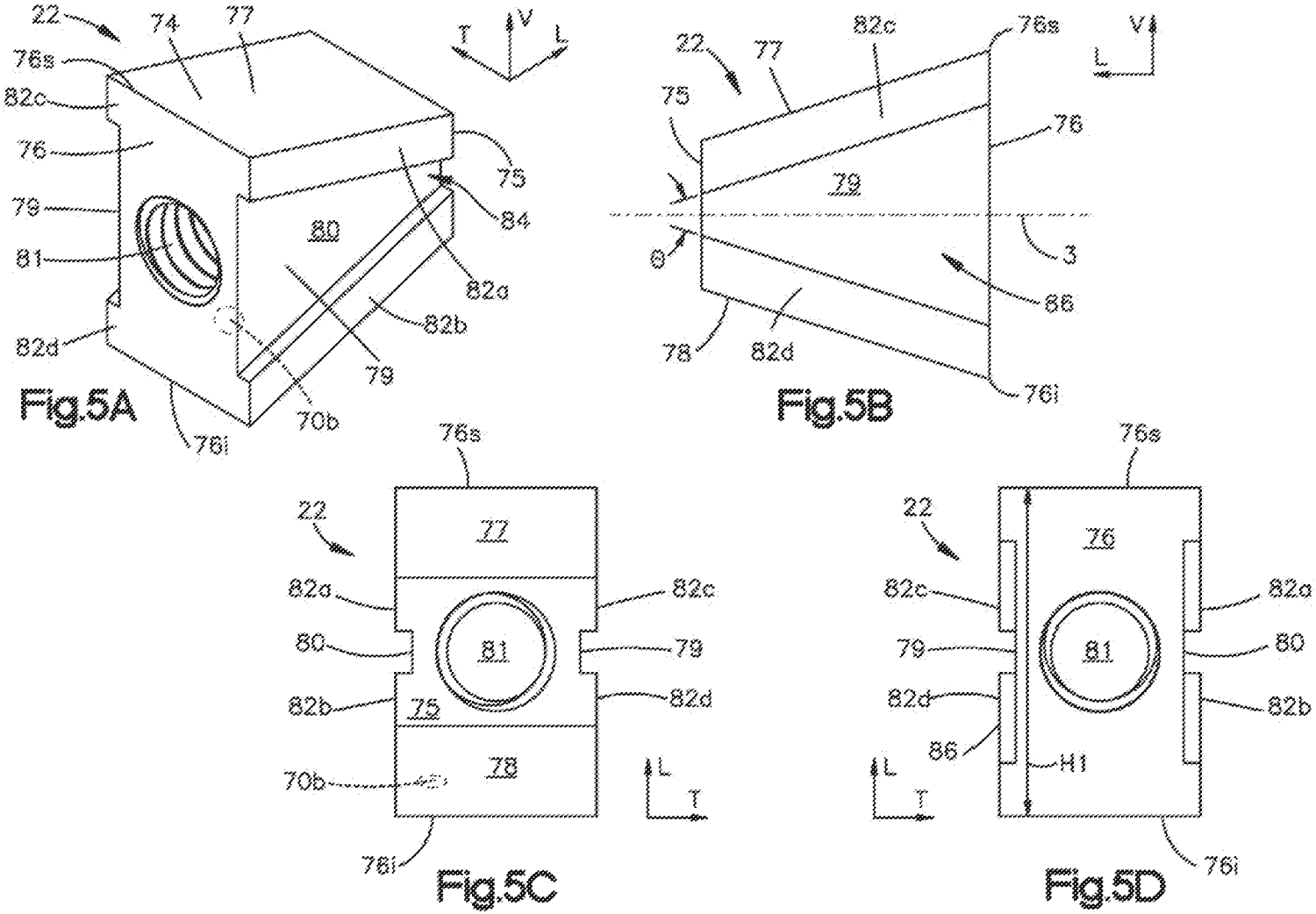
FIGS. 5A, 5B, 5C, and 5D are perspective, side, and opposing ends views of a wedge member used in the implant shown in FIG. 1.
Figure 6A:
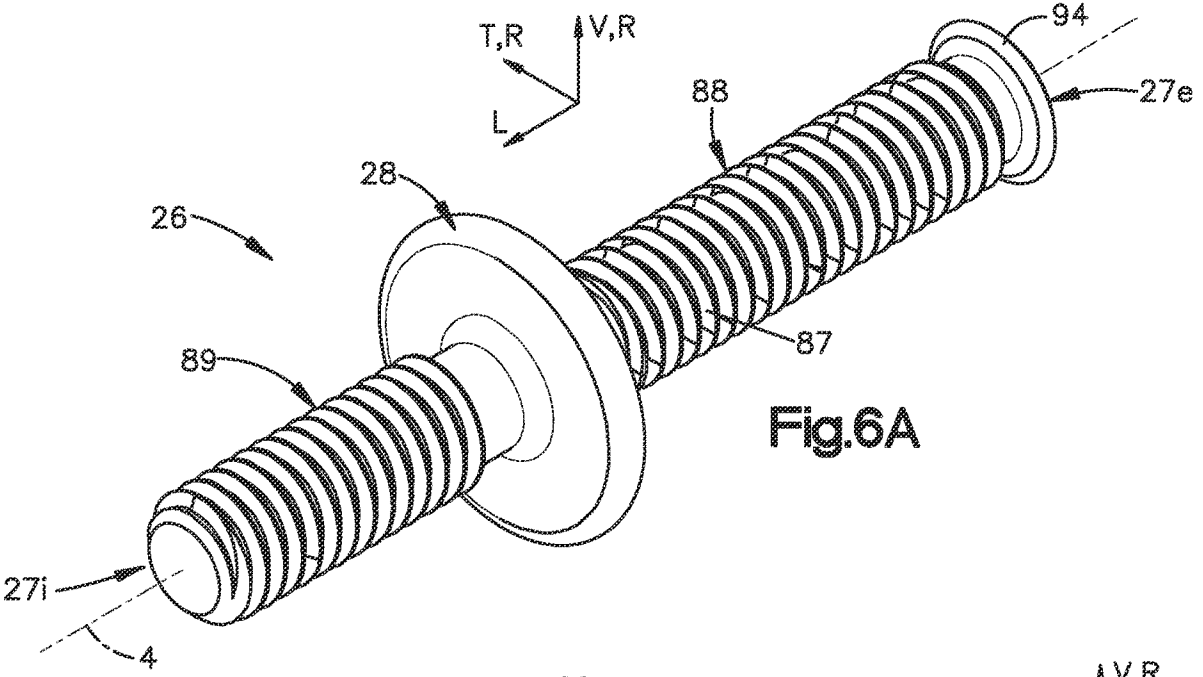

The body 74 defines a wedge shape configured for slidable coupling to the first and second plates 18 and 20. The body 74 defines a first or superior inclined surface 77 and a second inclined or inferior inclined surface 78 opposite the first incline surface 77. The first and second inclined surfaces 77 and 78 extend along the longitudinal direction L from the inner end 76 toward the narrow end 75. The first inclined surface 77 is angularly offset from a second inclined surface 78. In an embodiment, the first and second inclined surfaces form an angle θ defined between intersecting lines coincident with the first and second inclined surfaces 77 and 78 (FIG. 5B). Angle θ can vary as needed. The first inclined surface 77 can slidably mate with a ramp surface 46 on an interior the superior plate 18, while the second inclined surface 78 can slidably mate with a first ramp surface 146 on of the inferior plate 20. The body further defines a first side 79 and a second side 80 opposite the first side 79. The first and second sides 79 and 80 extend along the longitudinal direction L between the inner end 76 and the narrow end 75, and vertically along the vertical direction V between the first and second inclined surfaces 77 and 78.

The first wedge member 22 also includes one or more ridges 82 (82a-d) protruding from the body 74 along the transverse direction T. The ridges 82 are configured to couple the first wedge member 22 to the superior plate 18 and inferior plate 20. For instance, the one or more ridges 82 are slidably coupled to respective portions of the inclined connections grooves [60] *60a-60b*, [62 160] *62a-62b, 160a-160b*, [162] *162a-162b*. Each ridge 82a-82d extends between the narrow end 75 and the inner end 76 of the body 74 generally along the wedge axis 3. Ridges 82a-82d also extend along the respective first and second inclined surfaces 77 and 78. Ridges 82a and 82c are angled only offset action angle with respect to ridges 82b and 82d. The vertically spaced apart ridges 82c and 82d disposed on the first side 79 of the body 74 can define a recess portion 86 which can receive the distally oriented projections 56b and 156b of the plates 18 and 20, respectively. The vertically spaced apart ridges 82a and 82b are disposed on the side 80 define recess portion 84 which receives the distally oriented projections 58b and 158b of the plate 18 and 20. The transversely spaced apart ridges 82a and 82c are received in the inclined connection grooves 60b and 62b of the superior plate. The other transversely spaced apart ridges 82b and 82d are received in the inclined connection grooves 160b and 162b of the inferior plate 20 (FIG. 3).

The wedge member body 74 also defines first bore 81 extending through the body 74 between the narrow end 75 and the inner end 76 along the wedge axis 3. The first bore 81 is configured to receive at least a portion of the actuation member 26. In an embodiment, the bore 81 is internally threaded to mate with a corresponding threaded portion of the actuation member 26. Further, the wedge member body 74 includes an additional bore or receiving a radiographic marker 70b therein.

The second wedge member 24 is configured similarly to the first wedge member 22. The second wedge member 24 defines a second body 174. The body 174 defines a narrow end 175 spaced apart from an inner end 176 along the wedge axis 3, first and second inclined surfaces 177 and 178, a plurality of ridges 182 extending from body 174, and a second bore 181 extending through the body 174 between the narrow and inner ends 175 and 176. The first and second sides 179 and 180 extend between the inclined surfaces 177 and 178. The body 174, for instance the body inner end 176 defines a superior tip 176, spaced apart from an inferior tip 176i along a vertical direction V. The second wedge member has a wedge dimension H2 (not shown) defined as the distance between the superior tip 176s and the inferior tip 176i. H2 can be equal to H1. As shown in FIG. 3, the second wedge member 24 is spaced apart from the first wedge member 22 along the longitudinal direction L such that the inner end 175 of the second wedge member 24 faces the inner end 75 of the first wedge member 22. The second wedge member 24 also includes ridges 182a-182d that are similar to ridges 82a and 82d.

Continuing with FIGS. 3-4D, the actuation member 26 is configured to couple the first and second wedge members 22 and 24 together while also providing stability to the superior plate 18 and inferior plate 20 during implant expansion. The actuation member 26 extends along the longitudinal direction L between a distal end 27i and a proximal end 27e. The actuation member 26 defines a shaft 87 extending between the opposed ends 27i and 27e. The flange 28 protrudes from the shaft 87 along the transverse T or a radial direction R. The flange 28 defines a flange body 28b, a distal facing surface 29d and a proximal facing surface 29p spaced from the distal facing surface 29d along the longitudinal direction L. The flange body 28b is sized and dimensioned to slide within the slots 52 and 54 of plate 18, and slots 152 and 154 of the plate 20. The radial direction R can be aligned with the transverse direction T and the vertical direction and is used to indicate that the flange 28 protrudes radially from the shaft 87. The flange 28 can have other configurations, and as such Cartesian coordinates may better indicate directional components.

The shaft 87 can define a first threaded portion 88 disposed proximally relative to the flange 28, and a second threaded portion 89 disposed distally from the flange 28. The first shaft portion 88 can have a length L1 extending from the flange proximal face 29p to the proximal end 27e, and the second threaded portion 89 has a second length L2 extending from the flange distal face 29d to the distal end 27i, wherein the first length L1 is greater than the second length L2. The shaft 87 is configured to extend through the bore 81 of the first wedge member 22 and into the curvilinear portions 48 and 148 or access opening 50 of the plates. The first threaded portion 88 has a thread pattern that is oriented in the opposite direction of the thread pattern formed on the second threaded portion 89. The internal threads of the first and second bores 81 and 181 are in opposing orientations such that when the actuation member 26 rotates, the first and second wedge members 22 and 24 translate along the actuation member 26 toward each other or away from each depending on the rotation direction of the actuation member 26. The thread pattern on each portion may have the same pitch such that the first and second wedge members 22 and 24 can translate along the actuation member 26 at the same rate. The thread pitch can be different if needed when different distraction profiles are desired in the expanded configuration (e.g. kyphotic or lordotic). The proximal end 27e of the actuation member 26 can define a lip 94 configured to abut the narrow end 75 of the first wedge member 22. The lip 94 and can help prevent displacement of the actuation member 26 from the first wedge member 22. The proximal end 27e of the actuation member 26 can define a socket 90 configured to receive or support a portion of an instrument, as further detailed below. The socket 90 can have any configuration ass need to receive an instrument, such as hex, Phillips, flat, star, etc.

The implant 10 as described herein can have initial dimensions and expanded dimensions. For, instance, the implant can have first implant height D1 defined between opposing portions 11a and 11b of the first and second bone contacting surfaces 32 and 132, and second implant height D2 defined between opposing portions 11a and 11b of the first and second bone contacting surfaces 32 and 132 when the implant is expanded (FIGS. 2A and 2B). In an embodiment, the first implant height D1 can range between 7 mm and 10 mm, and the second expanded height can range between 10 mm and 13 mm. For instance, in an embodiment, the first height can be 7 mm while the expanded, second height can be 10 mm. In another embodiment, the first height can be 9 mm and the expanded, second height D2 can be 13 mm. Other dimensions are possible as well. For example first heights can be up to 7 mm, 9 mm, or greater. The implant 10 can have length E defined between the distal or insertion end 12 and the proximal or trailing end 14. The length E can range between 24 mm and 32 mm. The length E, however, can be shorter than 24 mm or greater than 32 mm. Further, the implant is configured such the length E of the implant 10 is consistent regardless of when the implant 10 is in the collapsed configuration or when the implant 10 is in the expanded configuration. That is, the first and second wedge members 22 and 24 are configured such the opposed narrow ends 75 and 175 translate to, but do not protrude from the implant trailing end 14 or implant insertion end 12 when in the expanded configuration. This configuration improves implant stability.

Figure 8A:
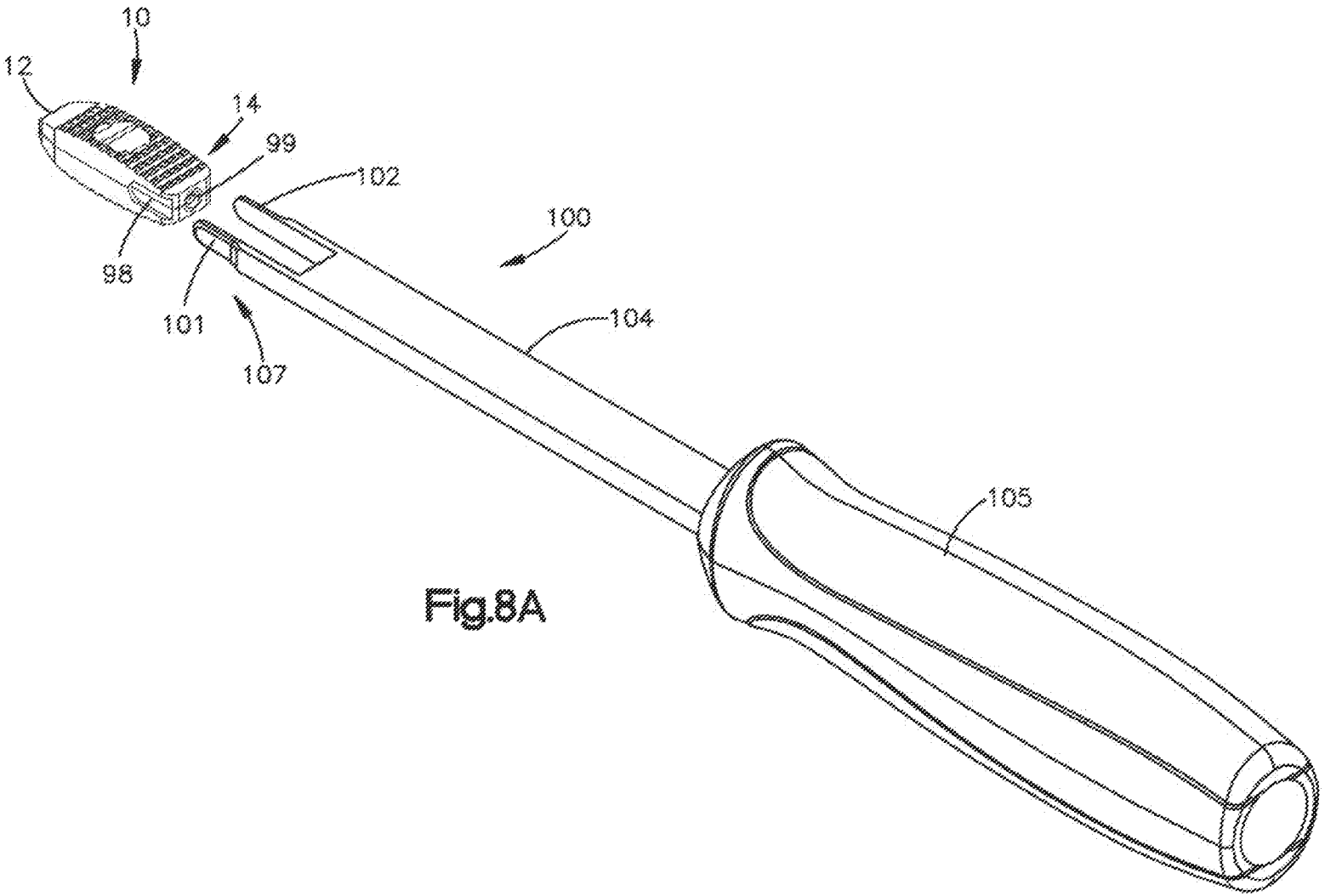
FIG. 8A is a perspective view of an insertion tool used to insert the implant shown in FIG. 1 into an intervertebral space.
Figure 8B:
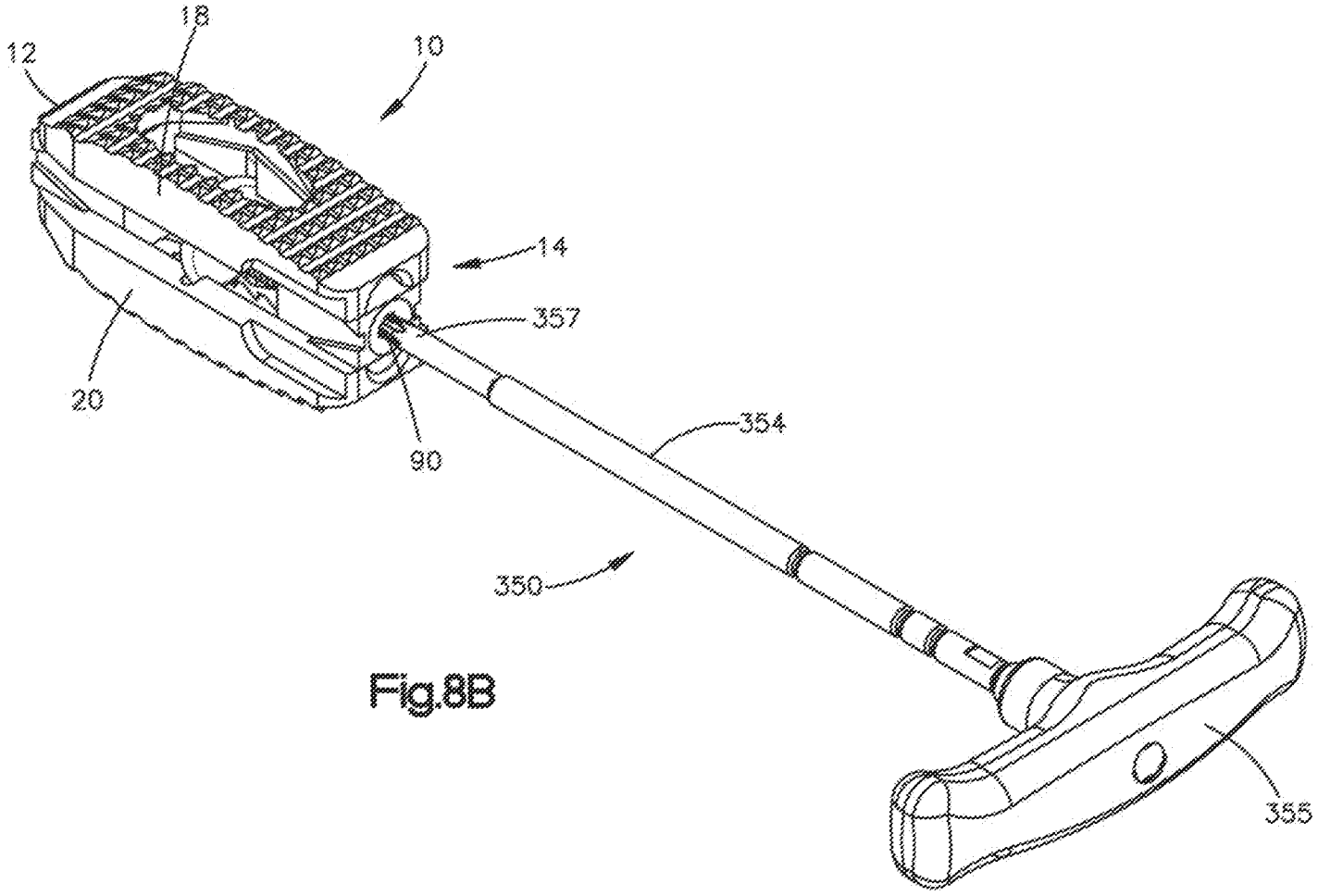
FIG. 8B is a perspective view of a tool engaged with the trailing end of the implant shown in FIG. 1.
Figure 8C:
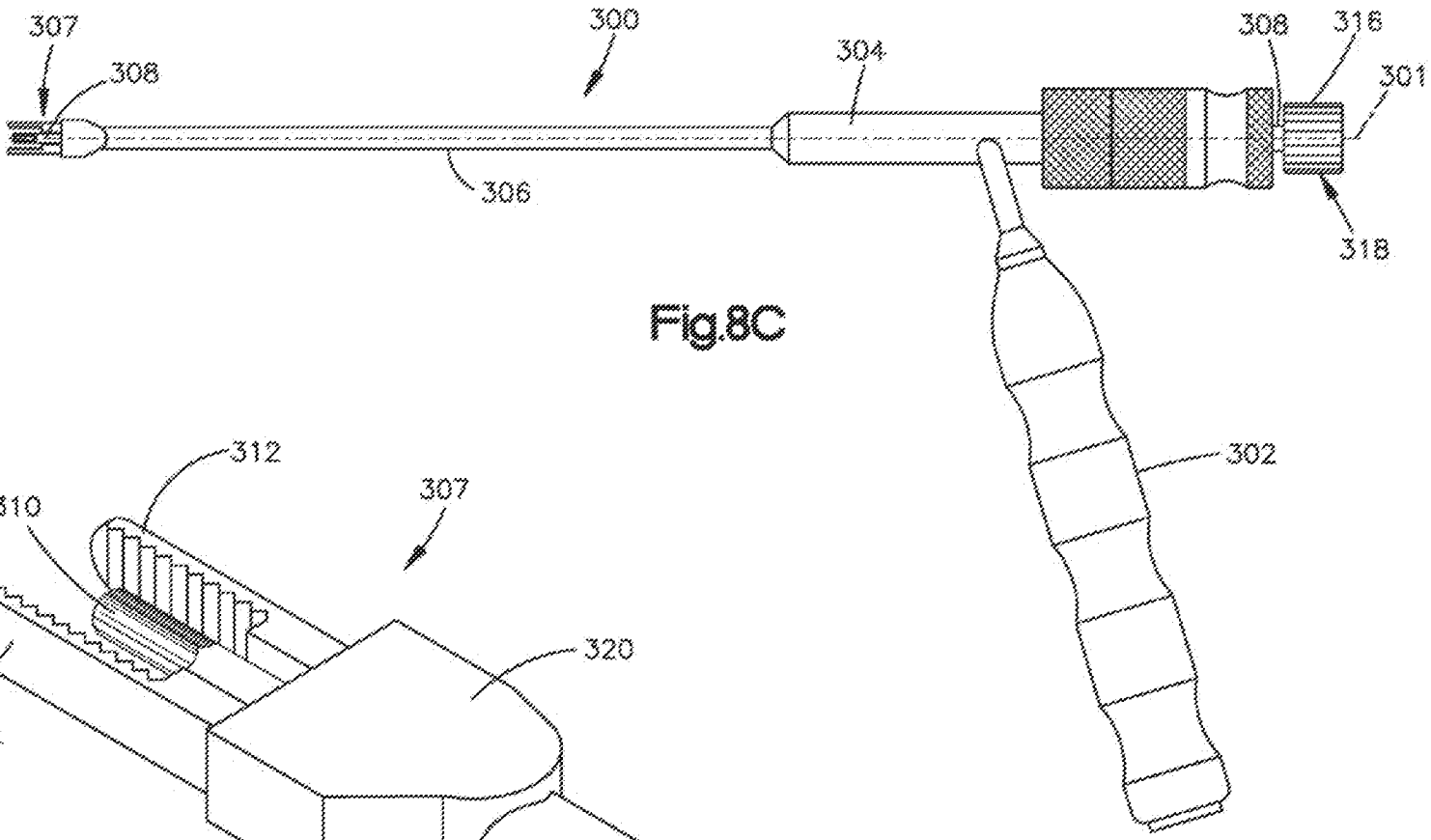
FIG. 8C is a side view of a tool according to another embodiment of the present disclosure.

Referring to FIGS. 8A-8C, the system as described herein includes one or more insertions tools. An insertion tool 100 can include a handle 105 and a shaft 104 extending from the handle toward an implant supporting end 107. The implant supporting end 107 is configured to support, for instance carry or engage with a portion of the implant 10. The implant supporting end 107 can include spaced apart tabs 101 and 102 configured and sized to be received in the implant indentations 98 and 99. When the implant tabs 101 and 102 engage the indentations 98 and 99, the tool 100 can position and/or insert the implant 10 into the intervertebral space 9. An additional tool 350 can be used to expand the implant 10 from the collapsed configuration to the expanded configuration. The tool 350 can include a handle 355 and a shaft 354 extending from the handle toward an implant supporting end 357. The implant supporting end 357 is configured to engage the actuation member 26, such that rotation of the tool 350 can cause rotation of the actuation member 56.

Figure 8D:
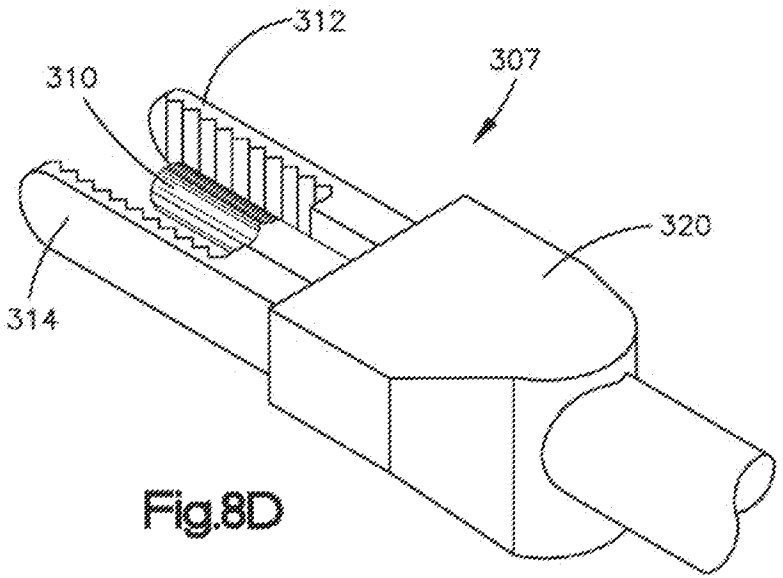
FIG. 8D is a partial perspective view of an implant supporting end of a tool shown in FIG. 8C.
Figure 8E:
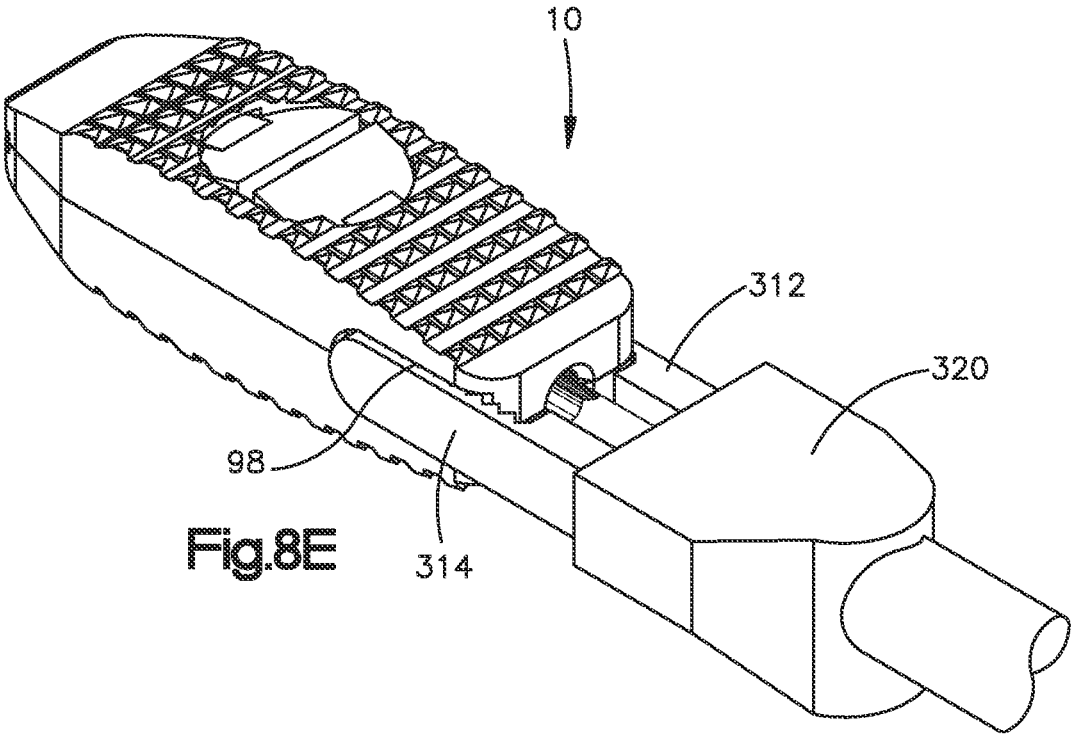

Referring to FIGS. 8D-8E, another embodiment a tool 300 can include a handle 302, tool housing 304 connected to the handle 302, and an elongate cannulated shaft 306 extending from the housing 304 toward an implant supporting end 307. The housing 304 and cannulated shaft 306 are elongate along an insertion tool axis 301. The housing 304 and cannulated shaft 306 define a cannulation (not shown) that extends through the housing 304 and shaft 306. The tool 300 also includes rotation member 318 that defines a rotation member 316 and an elongate rod 308 that extends from the rotation member 318 toward an engagement end 310 along the axis 301 as shown in FIG. 8D. The rotation member 318 is rotatable in the cannulation as well as slidable or translatable in the cannulation along the tool axis 301. The tool implant supporting end 307 includes a body 320 and tabs 312 and 314 extending from the body. The engagement end 310 of the rod 308 protrudes from the body 320 and is disposed between the tabs 312 and 314. Tool 300 can be used to clasp, insert, and then expand the implant. The tool 300 can be used clasp the implant 10 by inserting the tabs 312 and 314 into the indentations 98 and 99 while the rotation member 318 can be slide into engagement with the actuation member 26. For instance, the engagement end 310 can be coupled to the opening 90 in the actuation member 26 while tabs 312 and 314 support the implant 10. The rotation member 318 can be rotated relative to the shaft 306 so that the actuation member 26 is rotated.

Figure 7B:
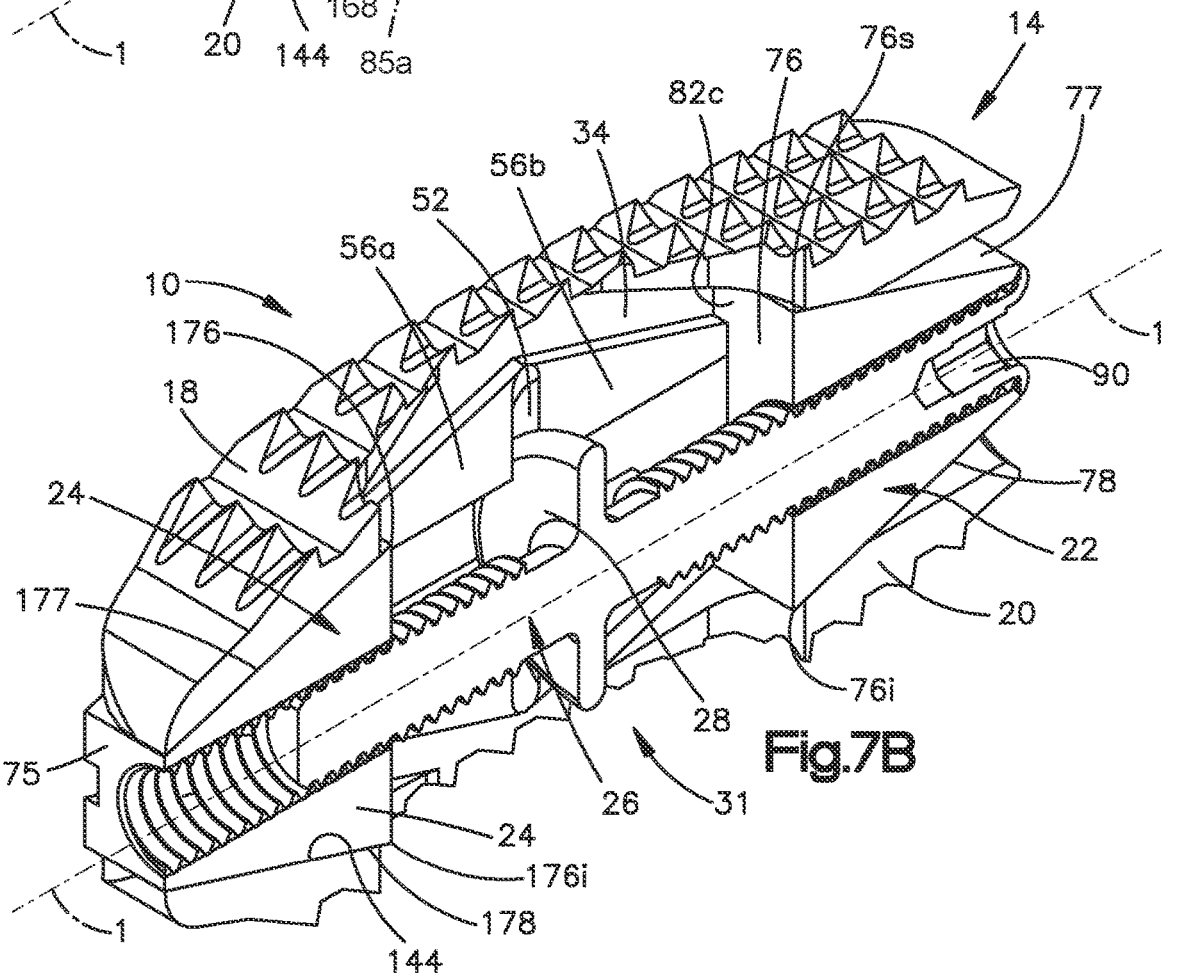

Referring to FIGS. 7A and 7B, implant 10 is configured to expand from the collapsed configuration C (FIG. 7A) to the expanded configuration E (FIG. 7B). When the first or collapsed configuration C, the first and second wedge members 22 and 24 are disposed in the implant such that the inner ends 76 and 176 face and are spaced apart from each other to define a gap therebetween. The actuation member 26 is coupled to the first and second wedge members 22 and 24 such that the first threaded portion 88 is disposed in the first bore 81 and the second threaded portion 89 is disposed in the second bore 181. The flange 28 extends between (in the sup) and along the opposed inner ends 76 and 176 of the first and second wedge members 22 and 24. The inclined surfaces 77 and 78 are adjacent to opposing plate ramp surfaces 46 and 146, while the second wedge member 24 inclined surfaces 177 and 178 are adjacent to opposing plate ramp surfaces 44 and 144. The inner end superior tips 76s and 176s extend into the lumen 30 and an into a plane containing the bone contacting surface 32, while the inner end tips 76i and 176i extend into the second lumen and to a plane containing the bone contacting surface 132. The flange distal face 29d abuts the inner end 176 of the second wedge member 24, while the flange proximal face 29p abuts the inner end 76 of the first wedge member 22. Portions of the first and second wedge members 22 and 24, for instance tips 76s-i and 176s-i, disposed in the lumens 30 and 31 allows for a wedge profile that aids plates 18 and 20 separation with relatively little advancement of the first and second wedge members 22 and 24 along the actuation member 26. For instance, the superior tips 76s and 176s extend to, for instance traverse, the first lumen axis 85 such that the tips are generally aligned with the bone contact surface 32 of the superior plate 18. The inferior tips 76i and 176i extend to, for instance traverse, the second lumen axis 85a such that the tips 76i and 176i are generally aligned with the bone contact surface 132 of the inferior plate 20.

Turning to FIGS. 7B and 8A-8F, when the actuation member 26 is rotated [for] via a tool [150] *300* or 350, the first threaded portion 88 of the actuation member 26 causes the first wedge member 22 to translate toward the trailing end 14 of the implant 10. The inclined surfaces 77 and 78 bears against the ramp surfaces 46 and 146 to separate the superior plate 18 from the inferior plate 20 along the vertical direction. The ridges 82a-d slide along inclined connection grooves 60b, 160b, 62b, 162b (not shown in the FIG. 7B). While the first wedge member 22 is translating toward the implant trailing end 14, the second threaded portion 89 of the actuation member 26 engages the second bore 181 and causes the second wedge member 24 to translate toward the insertion end 12 of the implant 10. The inclined surfaces 177 and 178 of the second wedge member 24 slide along the ramp surfaces 44 and 144, so as to separate the superior plate 18 from the inferior plate 20 along the vertical direction V. The ridges 182a-182d slide along respective inclined connection grooves 60a, 160a, 62a, 162a (not shown in the FIG. 7B). The flange 28 remains disposed in the slots 52, 54, 152, 154 during actuation of the implant 10 and provides additional stability against sheer when the implant 10 is expanded. The embodiment shown in FIGS. 7A and 7B illustrate the superior plate 18 separating from the inferior plate 20 along a vertical direction V while remaining generally parallel to each other. In other alternate embodiments, the implant can be configured to such that a lordotic or kyphotic distraction is achieved. For example, the threaded portions of the actuation member can be configured to cause one wedge member to translate at a faster rate compared to the other wedge member. In such an embodiment, when the implant 10 is expanded, the superior plate 18 will be angularly offset from the inferior plate 20.

Referring to FIGS. 9-11B, in accordance with[, the] *an* alternative embodiment *of an* implant 110, the superior and interior plates 18 and 20, and specifically the [interior] *interiors thereof,* include opposing depressions [49] *49a-49b*, [149] *149a-149b* extending from the lumens 30, 131, toward the opposing ends 12, 14 of the implant. The first and second members 222 and 224 may include projecting tabs 120, 121, 122, and 123 [(tab 121 not shown)] protrude from the inclined surfaces 277 and 278 of the first and second wedge members 222 and 224. Further, the actuation member 226 can have a shorter length *measured between proximal and distal ends 227e and 227i thereof* compared to actuation member 26 described above. Otherwise, the implant 110 shown in FIGS. 9-11B is similarly configured to implant 10.

Figure 10A:
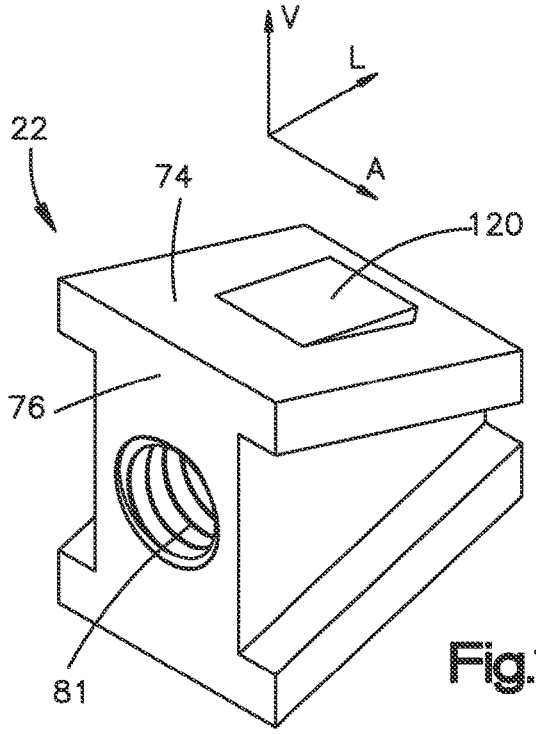
Figure 11A:
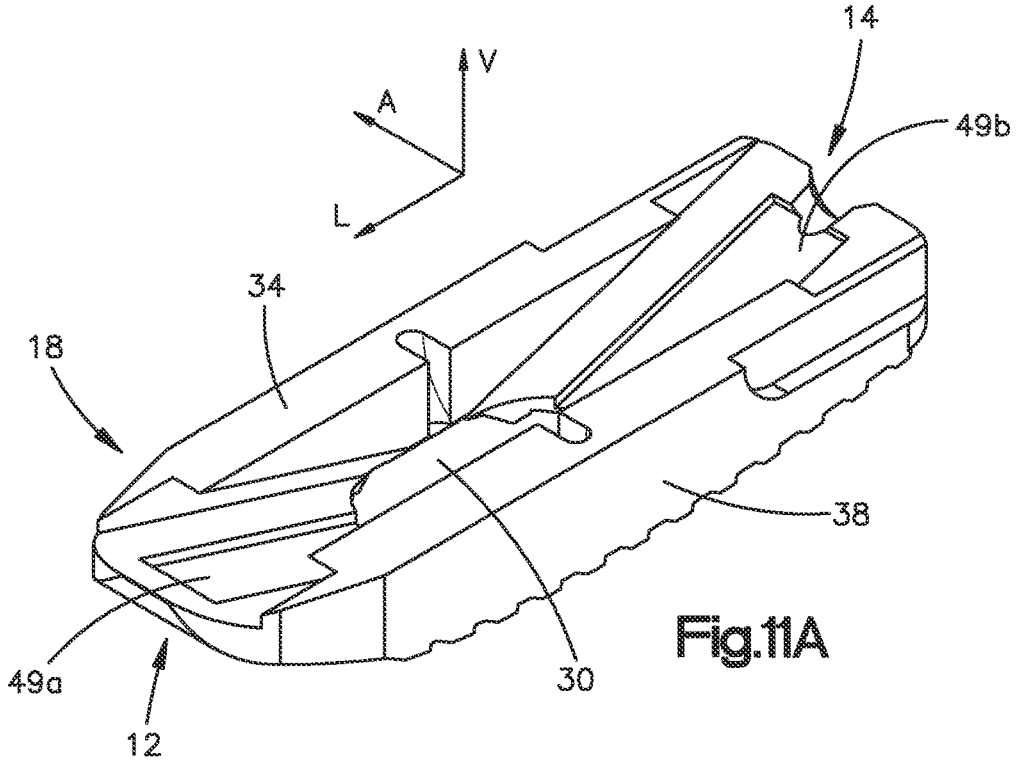
FIGS. 11A and 11B are perspective and inferior plan views of a plate, respectively, of the implant shown in FIG. 9.
Figure 11B:
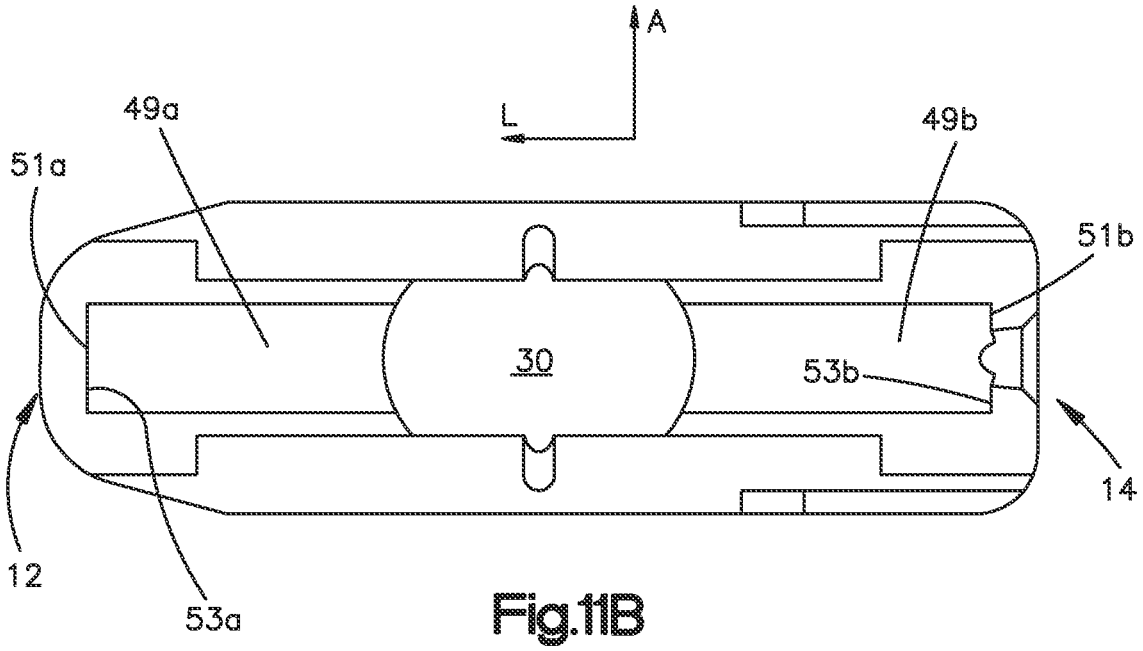

Referring the FIGS. 10A-10C, the depressions 79 include a first [49A] *depression 49a* and a second depression [49B] *49b* extending from the first and second ramp surfaces 44 and 46 along the vertical direction V. The depressions [49A, 49B] *49a, 49b* define a shoulders 51a, 51b, 53a, 53b, against which a portion the wedge members 222 and 224 shoulder against when the implant is expanded.

Another aspect of the present disclosure is a method of inserting and expanding for inserting an expandable implant into an intervertebral space. The patient the intervertebral space 9 is prepared using familiar techniques. One or more trial implants may be used to determine the appropriate size of the implant 10. Using the tool 100 (FIG. 8A), the expandable implant can be clasped between the tabs 101 and 102. Next, the expandable implant 10 is inserted into the intervertebral space 9 at the appropriate position between the vertebral bodies using a unilateral and/or bilateral posterior approach or an anterior approach. Next, a tool 350 having configured to engage the opening 90 the actuation member 26 can be used to actuate. Rotating the tool 350 and actuation member 26 causes the actuating member 26 to separate the opposed wedge members 22 and 24 along the longitudinal direction L simultaneously, thereby causing the first plate to separate from the second plate along the second direction such that the first plate is parallel to the second plate during the expanding step.

In accordance with an alternative embodiment, the method of insertion and expansion can use a tool 300 shown in FIG. 8C-8F. For instance, the tool 300 can clasp the implant 10 by inserting the tool tabs 312 and 314 into the implant indentations 98 and 99. The rotation member 318 can be slid into engagement with the actuation member 26. The tool 300 can be used to insert the implant into the intervertebral space 9. When the implant 10 is in the appropriate position, the rotation member 318 can be rotated, which rotates the actuation member 26 such that the implant is expanded to the desired expansion height.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. An expandable implant for insertion in an intervertebral space defined between a first vertebral body and a second vertebral body, the implant defining an insertion end spaced apart from a trailing end along a longitudinal direction, the implant comprising:

a first plate defining a first connection groove and a first projection;

a second plate opposed to the first plate along a vertical direction that is perpendicular to the longitudinal direction, the second plate defining a second connection groove and a second projection, wherein the first and second projections are positioned between the first and second connection grooves with respect to the vertical direction;

a first wedge member and a second wedge member spaced from the first wedge member along the longitudinal direction, each wedge member defining:

an inner end and a narrow end spaced apart from the inner end along the longitudinal direction, each wedge member tapering from the inner end to the narrow end, the inner ends of each wedge member facing one another;

a first side surface and a second side surface spaced from the first side surface along a transverse direction that is perpendicular to the longitudinal and vertical directions;

a first ridge and a second ridge spaced from the first ridge with respect to the vertical direction, each of the first and second ridges 1) elongated in a direction extending from the narrow end to the inner end of the associated wedge member, and 2) protruding from one of the first and second side surfaces of the associated wedge member in the transverse direction, wherein the first ridge is received within the first connection groove and overlaps the first projection in the [transverse] *vertical* direction so as to interlock the associated wedge member with the first plate, the second ridge is received within the second connection groove and overlaps the second projection in the [transverse] *vertical* direction so as to interlock the associated wedge member with the second plate, and the first and second wedge members are configured to translate away from one another along the longitudinal direction along the first and second plates from a first contracted configuration of the first and second wedge members into a second separated configuration of the first and second wedge members; and an actuation member coupled to the first wedge member and the second wedge member, the actuation member defining a shaft having a proximal end and a distal end spaced from the proximal end along the longitudinal direction, the shaft defining a first threaded portion and a second threaded portion proximal to the first threaded portion, the actuation member defining a flange extending toward the first and second plates, the flange disposed between the first and second threaded portions, the actuation member configured to translate the first and second wedge members from the first contracted configuration into the second separated configuration so as to separate the first plate from the second plate along the vertical direction,

*wherein the implant is configured to expand from a collapsed configuration into an expanded configuration, the expanded configuration is defined as when the first plate is spaced apart from the second plate along the vertical direction, and when the implant is in the collapsed configuration, the inner ends of each wedge member abut the flange.*

2. The implant of claim 1, wherein the first threaded portion has a first thread direction, and [a] *the* second threaded portion has a second thread direction that is different than the first thread direction.

3. The implant of claim 2, wherein the first wedge member includes a first bore extending along the first direction between the narrow end and the inner end of the first wedge member, and the second wedge member includes a second bore extending along the first direction between the narrow end and the inner end of the second wedge member, wherein the first bore at least partially receives the first threaded portion of the actuation member, and the second bore at least partially receives the second threaded portion of the actuation member.

4. The implant of claim 1, wherein the first plate defines a first proximal ramp inclined toward the trailing end of the implant, and the second plate defines a second proximal ramp inclined toward the trailing end of the implant, wherein either of the first or second wedge member is configured to translate along the first and second proximal ramp toward the trailing end of the implant.

5. The implant of claim 4, wherein *the* first plate defines a first distal ramp inclined toward the insertion end of the implant, and the second plate defines a second distal ramp inclined toward [either of] the insertion end of the implant, wherein the other of the first or second wedge member is configured to translate along the first and second distal ramp toward the insertion end of the implant.

6. The implant of claim 1, wherein each wedge member defines a body having a first inclined surface angularly offset from a second inclined surface, wherein the first and second inclined surfaces extend from the inner end toward the narrow end.

7. The implant of claim 6, wherein the first ridge extends along the first inclined surface, the second ridge extends along the second inclined surface, and the first and second ridges are configured to slidably couple with the first and second plates, respectively.

8. The implant of claim 6, wherein the first inclined surface defines a top surface of the associated wedge member, the second inclined surface defines a bottom surface of the associated wedge member, the first ridge is contiguous with the first inclined surface, and the second ridge is contiguous with the second inclined surface.

[9. The implant of claim 1, wherein the implant is configured to expand from a collapsed configuration into an expanded configuration, the expanded configuration is defined as when the first plate is spaced apart from the second plate along the vertical direction, and when the implant is in the collapsed configuration, the inner ends of each wedge member abut the flange.]

10. The implant *of* claim [9] *1*, wherein the first plate defines a first lumen and the second plate defines a second lumen aligned with the first lumen, wherein when the implant is in the collapsed configuration, at least a portion of the first wedge member and the second wedge member is at least partially disposed in the first lumen and the second lumen.

11. The implant of claim 10, wherein the inner end of each wedge member includes a superior tip and an inferior tip spaced apart from the superior tip along the vertical direction, wherein when the implant is in the collapsed configuration, the superior tip extends into the first lumen and is at least aligned with a first bone contacting surface of the first plate, and the inferior tip extends into the second lumen and is at least aligned with a second bone contacting surface of the second plate.

12. The implant of claim 1, wherein the inner ends of the first and second wedge members are spaced apart to at least partially define a gap extending therebetween, and the flange is configured to extend through the gap and at least partially into the first and second plates.

13. The implant of claim 12, wherein when the first wedge member and the second wedge member separate from the first contracted configuration into the second separated configuration, the dimension of the gap is increased.

14. The implant of claim 1, wherein the first and second connection grooves and the first and second ridges are each sloped with respect to the longitudinal direction.

15. The implant of claim 14, wherein the first and second ridges are configured to ride along the first and second connection grooves, respectively, responsive to translation of the associated wedge member from the first contracted configuration to the second separated configuration so as to separate the first plate from the second plate along the vertical direction.

16. The implant of claim 1, wherein each wedge member further comprises a third ridge and a fourth ridge spaced from the third ridge with respect to the vertical direction, wherein, the third ridge protrudes, in the transverse direction, from the other of the first and second side [surface] *surfaces* of the associated wedge member from which the first ridge protrudes;

the fourth ridge protrudes, in the transverse direction, from the other of the first and second side surfaces of the associated wedge member from which the second ridge protrudes; and each of the third and fourth ridges is elongated in a direction extending from the narrow end to the inner end of the associated wedge member.

17. The implant of claim 16, wherein the first and third ridges are parallel with each other, and the second and fourth ridges are parallel with each other.

18. The implant of claim 1, wherein:

the first wedge member defines a first threaded feature coupled to the first threaded portion of the shaft;

the second wedge member defines a second threaded feature coupled to the second threaded portion of the shaft; and the actuation member is configured to translate the first and second wedge members from the first contracted configuration into the second separated configuration responsive to rotation of the shaft about [the] *a* central axis *of the shaft*; and the first and second threaded portions of the shaft have different thread pitches so as to cause the first and second wedge members to translate at different rates responsive to rotation of the shaft in a manner causing the first and second plates to be separated by a first distance in the vertical direction at the insertion end and by a second distance in the vertical direction at the trailing end, and the first distance is different than the second distance.

19. An implant for insertion in an intervertebral space defined between a first vertebral body and a second vertebral body, the implant defining an insertion end spaced apart from [an] *a* trailing end along a first direction, the implant comprising:

a first plate defining a first connection groove and a first projection;

a second plate opposing the first plate along a second direction that is perpendicular to the first direction, the second plate defining a second connection groove and a second projection, wherein the first and second projections are positioned between the first and second connection grooves with respect to the second direction;

a first wedge member and a second wedge member spaced apart from the first wedge member along the first direction so as to define at least a gap between the first and second wedge members, each wedge member defining:

a first end and a second end spaced from the first end along the first direction, the first ends of each wedge member facing one another so as to define [a] *the* gap therebetween;

a first side surface and a second side surface spaced from the first side surface along a third direction that is perpendicular to the first and second directions;

a first ridge and a second ridge spaced from the first ridge with respect to the second direction, each of the first and second ridges 1) elongated in a direction extending from the first end to the second end of the associated wedge member, and 2) protruding from one of the first and second side surfaces of the associated wedge member in the third direction, wherein the first ridge is received within the first connection groove and overlaps the first projection in the [third] *second* direction so as to interlock the associated wedge member to the first plate, the second ridge is received within the second groove and overlaps the second projection in the [third] *second* direction so as to interlock the associated wedge member to the second plate, and the first wedge member and the second wedge member are translatable along the first and second plates along the first direction;

an actuation member defining a shaft having a first threaded portion coupled to the first wedge member and a second threaded portion spaced from the first threaded portion along the first direction, the second threaded portion coupled to the second wedge member; and a flange extending radially from the actuation member at least partially into the gap and at least partially into the first and second plates, the flange disposed between the first and second threaded portions of the shaft, wherein, when the actuation member is actuated, the first wedge member and the second wedge member separate from each other along the first direction so as to separate the first plate from the second plate along the second direction,

*wherein the implant is configured to expand from a collapsed configuration into an expanded configuration, the expanded configuration is defined as when the first plate is spaced apart from the second plate along the vertical direction, and when the implant is in the collapsed configuration, the inner ends of each wedge member abut the flange.*

20. The implant of claim 19, further comprising a first lumen extending through the first plate, and a second lumen extending through the second plate and axially aligned with the first lumen.

21. The implant of claim 20, wherein the first plate defines a bone contacting surface and an inner surface opposed to the bone contacting surface, the inner surface defining a first ramp that extends from the first lumen toward the [first] *insertion* end[of the first plate], and a second ramp extending from the first lumen toward the [second] *trailing* end[of the first plate], wherein the first and second ramps slidingly mate with the respective first and second [first] wedge members.

22. The implant of claim 21, wherein at least the first ramp defines an elongate depression, wherein the elongate depression is configured to receive a tab extending from either of the first wedge member or the second wedge member along the second direction, wherein [the tab is configured to abut] a portion of the depression *is configured to abut the tab* so as to limit advancement of the first and second wedge members relative to the first plate.

23. The implant of claim 21, wherein the second plate defines a second bone contacting surface and an inner surface opposed to the second bone contacting surface, the inner surface of the second plate defining a first ramp that extends from the second lumen toward the [first] *insertion* end[of the second plate], and a second ramp extending from the second lumen toward the [second] *trailing* end[of the second plate], wherein the first and second ramps slidingly mate with the respective first and second [first] wedge members.

24. The implant of claim 19, wherein the first plate defines a first bone contacting surface extending between the trailing end and the insertion end, and a first pair of opposed walls extending from the first bone contacting surface along the second direction, and the second plate defines a second bone contacting surface extending between the trailing end and the insertion end, the second bone contacting surface spaced from the first bone contacting surface along the second direction, and the second [bone] plate defines a second pair of opposed walls extending from the second bone contacting surface along the second direction toward the first plate, wherein the first and second pair of opposed walls each at least partially define a cavity configured to support the first and second wedge members.

25. The implant of claim 24, wherein one of the first pair of opposed walls defines at least one slot disposed between the insertion end and the trailing end, wherein the at least one slot is configured to receive a portion of the flange.

26. The implant of claim 24, wherein the first pair of opposed walls each define a first and second opposing slot, and the second pair of opposed second walls define a third and fourth opposing slot, wherein the first, second, third, and fourth opposing slots are disposed between the insertion end and the trailing end of the implant, and each slot is configured to receive a portion of the flange.

27. The implant of claim 24, wherein at least one wall of the first or second pair of opposed walls defines the first connection groove and the first projection, and the first connection groove is recessed into the at least one wall along the third direction.

*28. A system for replacing an intervertebral disc with an intervertebral spacer to fuse two adjacent vertebral bodies, the system comprising:*

*an expandable implant configured for insertion into an intervertebral space, the implant defining an insertion end spaced from a trailing end along a longitudinal direction, the implant comprising:*

*a superior plate and an inferior plate opposite the superior plate along a vertical direction perpendicular to the longitudinal direction, the superior plate defining a first sidewall and a second sidewall spaced from the first sidewall along a transverse direction that is perpendicular to the longitudinal and vertical directions, wherein the first sidewall defines a first slot and the second sidewall defines a second slot aligned with the first slot along the transverse direction, and each of the first and second slots is partially defined by opposed surfaces that face each other along the longitudinal direction in the respective first and second sidewalls;*

*a first wedge member and a second wedge member spaced from the first wedge member along the longitudinal direction, wherein the first and second wedge members are coupled to the superior and inferior plates, each wedge member being tapered so as to define at least a superior inclined surface; and*

*an actuation member configured to cause the first and second wedge members to translate along the longitudinal direction so as to cause the superior inclined surface of each wedge member to bear against the superior plate, thereby expanding the implant from a collapsed configuration to an expanded configuration by increasing a distance between the superior and inferior plates along the vertical direction, wherein the actuation member defines a flange, and the first and second slots are configured to slidingly and matingly receive respective portions of the flange such that relative sliding motion occurs between the flange and the first and second slots as the distance between the superior and inferior plates increases; and*

*an elongate member elongate along an axis, the elongate member having an engagement end configured to engage the actuation member, wherein the elongate member is movable to actuate the actuation member, thereby causing the first and second wedge members to translate along the longitudinal direction.*

*29. The system of claim 28, wherein 1) each wedge member defines a first end and a second end spaced from each other along the longitudinal direction, and the superior inclined surface of each wedge member is tapered between the respective first and second ends.*

*30. The system of claim 29, wherein the superior plate defines a first lumen and the inferior plate defines a second lumen aligned with the first lumen along the vertical direction, wherein when the implant is in the collapsed configuration, at least one of the first and second wedge members is at least partially disposed in the first lumen.*

*31. The system of claim 30, wherein the first or second end of each of the first and second wedge members includes a superior tip, wherein when the implant is in the collapsed configuration, the superior tip of the at least one of the first and second wedge members extends into the first lumen and is at least aligned with a first bone contacting surface of the superior plate along the longitudinal direction.*

*32. The system of claim 30, wherein:*

*the superior plate defines a first proximal ramp that extends from the first lumen toward the trailing end and a first distal ramp that extends from the first lumen toward the insertion end, the first proximal ramp is inclined toward the first lumen, and the first distal ramp is inclined toward the first lumen;*

*the superior inclined surface of the first wedge member is configured to slidably mate with the first proximal ramp: and*

*the superior inclined surface of the second wedge member is configured to slidably mate with the first distal ramp.*

*33. The system of claim 29, wherein the inferior plate defines first and second sidewalls opposite each other along the transverse direction, wherein:*

*the first sidewall of at least the inferior plate defines a first indentation at the trailing end, and*

*the second sidewall of at least the inferior plate defines a second indentation at the trailing end, wherein the first indentation is spaced from the second indentation along the transverse direction, and the first and second indentations are configured to receive respective first and second tabs of an implant-supporting member.*

*34. The system of claim 33, wherein the actuation member defines a socket, the engagement end of the elongate member is receivable within the socket for rotatably coupling with the actuation member, and each of the first indentations and the second indentations is offset from the socket along the transverse direction.*

*35. The system of claim 28, wherein the flange is disposed between the first and second wedge members with respect to the longitudinal direction.*

*36. The system of claim 35, wherein the flange defines a distal facing surface and a proximal facing surface spaced from each other along the longitudinal direction.*

* * * * *